(12) United States Patent
Uehara et al.

(10) Patent No.: US 9,226,706 B2
(45) Date of Patent: Jan. 5, 2016

(54) SYSTEM, APPARATUS, AND METHOD FOR PROMOTING USAGE OF CORE MUSCLES AND OTHER APPLICATIONS

(71) Applicant: Alert Core, Inc., Kaneohe, HI (US)

(72) Inventors: Gregory Takeo Uehara, Kaneohe, HI (US); Brian Taylor Brunn, Bee Cave, TX (US)

(73) Assignee: Alert Core, Inc., Kailua, HI (US)

( * ) Notice: Subject to any disclaimer, the term of this patent is extended or adjusted under 35 U.S.C. 154(b) by 98 days.

(21) Appl. No.: 14/132,808

(22) Filed: Dec. 18, 2013

(65) Prior Publication Data

US 2014/0174174 A1 Jun. 26, 2014

Related U.S. Application Data

(60) Provisional application No. 61/739,160, filed on Dec. 19, 2012.

(51) Int. Cl.
*A61B 5/22* (2006.01)
*A61B 5/11* (2006.01)
*G06F 19/00* (2011.01)
*G06K 9/00* (2006.01)
*G09B 19/00* (2006.01)
*A61B 5/00* (2006.01)
*A63B 23/02* (2006.01)

(52) U.S. Cl.
CPC .............. *A61B 5/227* (2013.01); *A61B 5/1121* (2013.01); *A61B 5/4519* (2013.01); *A61B 5/6823* (2013.01); *G06F 19/3481* (2013.01); *G06K 9/00342* (2013.01); *G09B 19/0038* (2013.01); *A61B 5/1122* (2013.01); *A61B 5/1124* (2013.01); *A61B 5/6831* (2013.01); *A61B 5/744* (2013.01); *A61B 2503/10* (2013.01); *A63B 23/02* (2013.01)

(58) Field of Classification Search
CPC .... A61B 5/227; A61B 5/1121; A61B 5/6823; A61B 5/6831; A61B 5/744; A61B 5/1122; A61B 5/1124; A61B 2503/10; A61B 23/02; A61B 5/4519; G09B 19/0038; G06F 19/3481; G06K 9/00342
USPC .......................................... 73/379.01; 700/91
See application file for complete search history.

(56) References Cited

U.S. PATENT DOCUMENTS

| | | | |
|---|---|---|---|
| 2002/0143277 A1* | 10/2002 | Wood et al. | 600/595 |
| 2002/0170193 A1* | 11/2002 | Townsend et al. | 33/512 |
| 2002/0177882 A1* | 11/2002 | DiLorenzo | 607/45 |
| 2003/0065365 A1* | 4/2003 | Zhu et al. | 607/17 |
| 2003/0135140 A1* | 7/2003 | Bosco | 601/46 |
| 2005/0043661 A1* | 2/2005 | Nashner | 602/26 |
| 2006/0276701 A1* | 12/2006 | Ray | 600/354 |
| 2007/0167879 A1* | 7/2007 | Cochran | 600/595 |
| 2009/0005834 A1* | 1/2009 | Weintraub et al. | 607/48 |
| 2011/0184318 A1* | 7/2011 | Kodama | 600/588 |
| 2011/0230782 A1* | 9/2011 | Bartol et al. | 600/546 |
| 2011/0270135 A1* | 11/2011 | Dooley | A61B 5/1121 600/595 |
| 2012/0116256 A1* | 5/2012 | Stavdahl et al. | 600/595 |
| 2012/0259648 A1* | 10/2012 | Mallon et al. | 705/2 |
| 2014/0163412 A1* | 6/2014 | Jacobson et al. | 600/546 |

\* cited by examiner

*Primary Examiner* — Lisa Caputo
*Assistant Examiner* — Philip Cotey
(74) *Attorney, Agent, or Firm* — Staniford Tomita LLP

(57) ABSTRACT

Embodiments disclosed include a system and method for development of core muscles' support, comprising a means for identifying a user qualifying movement, a means for detecting a core muscle contraction in the identified qualifying movement, a means for discriminating between a core muscle contraction and no core muscle contraction in the identified qualifying movement; and a means to provide feedback to the user.

20 Claims, 57 Drawing Sheets

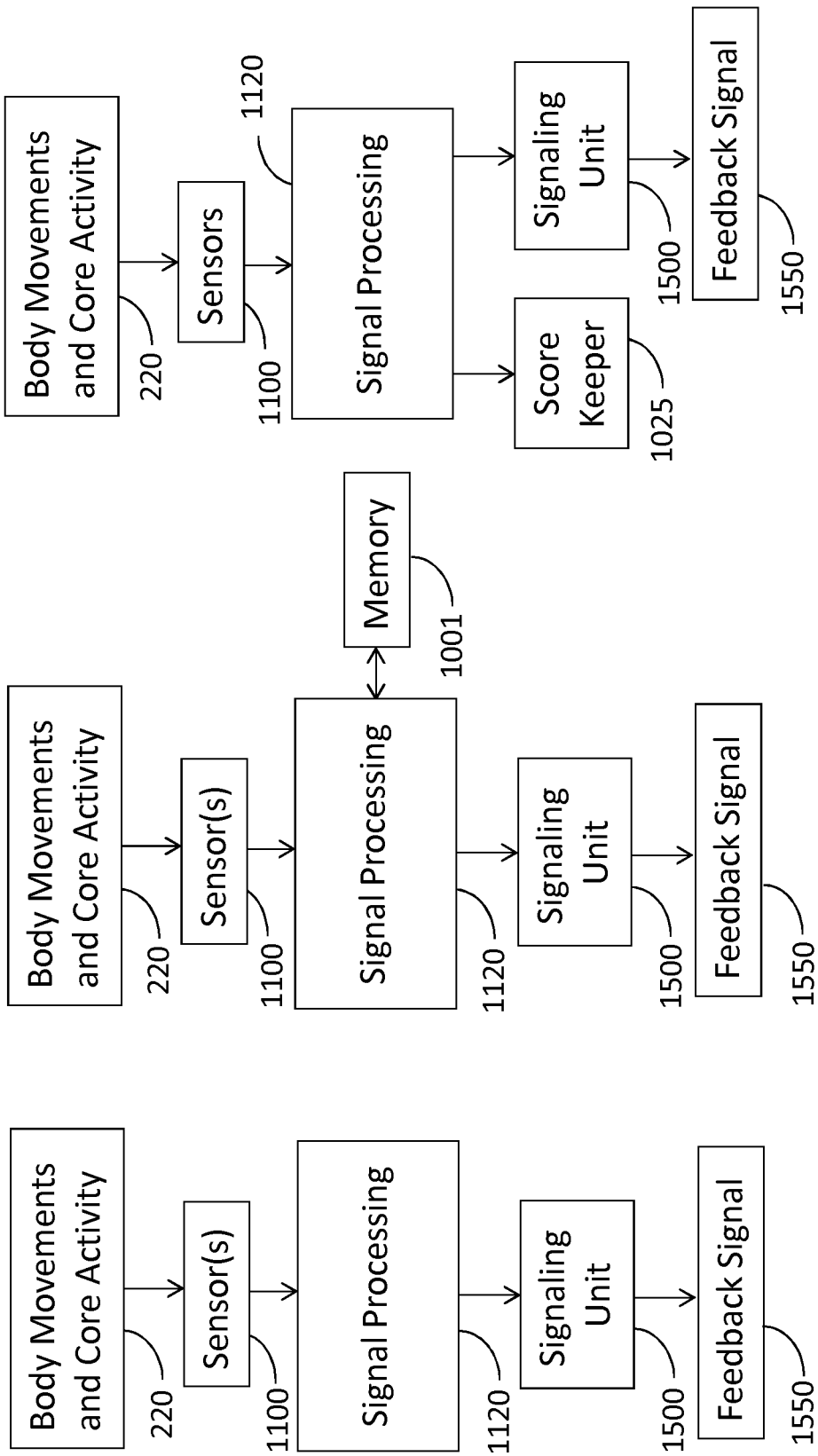

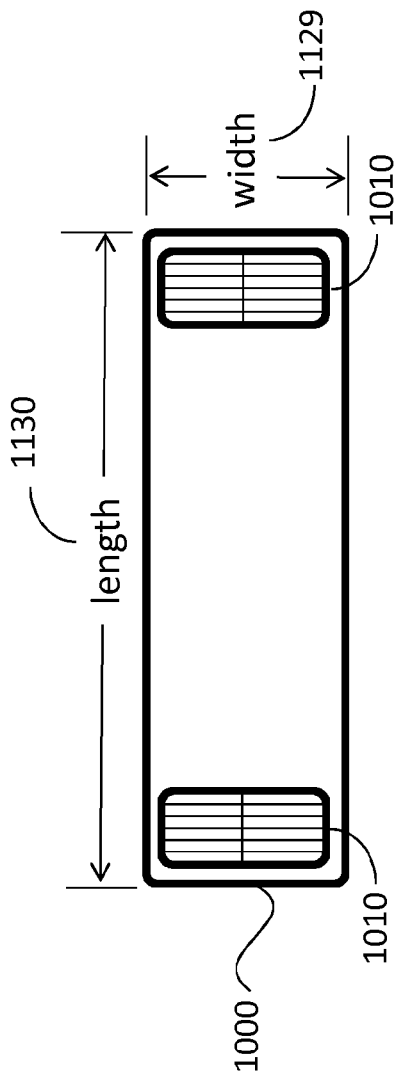
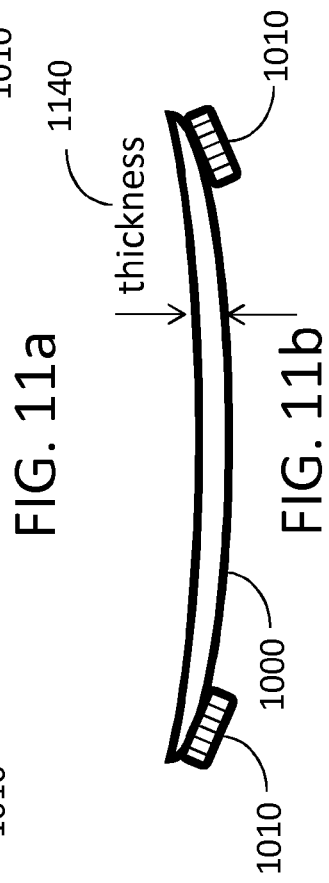
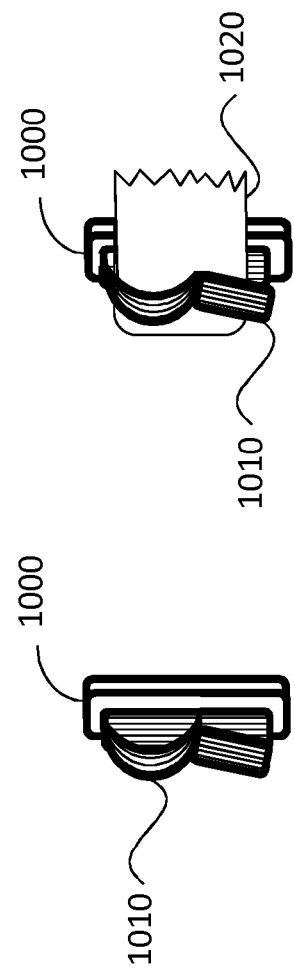
FIG. 11a
FIG. 11b
FIG. 11c
FIG. 11d

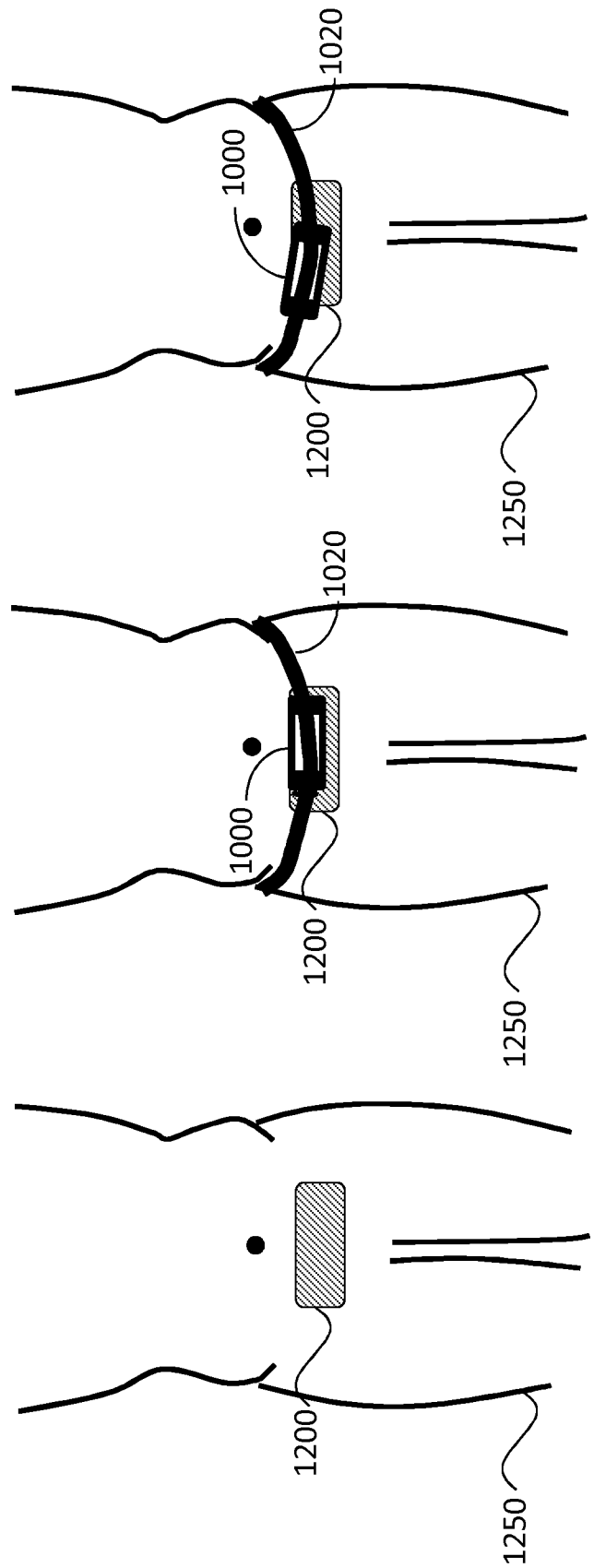

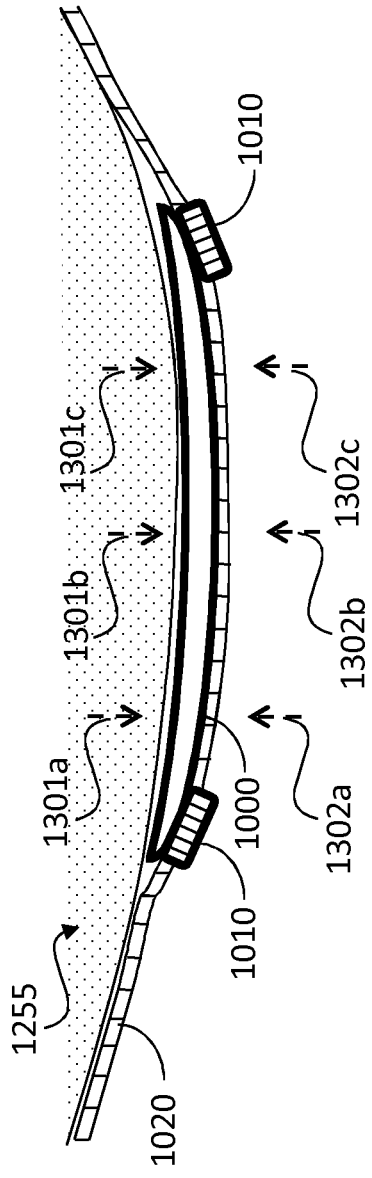
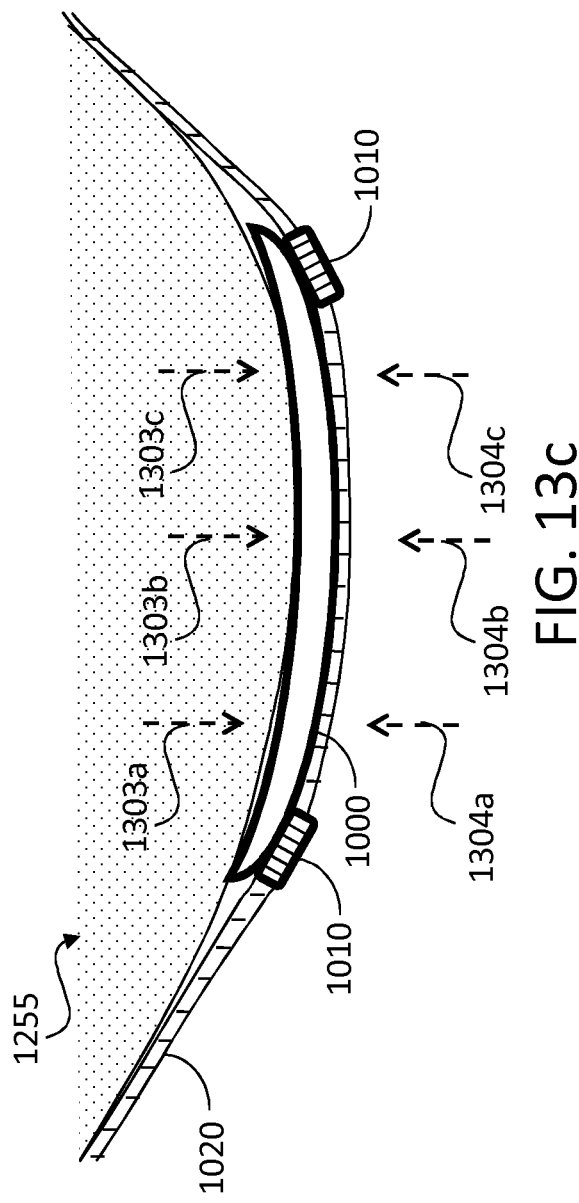

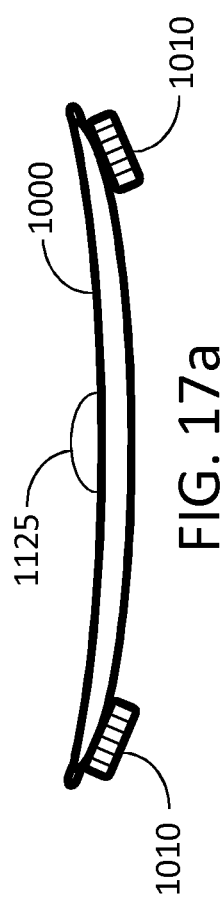
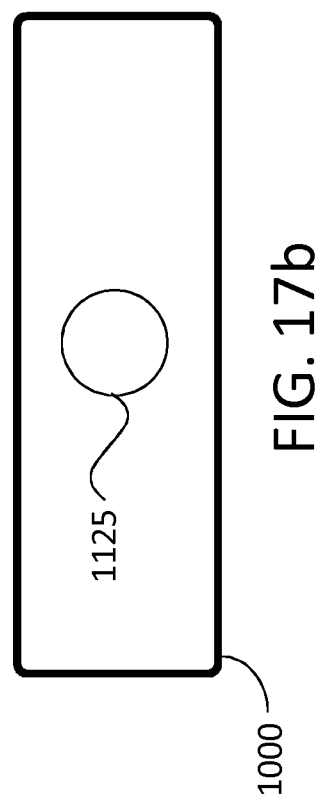
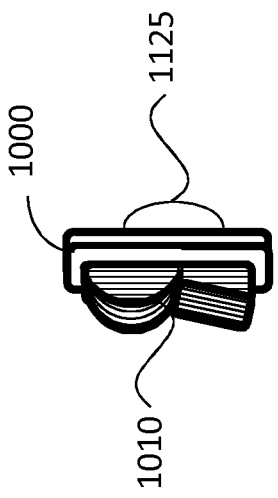
FIG. 17a
FIG. 17b
FIG. 17c

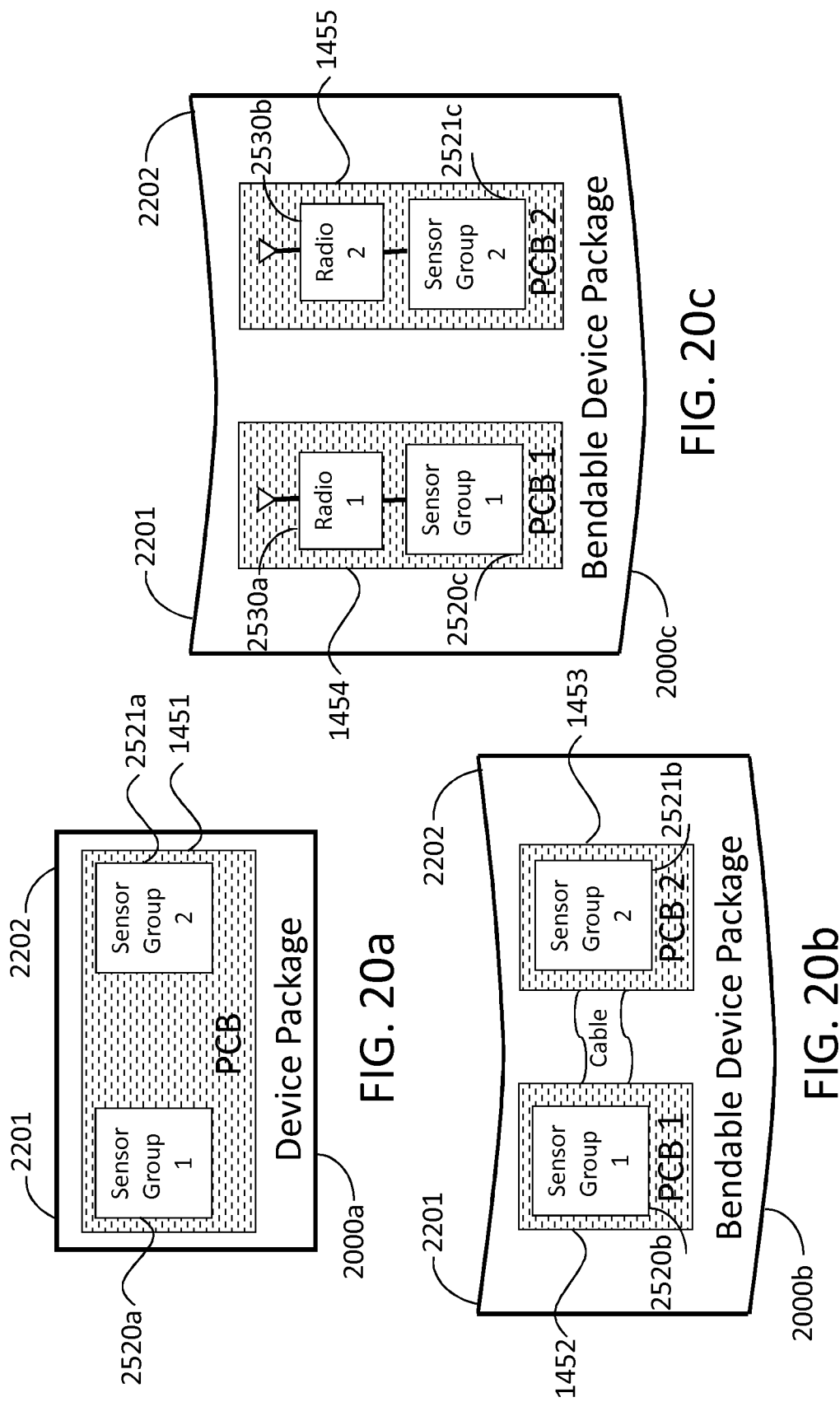

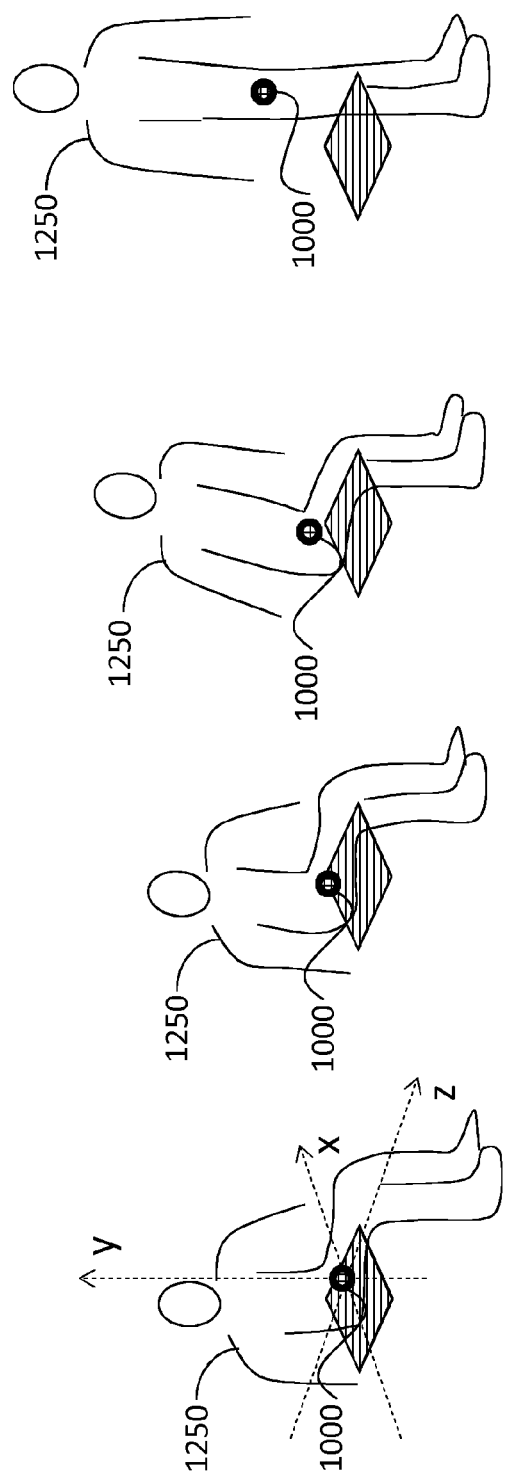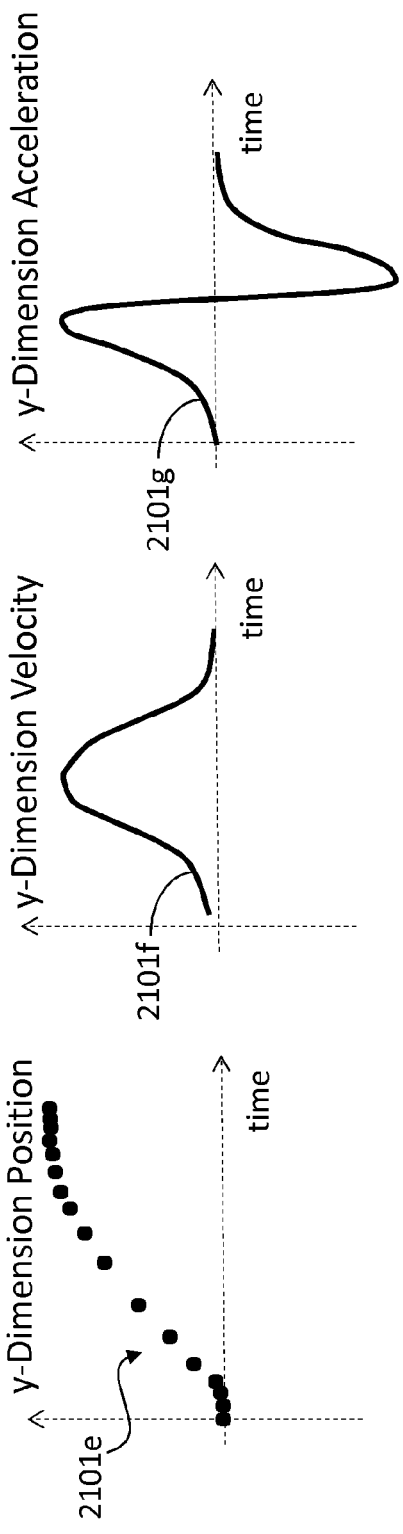

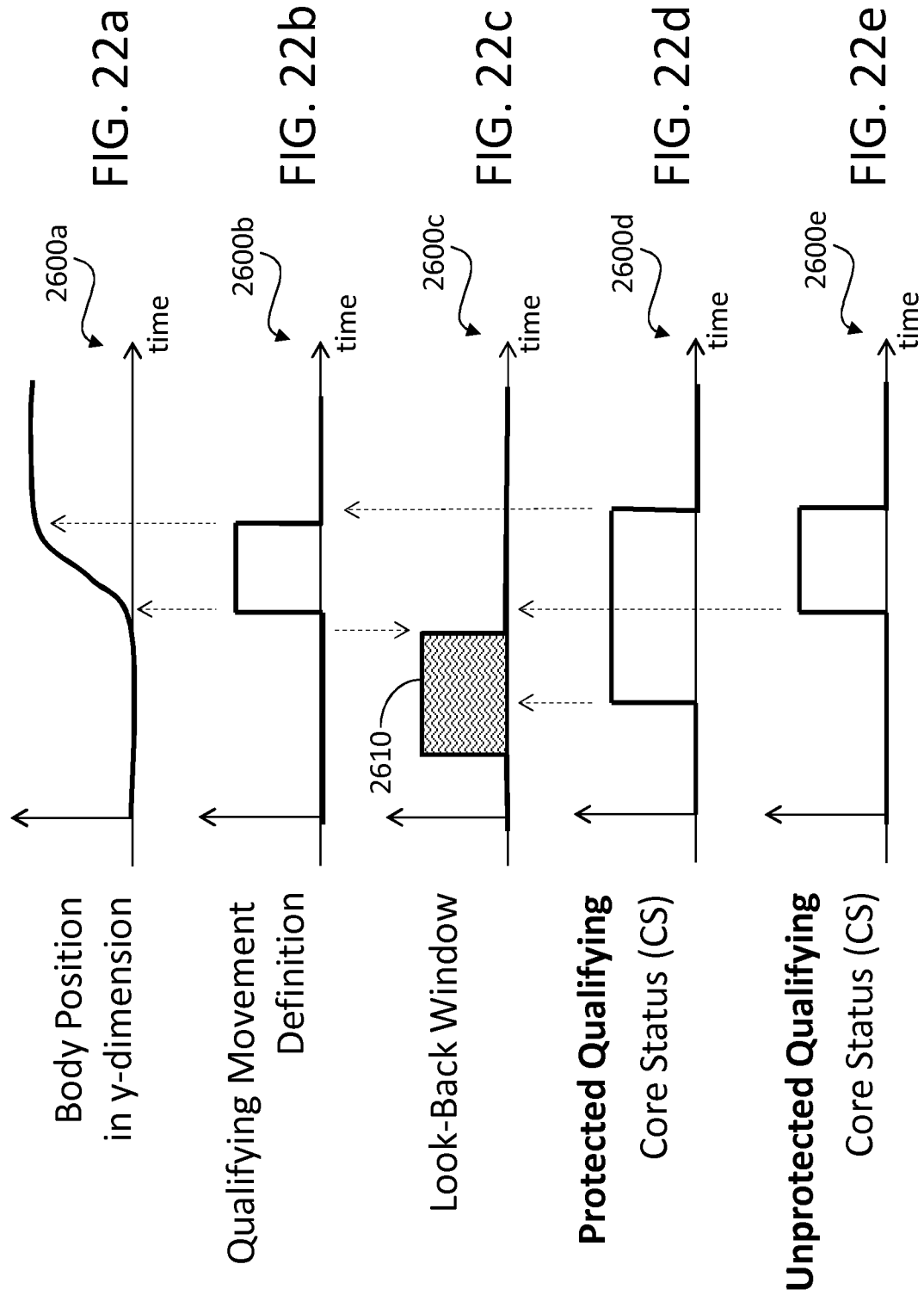

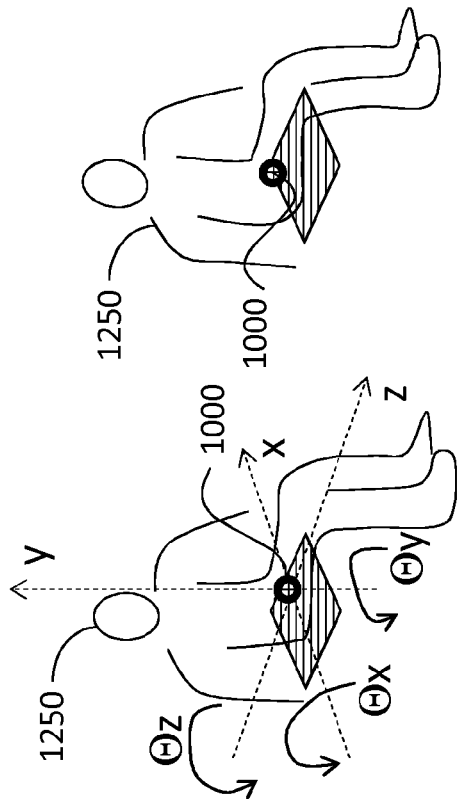
FIG. 24a
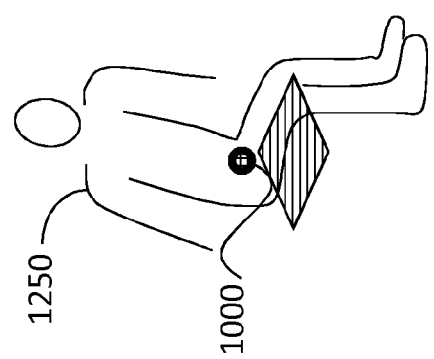
FIG. 24b
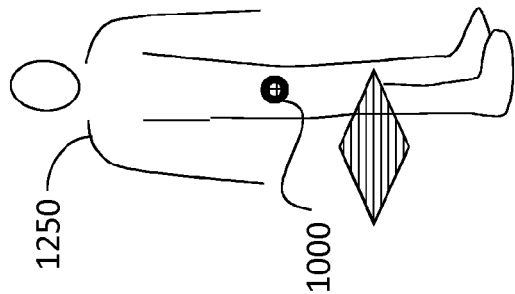
FIG. 24c
FIG. 24d
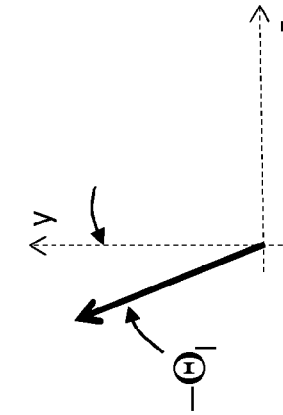
FIG. 24e
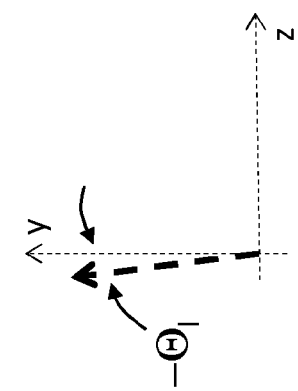
FIG. 24f
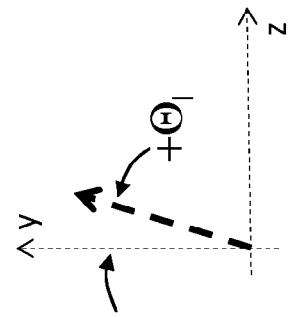
FIG. 24g
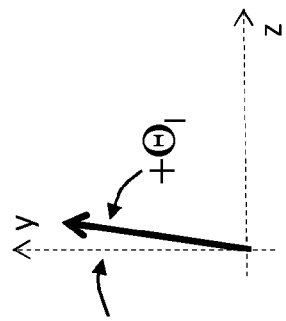
FIG. 24h

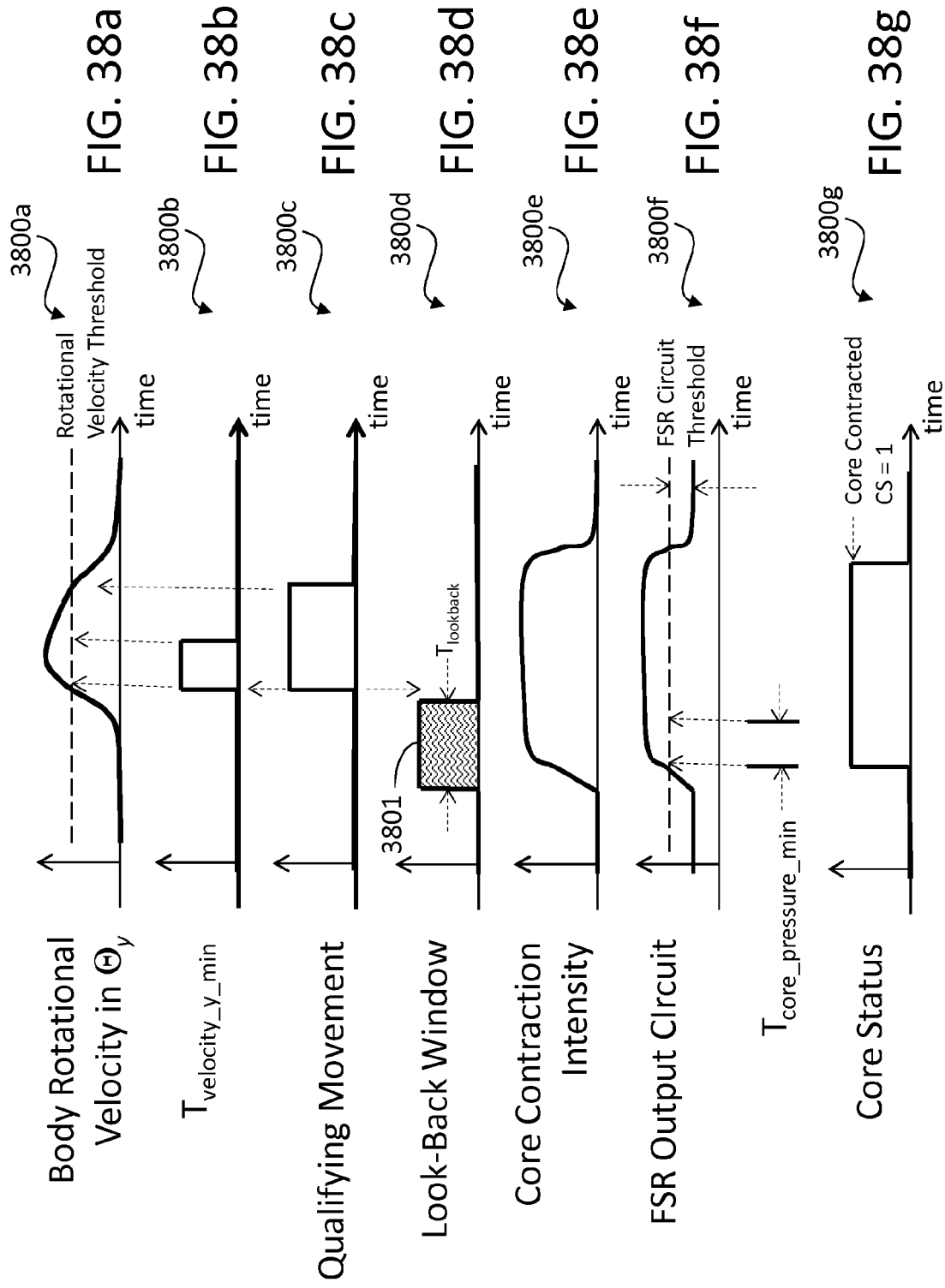

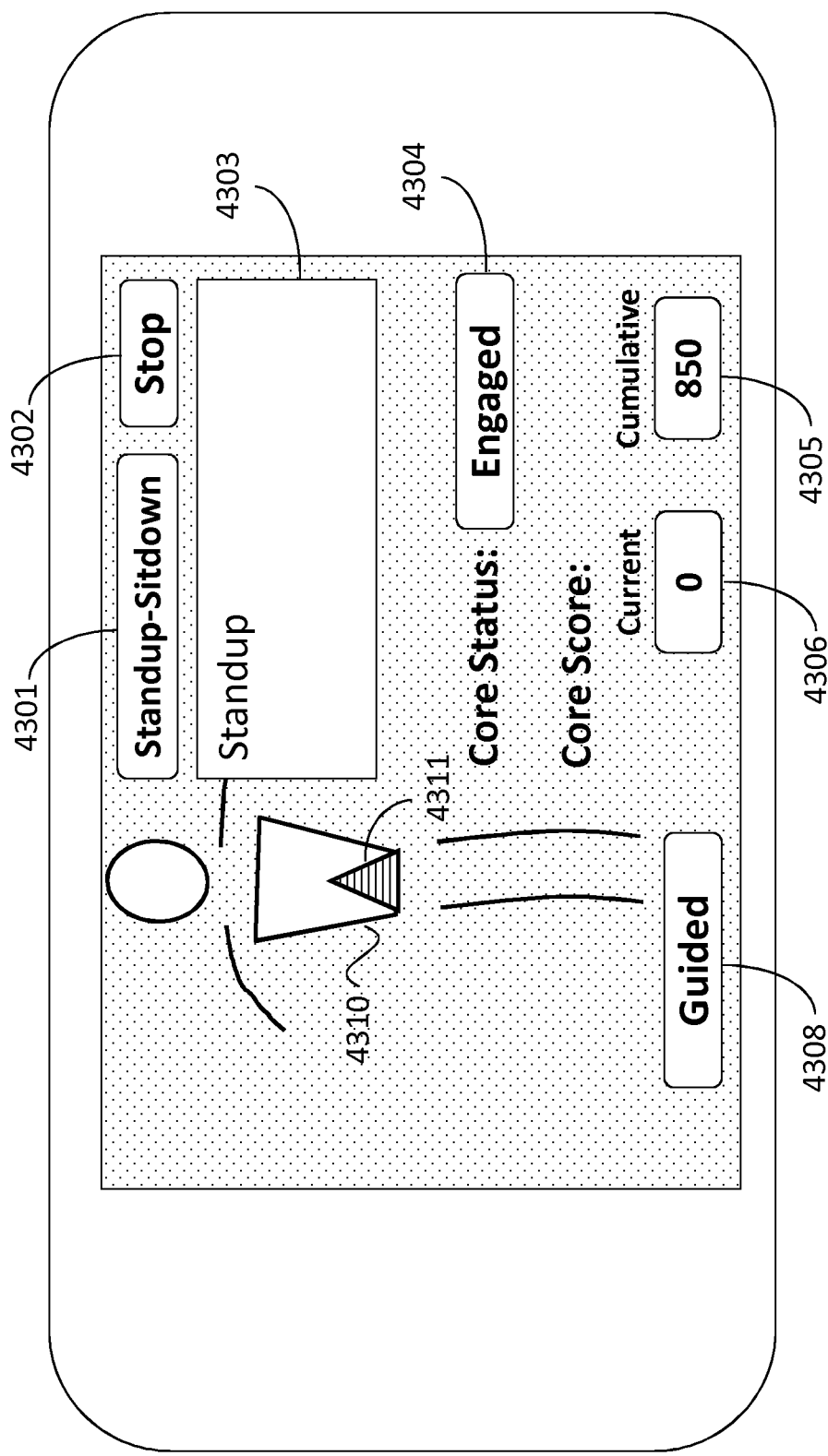

SYSTEM, APPARATUS, AND METHOD FOR PROMOTING USAGE OF CORE MUSCLES AND OTHER APPLICATIONS

CROSS-REFERENCE TO RELATED APPLICATIONS

This application claims the benefit of U.S. Provisional Application No. 61/739,160, entitled "SYSTEM FOR PROMOTING USAGE OF CORE MUSCLES AND OTHER APPLICATIONS", filed Dec. 19, 2012, the disclosure of which is incorporated herein by reference.

FIELD OF THE INVENTION

Embodiments disclosed relate to systems, methods and devices for development of support from core muscles by identifying user movements, and by detecting core muscle usage in conjunction with those identified movements. Embodiments also relate to discriminating between multiple identified movements, recognizing core muscle activity or lack of it thereof in those identified movements, and providing feedback to the user regarding a correct or incorrect core muscle use, acknowledging a core muscle use when appropriate, informing of an inappropriate core muscle use, and identifying a movement wherein a core muscle is not used but could be used.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

Core muscles or so-called core are comprised of a number of muscles with the primary muscles which provide foundational support located in the abdominal area of the body. These muscles can provide support and strength to the lumbo sacral junction, which is the region of the body where the spine connects to the pelvic bones.

Many large industries focus on development of muscles comprising the core muscles, for management of low-back and other body pain, as well as increased health and fitness, and improvement of one's body aesthetic. Since the core provides stability and strength to the body, there is much focus on core development to improve athletic performance.

There are a number of professionals and practitioners involved with developing and training the core. Health care professionals may focus on developing the core to manage pain, wherein such development may include reduction, elimination, and prevention of pain. Health care professionals include physical therapists, occupational therapists, chiropractors, physiatrists, and osteopathic, sports medicine, and orthopedic physicians. Practitioners and trainers may focus on working with patients and clients to develop their core muscles for strength and fitness, overall well-being, as well as for aesthetic reasons. These professionals may include personal and fitness trainers, Pilates and yoga instructors, and students and teachers of practices such as tai chi. There are a number of available instructional exercise videos and DVDs, on-line videos, and downloadable apps that focus on fitness, strength, body shaping, and/or agility training, and these generally include a substantial focus on development of the core. Coaches for a variety of sports including football, baseball, basketball, golf, soccer, and volleyball are increasingly encouraging the development and use of the core muscles for improved stability, balance, endurance, and performance.

In general, the aforementioned focus on core is on development and strengthening. Another focus for core training may be the timing or sequencing aspect of core contraction with respect to body movements. Core contraction, as used herein refers to a gentle tightening of the core muscles, in particular the inner unit core muscles, for support of the lumbo-sacral junction and the body overall. There are a number of foundational muscles included in the broad heading of core muscles, with the transverses abdominus generally agreed to be most important for lumbo-sacral junction support. The intensity of the contraction may scale with the increase in load on the body and additional muscles are generally recruited as needed.

In 1996, researchers identified a connection between the timing relationship of core contraction and body movements with low-back pain. They examined two groups of subjects. One group was experiencing low-back pain and the second group of subjects was not. Using ultra-sound sensor techniques, the core was monitored through the transverses abdominus muscle while the subjects performed rapid movements with their arms. They found subjects who were not experiencing low-back pain contracted their core milliseconds prior to the arm movements. While those who were experiencing low-back pain did not contract their core prior to the arm movements. One interpretation of this data is that contraction of the core adds stability to the lumbo-sacral junction, and therefore contraction of the core prior to certain body movements may be beneficial for low-back pain management. The benefits of timing training may extend well beyond pain management into overall fitness and strength improvement and the improvement of athletic performance.

Shortcomings of currently available products and system solutions include the following:

A. Monitoring the core muscles is difficult which makes learning difficult since without feedback, it is difficult to know whether or not the core is being contracted properly. There are no known relatively low-cost devices or systems to enable the core to be easily monitored. Even physical therapists or personal trainers may use their hands on their client to feel if they are contracting their core. This is further complicated if the subject is moving and contracting their core simultaneously.

B. Teaching the timing aspect of core training is difficult since with currently available devices and systems, it is difficult to monitor the core and body movements and their timing relationship.

C. Developing procedural memory to achieve desired timing relationships between core contractions and specific body movements requires repetition. Such repetition may be most effectively taught if the timing sequence may be encouraged and practiced throughout the day including morning, noon, and night.

D. Self-teaching or teaching one's self without an instructor is very difficult. There is a movement of increased personal responsibility for health care in the US due in part to increasing health costs and greater complexities in the health care system. With currently available devices and systems, it is difficult for an individual to learn about proper usage of their core muscles.

E. There are no known devices or systems that enable the promotion of core contraction support outside of training situations. Anecdotally, a person may spend an hour with a personal trainer in a fitness facility, spending much of the time focusing on development of the core, then (say) drop their car keys in the parking lot on their way to their next appointment and have no direct way to encourage or remind themselves to utilize their core for support as they bend down to pick up their keys.

Embodiments of the inventive devices and systems presented in this disclosure may address each of the short comings of currently available products and system solutions.

Embodiments disclosed include a device that may be worn on or near the body, and software that may be run coincidentally with the device on a handheld device such as a smart phone, electronic pad, or dedicated device or PC. In some applications, more than one device may be utilized in the system.

SUMMARY

Embodiments disclosed include a system for development of core muscles' support, comprising a means for identifying a user qualifying movement, a means for detecting a core muscle contraction in the identified qualifying movement, a means for discriminating between a core muscle contraction and no core muscle contraction in the identified qualifying movement; and a means to provide feedback to the user.

Embodiments disclosed include a device for development of core muscles' support comprising: a single or plurality of sensors, and a single or plurality of signal processors. The single or plurality of sensors is further coupled with the single or plurality of signal processors. Further the sensors coupled with the signal processors comprise means for detecting a qualifying movement and a core contraction, and further for detecting a timing relationship between the detected qualifying movement and core contraction, for determining if the movement is a protected qualifying movement or an unprotected qualifying movement, and for providing feedback to a user.

An embodiment includes a wearable device for assisting in the development of core muscle usage, comprising, a means to detect contraction of a user's core muscles, a means to communicate with an external device, and a means to provide measurable metrics. The wearable device further comprises a means to provide immediate feedback through an external device to improve the user's core muscle usage.

Embodiments disclosed include, in a computer aided system, a method for development of procedural memory for core support before and during qualifying movements, the method comprising, identifying the qualifying movements, identifying a user core contraction, discriminating between a protected and unprotected qualifying movement, and providing feedback depending on the result of the discriminating, to a user, to develop the said procedural memory.

Embodiments disclosed include, in a computer aided system, a method for development of procedural memory for core based support, comprising, via a single or plurality or sensors coupled with a single or plurality of signal processors, detecting a qualifying movement and a core contraction, detecting a timing relationship between the detected qualifying movement and core contraction; and determining if the movement is a protected qualifying movement or an unprotected qualifying movement.

Embodiments disclosed include a wearable, computer aided device for promoting core muscle usage, comprising, a means to detect contraction of wearer core muscles wherein contraction results in an inward, outward, or neutral movement of the core, a means to communicate with an external device, a means to provide measurable metrics to monitor progress of core contraction support, and a means to provide direct feedback to the external computing device to monitor and improve the wearer's core muscles' activity or movement to activate the wearer's use of their core muscles.

An embodiment includes a wearable device for assisting in the development of core muscle usage used with exercise equipment, comprising a means to translate movements on exercise equipment into identified qualifying movements and a means to communicate with the wearable device monitoring core contractions, and a means to determine if the exercise movement is a protected or unprotected qualifying movement, and a means to provide feedback to the user.

An embodiment includes a wearable device for assisting in the development of core muscle usage used with exercise video or app, comprising a means to encode onto the video identified qualifying movements simultaneous to an instructor's movements, and a means to communicate these qualifying movements with the wearable device monitoring core contractions, and a means to determine if the movement of a user following the movement the instructor is a protected or unprotected qualifying movement, and a means to provide feedback to the user.

An embodiment includes a wearable device for assisting in the teaching of proper core muscle usage used with an instructional video or app, comprising a means to encode onto the video or app time intervals when the core should be contracted simultaneous to the instruction on the video, and a means to communicate the contraction with the wearable device monitoring core contraction, and a means to determine if the movement of a user's core contraction performed simultaneous with the video is inward, outward, or neutral, and a means to provide feedback to the user.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 10a illustrates a functional diagram including elements of an embodiment of a system for improving core usage.

FIG. 10b illustrates the diagram of FIG. 10a with the explicit addition of memory.

FIG. 10c. illustrates the diagram of FIG. 10a with the addition of a Score Keeper to monitor the user's performance.

FIG. 11a illustrates an embodiment comprising packaging or housing that may be longer than it is wide.

FIG. 11b illustrates the thickness of the packaging, which in an embodiment, may be approximately one half inch or less.

FIG. 11c and FIG. 11d show how a preferred embodiment may include a clip that may connect to a strap, belt, or article of clothing.

FIG. 12a illustrates an embodiment of a location for placing the device on or near the body below the navel an above the groin as shown in the cross-hatched section.

FIG. 12b and FIG. 12c illustrate embodiment of the device attached to a belt and positioned in the preferred sensing location.

FIG. 13b illustrates a cross-section including the user's core section coupled to the device, wherein the device is being held to the user's core with an elastic belt and relative forces on either side of the device with the core in the relaxed state.

FIG. 13c illustrates the configuration of FIG. 13b and the change in forces on either side of the device with the core contracted.

FIG. 14b illustrates a side view of the elements in FIG. 14a.

FIG. 15d illustrates the strain gage sensor configured to experience bend of the device.

FIG. 17a-FIG. 17c illustrates an embodiment utilizing a force sense resistor, sensor bumper, with the embodiment of the device housing introduced in FIG. 11.

FIG. 20a-FIG. 20c show different embodiments of a device suitable for differential sensing. FIG. 20a illustrates the use of one PCB and two sensor groups. FIG. 20b illustrates the use of two PCBs connected by a cable. FIG. 20c illustrates the use of two PCBs connected through a wireless communication link.

FIG. 21a-FIG. 21d show diagrammatically, a user moving from a seated position to a standing position over a period of time of approximately one second.

FIG. 21e illustrates a plot of the location of the device in the y-dimensions approximately every 20 milliseconds; i.e., a plot of the movement of the device.

FIG. 21f illustrates the velocity of the device in the y-dimension over a similar period of time.

FIG. 21g illustrates the acceleration of the device in the y-dimension over a similar period of time.

FIG. 22a illustrates the body position in the y-dimension versus time of the user of FIG. 21 moving from a seated to standing position.

FIG. 22b illustrates the start and end points of the identified qualifying movement.

FIG. 22c illustrates a Look-Back Window ending at or before the point that the qualifying movement is identified to start.

FIG. 22d illustrates a protected qualifying movement, identified inside the Look-Back window. If a core contraction is detected inside of the look-back window and the core contraction continues through the duration of the qualifying movement, the movement may be considered a protected qualifying movement as indicated.

FIG. 22e illustrates an unprotected qualifying movement. If a core contraction does not begin inside the look-back window, the movement may be considered an unprotected qualifying movement as indicated.

FIG. 24a-FIG. 24d show the sequence of the user changing from a seated position to a standing position where the instantaneous lean is illustrated as shown in FIG. 24e through FIG. 24h.

FIG. 33a illustrates an example of the signal processing blocks in an implementation of FIG. 32a.

FIG. 38a shows Body Rotational Velocity signal plot versus time. FIG. 38b shows the period of time $T_{velocity\ y\ min}$ for which the body rotational velocity exceeds its' threshold. FIG. 38c shows identifying the timestamps of the start and end of the qualifying movement. FIG. 38d shows establishing of a look-back window, established with width $T_{look-back}$ ending just before start of identified qualifying movement. FIG. 38e shows core contraction. FIG. 38f shows output of the FSR output circuit. FIG. 38g shows the length of time for which the output from the FSR output circuit is greater than the FSR circuit threshold.

FIG. 43a-FIG. 43f show a conceptual example of the elements of a training software program. In this example, the user moving from a seated position to a standing position wherein the user is encouraged to contract their core before and through the movement and to relax them after standing.

DETAILED DESCRIPTION OF THE PREFERRED EMBODIMENT

Figure 1:
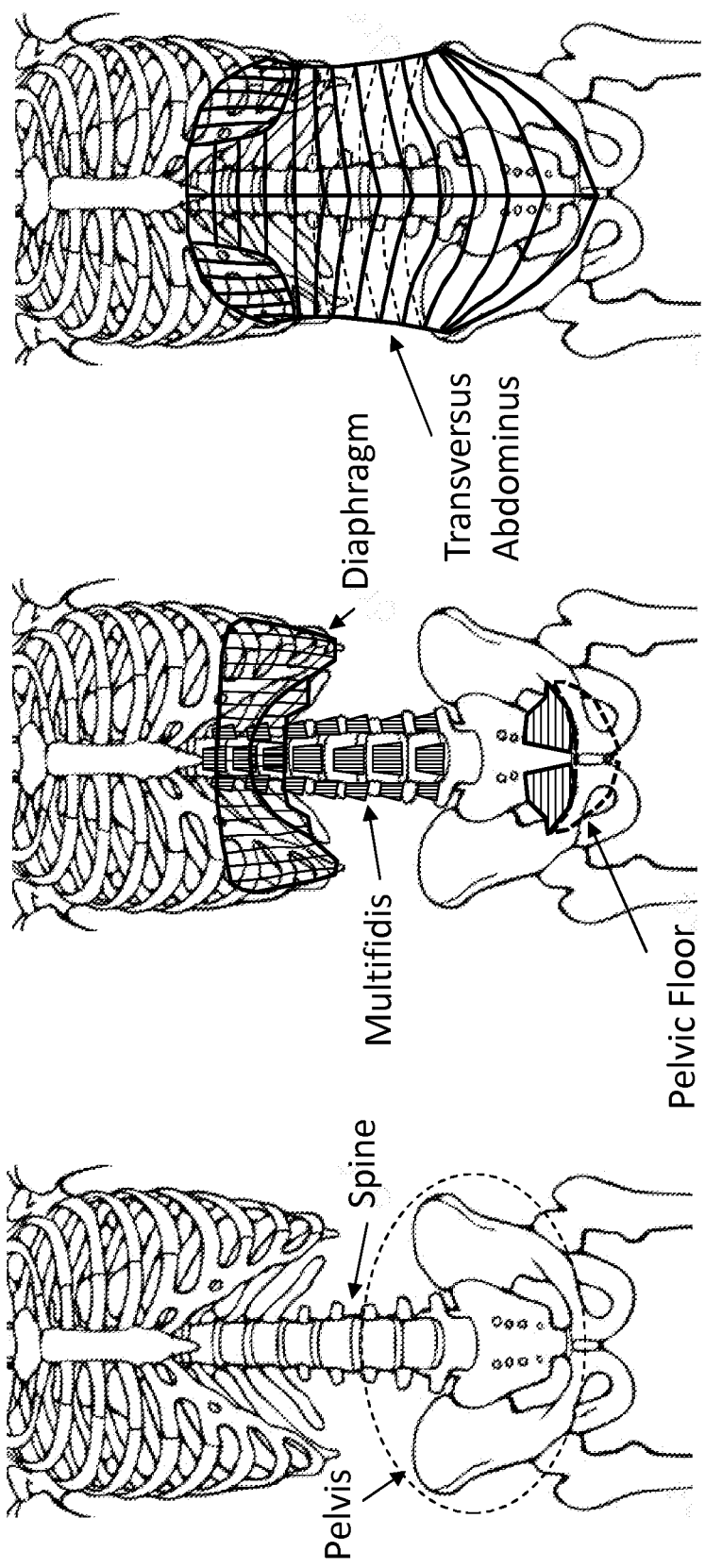
FIG. 1a illustrates a basic human skeleton with the spine and pelvis attachment identified in a region referred to as the lumbo-sacral junction.
FIG. 1b illustrates three of the inner unit core muscles including the multifidus, diaphragm, and pelvic floor.
FIG. 1c illustrates the transverses abdominus, the deepest of the inner unit core muscles.

The following terms have these corresponding definitions in the description:

Procedural memory is memory for the performance of a particular type or types of actions, often residing below the level of conscious awareness. Procedural memory may be developed when a certain procedure or sequence of steps is performed by an individual in a specific order multiple times, such that the sequence of steps becomes somewhat automatic as part of a specific action or type of related actions for that individual. One of the outcomes of regular use of one embodiment of the invention may be to develop procedural memory in an individual to contract some or all of the inner unit core muscles when the individual is performing motions for which core support would be beneficial.

Those skilled in the art will appreciate that the present invention may be implemented with many different types of computer system configurations, including hand-held devices, multiprocessor systems, microprocessor based or programmable consumer electronics, network personal computers, minicomputers, mainframe computers, and the like. The present invention can also include multiple computer programs which embody the functions described herein and illustrated in the drawings, and flow charts. However, it should be apparent that there could be many different ways of implementing the invention in computer programming, and the invention should not be construed as limited to any one set of computer program instructions. Further, a skilled programmer would be able to write such a computer program to implement the disclosed invention without difficulty based on the drawings, flow charts, and programming logic and associated description in the application text.

Embodiments disclosed include systems and methods that promote and cause the use of core muscles for simple movements such as leaning forward in a seated position, standing up from a seated position, and sitting down from a standing position. Through repetition, the user's procedural memory for core contraction support when performing these basic movements may be developed. The invention may also be utilized to implement systems that promote use of the core muscles for more complex movements including those in athletics and athletic training.

An embodiment includes a system for development of core muscles' support, comprising a means for identifying a user qualifying movement, a means for detecting a core muscle contraction in conjunction with the identified qualifying movement, a means for discriminating between a core muscle contraction and no core muscle contraction in conjunction with the identified qualifying movement, and a means to provide feedback to the user.

Preferably, the means for identifying the qualifying movement further comprises identifying at least one of a protected movement, and an unprotected movement. Identifying the protected movement comprises identifying a core muscle contraction of the user during the qualifying movement when stress is placed on the user's lumbo sacral junction. And identifying the unprotected movement comprises identifying inadequate or no core muscle contraction of the user during the qualifying movement when stress is placed on the user's lumbo sacral junction. In additional embodiments, the means for identifying the qualifying movement further comprises identifying at least one of standing from a seated position, sitting from a standing position, rotating to the left or right while standing, removing a carry-on load from an overhead bin in an airplane, lifting groceries out of a car trunk, serving or spiking a volleyball, and stabilizing a golf putting stroke.

Alternatively, the identification of a qualifying movement comprises identifying a movement of the user's body wherein the core muscle contraction would be beneficial to the user. Further, preferably the system includes a means to utilize an exercise application and a means to identify when the core should be contracted in relation to other movement(s) via image on a display, audible instruction, or video. Based on identified core contractions and other movements, an embodiment includes a means to calculate, store and report a core score over a pre-programmed period of time.

Another embodiment includes a device for assisting in the development of a user's core muscles, the device comprising: a single or plurality of sensors, and a single or plurality of signal processors. The single or plurality of sensors is further coupled with/to the single or plurality of signal processors. Further, the sensors coupled with the signal processors comprise means for detecting a qualifying movement and a core contraction, and further for detecting a timing relationship between the detected qualifying movement and core contraction, and for determining if the movement is a protected qualifying movement or an unprotected qualifying movement. The device further comprises means for communicating feedback to a wearer or user.

Preferably the device can provide real-time feedback, and additionally comprises a force sensing resistor (FSR) to identify the core contraction. Yet additionally, the device comprises an accelerometer or gyro to identify the qualifying movement and also comprises a means to communicate over a network with a PC, a smart phone, or a hand held device, thus providing feedback to the user.

According to an embodiment, the device can be utilized to aid in a personal workout session with or without a trainer. The device may communicate with a PC, video, or user hand held device such as a smart phone allowing the user to self-teach or allowing the device to communicate with a personal trainer or supervisor.

Alternatively, an additional wrist wearable device comprising means to communicate with the single or plurality of sensors and the said single or plurality of signal processors enables monitoring of the core and further monitoring of rotation of the user's hips. Further, the wrist wearable device combines monitoring of wrist movement and turn of the user's hips, wherein the coordination of the body turn and movement of the wrists may be optimized for a type of athletic movement. Thus, different types of athletic movements such as in golf, tennis, baseball, or volleyball can be programmed into the wrist and waist wearable devices.

An ideal embodiment includes a wearable device for assisting in the development of core muscle usage, comprising: a means to detect contraction of user's core muscles, a means to communicate with an external device, a means to provide measurable metrics, and a means to provide immediate feedback to improve the user's core muscle usage.

Embodiments disclosed comprise methods and systems that develop procedural memory for applications that use the core as a part of a more complex movement and that provide the user with additional information to improve the performance of another activity. For example, an embodiment comprises a system that monitors the core to promote core contraction support while the user is performing a golf putting stroke. While the core is being monitored, one or more hands may be monitored and feedback provided to encourage a pendulum like movement of the hands that may be desirable in a putting stroke in order to improve the putting stroke. Alternate embodiments comprise systems and methods wherein promoting core contraction support is not the primary procedural memory development objective. Rather, the development of procedural memory for other body movements may be the objective. For example, hand movements may be monitored and scored against movement targets or tracked and displayed on a monitoring device in order to provide immediate feedback in the form of a performance score or visual feedback to evaluate specific movements or movement characteristics.

A preferred embodiment includes a system comprising a wearable portable device and a computing device comprising instructions encoded thereon which instructions cause the computing device to receive real time feedback from the wearable portable device. The instructions further cause the computing and portable devices to promote use of the core (muscles) to support regular, every day movements such as moving from a sitting to standing position, as well as specific fitness, strength training, and athletic movements. Preferably, the computing device is a hand held device that comprises means to promote core contraction support. Preferred embodiments can be used throughout the day and night for continuous training including during and after training sessions for in situ development, and provide measurable metrics (scores) to monitor progress of core contraction support to the user as well as health care providers, trainers, and coaches. Software may run on a smart phone, electronic pad, or PC and may interact in real time with the portable device for training, teaching, and coaching. Additionally, encoded instructions may cause the devices to provide direct feedback and/or image or video feedback to a display, to monitor and improve training and athletic movements. Preferred embodiments allow effective development of core contraction support in users of all ages including children; and further allow, in a pain management program reducing or ideally, protecting a user from lower-back pain and other body aches as well as a pro-active health regime to utilize core support in daily activities. Preferably embodiments allow for a tighter and fitter abdominal area.

An embodiment includes a method for development of procedural memory for core support before and during qualifying movements, the method comprising: identifying qualifying movement or movements, identifying a core contraction in the identified qualifying movement or movements, discriminating between a protected and unprotected qualifying movement, and providing feedback based on the said discriminating, enabling a user to develop their procedural memory.

An alternate embodiment includes a method for development of procedural memory for core based support, comprising, via a single or plurality or sensors coupled with a single or plurality of signal processors, detecting a qualifying movement and a core contraction, detecting a timing relationship between the detected qualifying movement and core contraction, and determining if the movement is a protected qualifying movement or an unprotected qualifying movement. Further included in the method is communication to a PC, smart phone, or other portable device informing the user of a correct or incorrect, warranted or unwarranted core contraction, and a recommendation thereof.

An alternate embodiment includes a wearable, computer aided device for promoting core muscle usage, comprising a means to detect contraction of wearer's or user's core muscles wherein contraction results in an inward, outward, or neutral movement of the core, a means to communicate with an external device, a means to provide measurable metrics to monitor progress of core contraction support, and a means to provide direct feedback to the external computing device to monitor and improve the wearer's core muscles' activity or movement to activate the wearer's use of their core muscles.

A single or plurality of sensors in the device detects user core muscle contraction. Alternatively user core muscle contraction is detected using a single or plurality of force-sensing resistors. When force sensing resistors are used, an additional embodiment includes a sensor bumper coupled on one side to the user's core muscles and to the other side, the force sensing resistor.

Several embodiments of the device comprise a belt or article of clothing which when worn by the user, places the device substantially in contact with the user's core muscles. The belt or article of clothing is preferably partially elastic. Ideally, the sensor bumper is replaceable and comprises one or more height options to accommodate the user's body firmness.

Detecting contraction of the user's core muscles further comprises detecting at least one of an inward, outward and neutral movement of the area of the core being monitored. The single or plurality of sensors further comprise a means to detect movement of the device away from or toward the core, and accordingly identify the core contraction that results in an inward, outward or neutral movement of the core.

Some Core Muscle Basics

FIG. 1a illustrates a basic human skeleton with the spine and pelvis identified. The spinal cord is a tubular bundle of nerve tissue extending from the brain to the lower torso and legs. The spinal cord is housed inside the spine. The spine connects to the pelvis through the sacroiliac joint. As the torso rotates or the body moves up and down as a subject stands or sits, stress is placed on this region of the spine-pelvis connection also known as the lumbo-sacral junction.

Some of the core muscles together with the organs fill and wrap around the area of the lower ribs down to the pelvis. The core muscles include a large number of muscles and muscle groups including the transverses abdominus, multifidus, pelvic floor, diaphragm, quadrates lumborum, internal and external obliques, rectus abdominus, erector spinae, latissimus-dorsi, glueusmaximus, and trapezius. The so-called inner unit muscles of the core include the multifidus, pelvic floor, and diaphragm illustrated in FIG. 1b and the transverses abdominus which wraps around the torso like a corset in FIG. 1c. The four muscles in the inner unit generally work together so that when one muscle contracts, they all four contract.

While the core includes a large number of muscles, the inner unit grouping may be considered the primary grouping to support the lumbo-sacral junction. They include the deepest of the core muscles and fill the cavity around the lumbo-sacral junction in a way that they are often considered the most foundational. As different physical loads are placed on the body or during specific types of movements, it may be desirable to recruit some of the other muscles as well. Due to the foundational role in lumbo-sacral junction support, unless otherwise specified, core will generally refer to the inner unit group of the core muscles throughout this document. Once a person becomes proficient at utilizing these muscles during basic movements, that person is generally able to easily recruit additional muscles of the core as load increases or as more complex movements may demand. Since many of the core muscles co-contract, other muscles of the core may also be used for monitoring core contractions.

When the core is properly contracted, the area below the waist under the navel and over the groin between the thighs may become firm. As the core is contracted and this core area is made firm, the area may move outwards, inwards, or may maintain substantially the same position. The direction of movement of the core during a core contraction in either the outward or inward direction may be acceptable and beneficial. Net movement of this sensing area of the core may also be substantially neutral while the core is contracted and be acceptable and beneficial. Some users and some instructors of core usage may prefer to target a movement in one direction over another. In this document, in order to facilitate illustration we will generally assume the movement due to contraction of the core is outward. We will also consider the case where the core simply gets firm and movement is substantially neutral. Embodiments disclose applications comprising means to detect contraction of the core wherein contraction results in an inward, outward, or neutral movement of the core. A number of approaches for sensing a core contraction will be described.

One embodiment comprises a sensor or sensors to monitor both, movements of the body and contraction of the core. Since the core is comprised of a large number of muscles, there are a large number of locations that may be used to monitor the core. The choice of location or locations may depend upon the type of sensors used; a convenient means to attach a device to monitor core contraction from the location, and the usefulness of the data that can be derived from the location.

Basic Operation of the Device for Developing Procedural Memory for Core Contraction Let us define a Qualifying Movement as a movement of the body for which a core contraction may be beneficial. Examples of qualifying movements may include standing from a seated position, sitting from a standing position, rotating to the left or right while standing, removing a carry-on from an overhead bin in an airplane, lifting groceries out of a car trunk, serving or spiking volleyball, and stabilizing golf putting stroke.

Let us define a Protected Movement as a qualifying movement in which the core is contracted throughout the substantial parts of the movement when stress is placed on the lumbo-sacral junction, providing support to the lumbo-sacral junction. In a protected movement, core contraction support is achieved. In other words, support for the lumbo-sacral junction is achieved through proper contraction of the core muscles in a protected movement. In some applications, a protected movement may be defined as one where the core is contracted before the start and after the end of a qualifying movement.

Let us define an Unprotected Movement as a qualifying movement where the core is not contracted or not adequately contracted throughout the movement.

An embodiment includes the following: identifying an unprotected movement of a user and communicating the identified unprotected movement to the said user. Communicating the said identified unprotected movement comprises communicating via at least one of a buzz, a chime, any alternate audible sound, tens zap, or any other simple or complex signaling method.

Alternate embodiments include controlling the communication signaling wherein if a core contraction is not received within a specified amount of time, the signal may time out and stop. Further, if a core contraction is identified, the signal may be caused to stop. Additionally, for some Unprotected Movements, the signal may stop only after a core contraction is identified following a momentary cease of all substantial movement.

Protected Movements may be identified more precisely, depending on different qualifiers. For example:

Protected Movement (generic): A qualifying movement in which the core is contracted at the moment of the start of the qualifying movement and/or throughout the substantial parts of the movement where stress is placed on the lumbo-sacral junction.

Protected Movement with Dedicated Core Contraction: A qualifying movement in which the core is contracted inside a look-back window which is a time window preceding the start of the qualifying movement and throughout the substantial parts of the movement where stress is placed on the lumbo-sacral junction. In this case, a deliberate and dedicated core contraction is performed for each individual qualifying movement.

The device may not necessarily anticipate a qualifying movement and signal to the user before a movement is performed. Instead, it may help train the brain-body system to anticipate qualifying movements and protect them accordingly by providing immediate feedback when the core is not used during a qualifying movement. Through a pattern of monitoring body movements and core contractions and providing immediate feedback over an extended period of time, the desired outcome of procedural memory for core support may be developed.

The device may not identify every qualifying movement, particularly if they are spaced very closely in time to one another. The device may be optimized to minimize false positive identification of qualifying movements, and correctly identify the majority of qualifying movements. Accuracy from the perspective of long-term average is in accordance with the objective of developing the practice of proper and consistent core usage.

Figure 2:
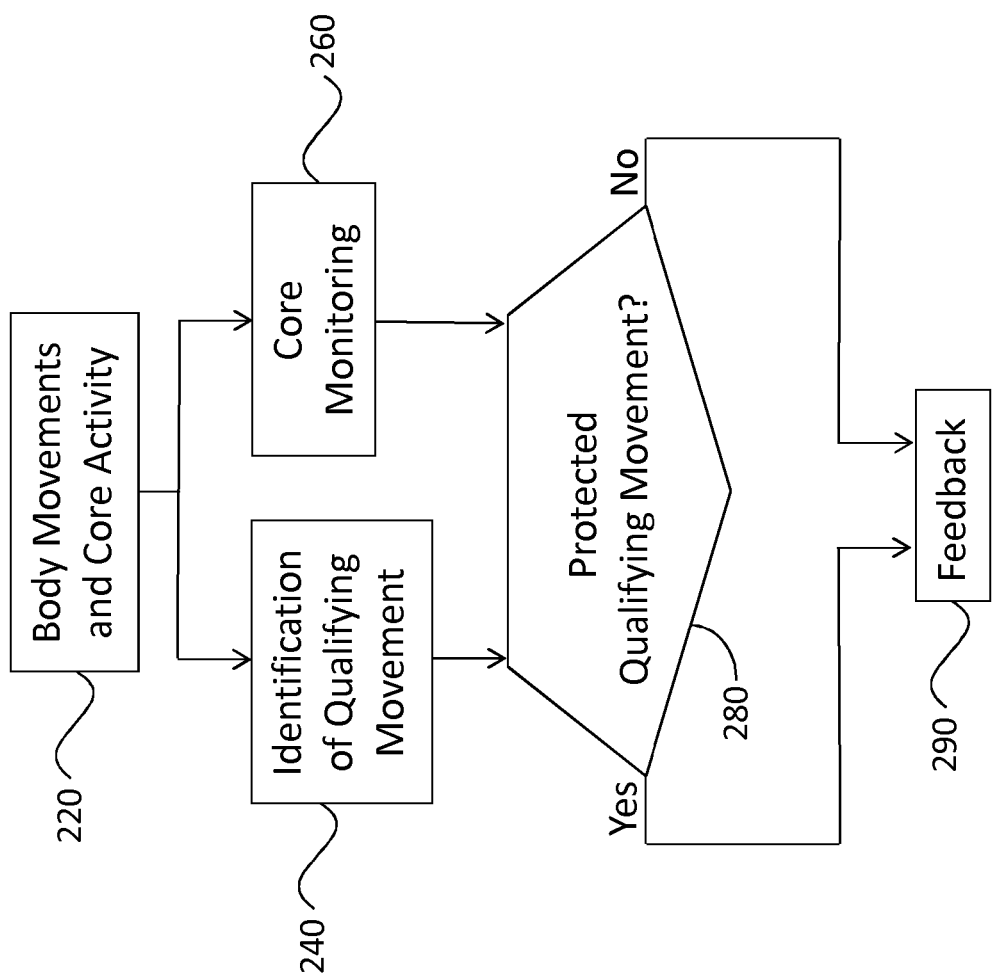
FIG. 2 illustrates a high level block diagram of an embodiment of a device to develop procedural memory for effective use and proper timing of core support.
Figure 3B:
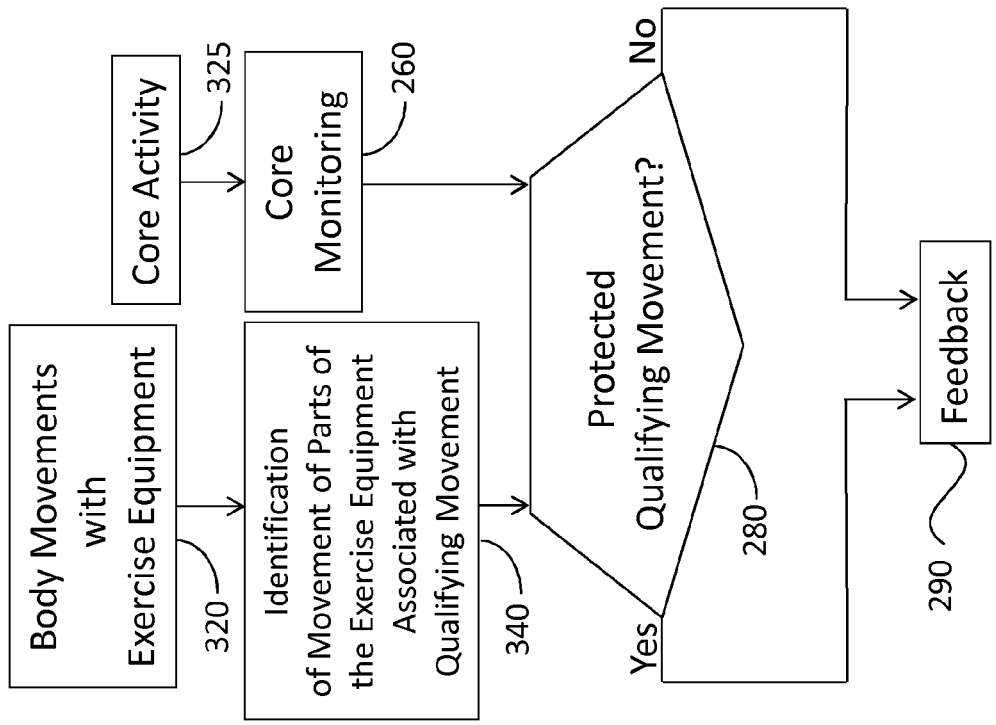
FIG. 3b illustrates the association between movements of parts of the exercise equipment and a Qualifying Movement for developing core support during exercises with exercise equipment.
Figure 3A:
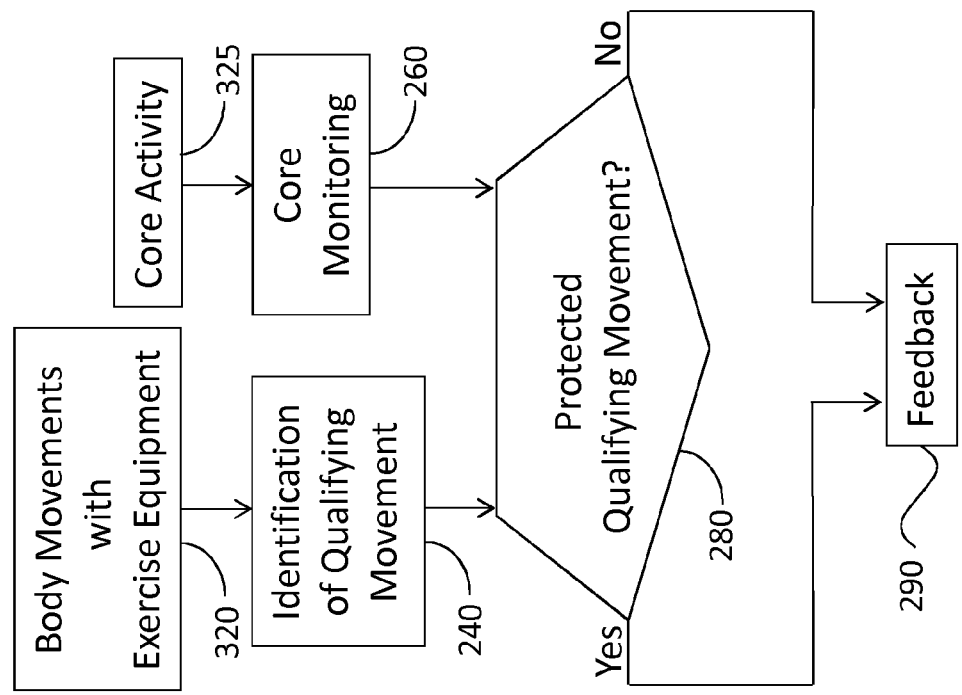
FIG. 3a illustrates a high level block diagram of an embodiment of a system to develop procedural memory for effective use and proper timing of core support during exercises with exercise equipment.
Figure 4A:
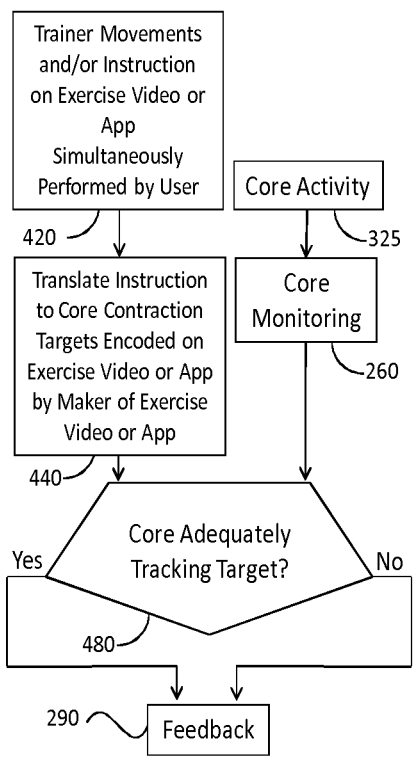
FIG. 4a illustrates a high level block diagram of an embodiment of a system for developing core usage and support with a video or app where the core activity is compared with a target core activity including elements such as contraction intensity, timing, and movement of the monitored core region inwards, outwards, or with little or no movement at all.
Figure 4B:
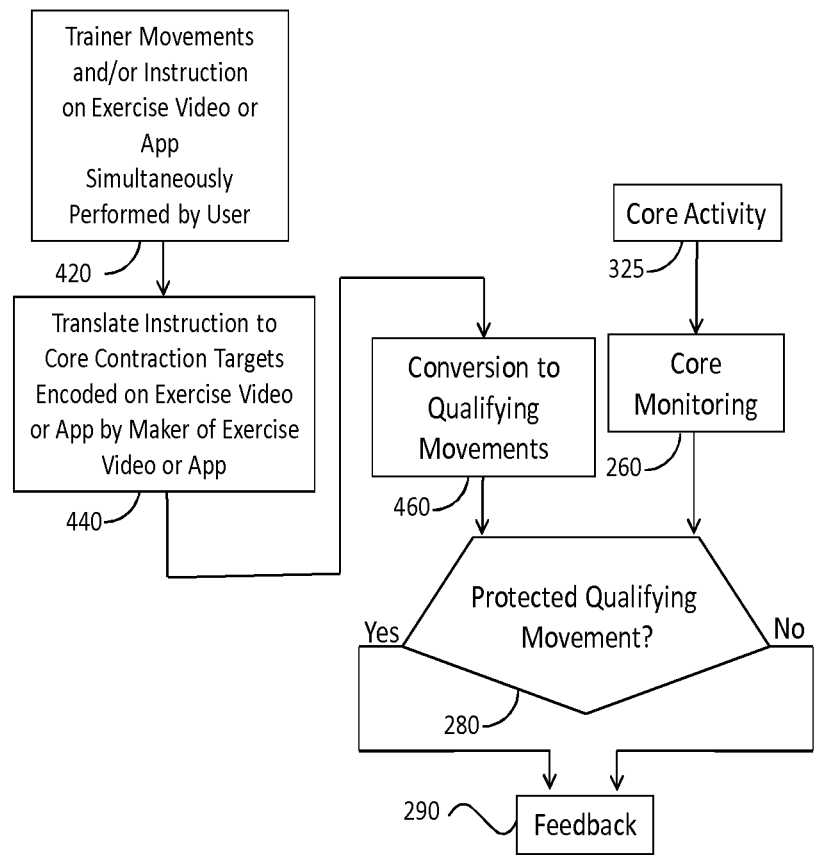
FIG. 4b illustrates the high level block diagram of FIG. 4a wherein target core activity is translated into qualifying movements and processed similarly as qualifying movements.
Figure 5A:
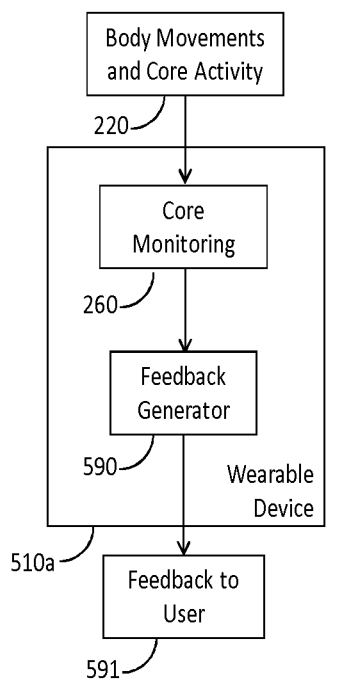
FIG. 5a illustrates a high level simplified block diagram of an embodiment for identifying core contractions and providing feedback to the user.
Figure 5B:
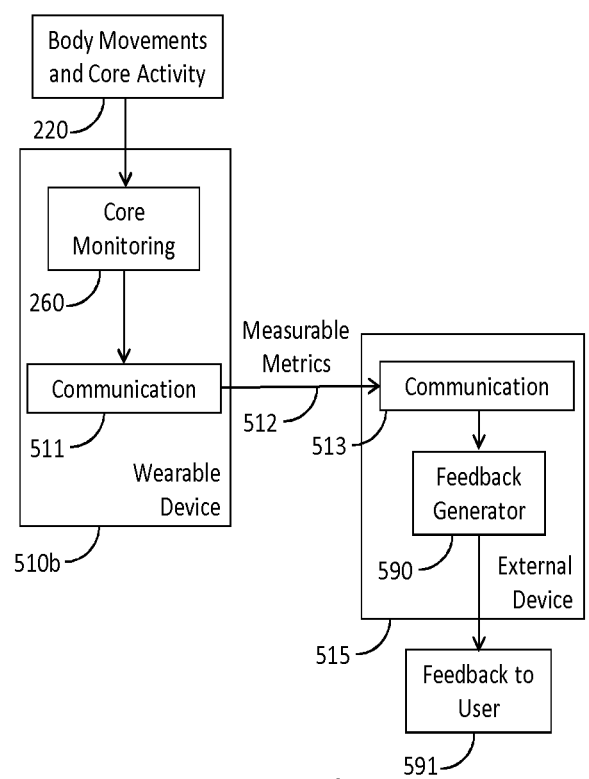
FIG. 5b illustrates a high level simplified block diagram of an embodiment for identifying core contractions and providing feedback to the user utilizing an external device.
Figure 6B:
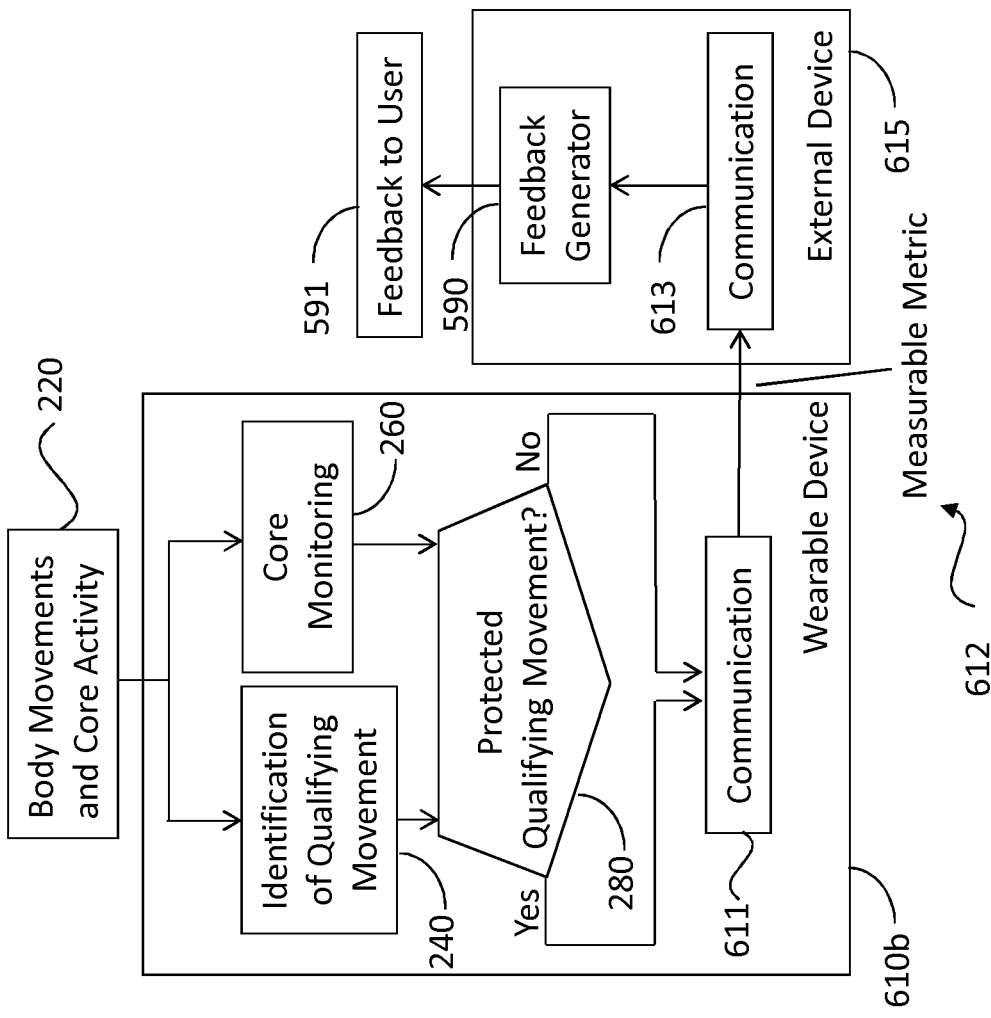
FIG. 6b illustrates the device of FIG. 6a configured to provide feedback through an external device.
Figure 6A:
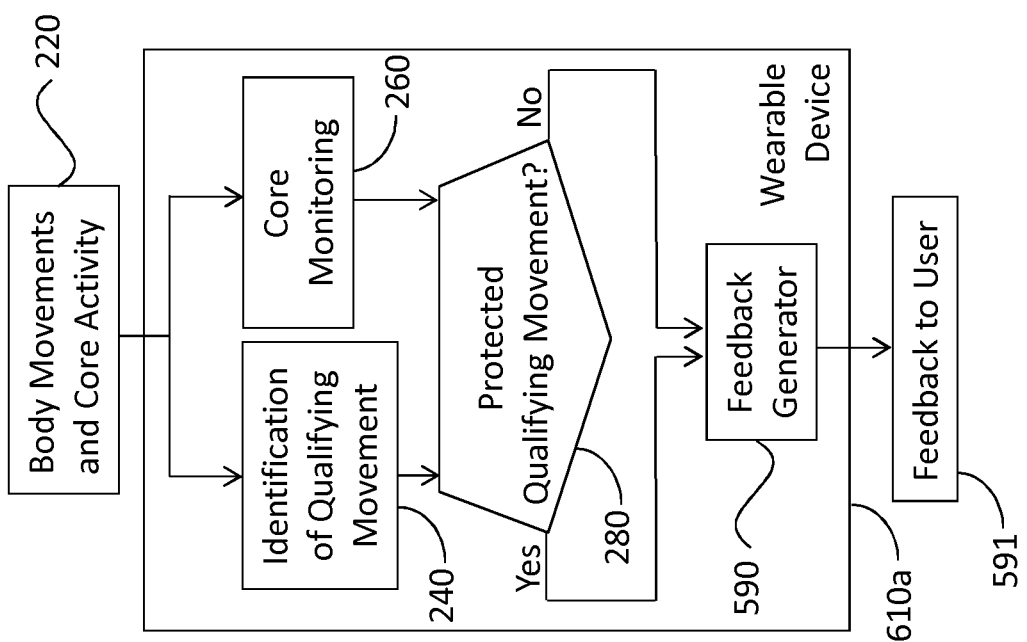
FIG. 6a illustrates a high level view of the signal processing blocks of an embodiment of a device to develop procedural memory for effective use and proper timing of core support.
Figure 7A:
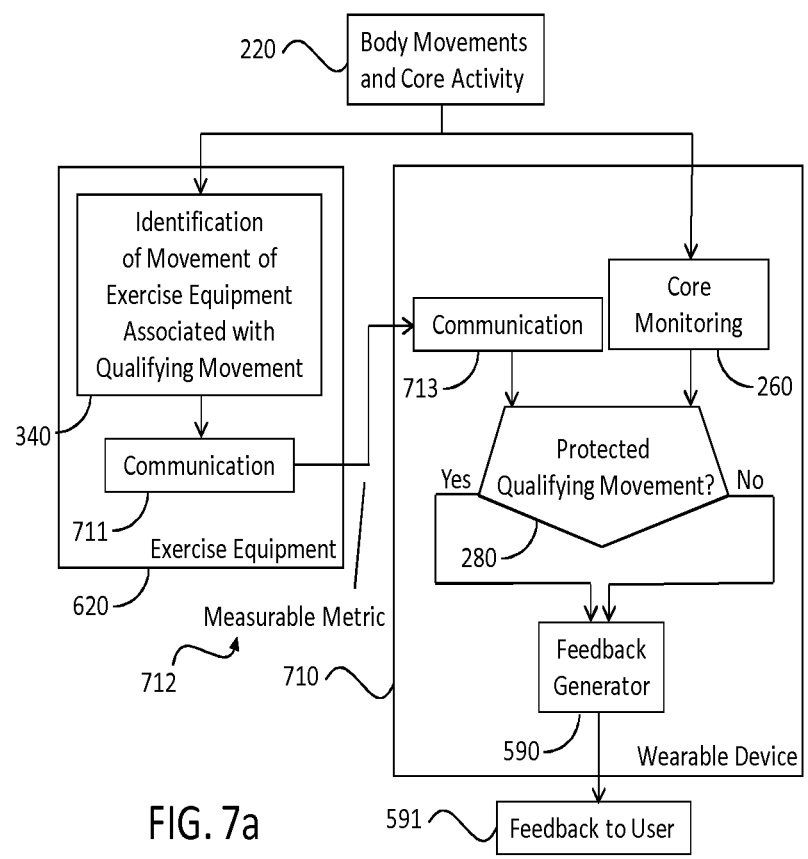
FIG. 7a illustrates a high level view of the signal processing blocks of an embodiment of a system to develop procedural memory for effective use and proper timing of core support with exercise equipment.
Figure 7B:
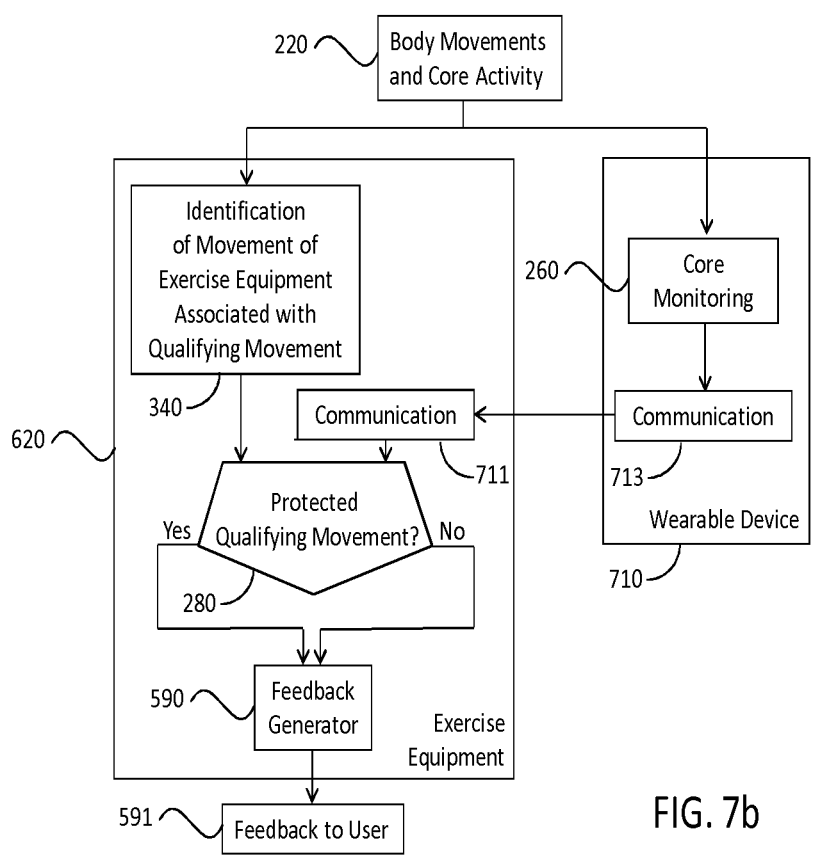
FIG. 7b illustrates the system of FIG. 7a configured to provide feedback through a device on the exercise equipment.
Figure 8:
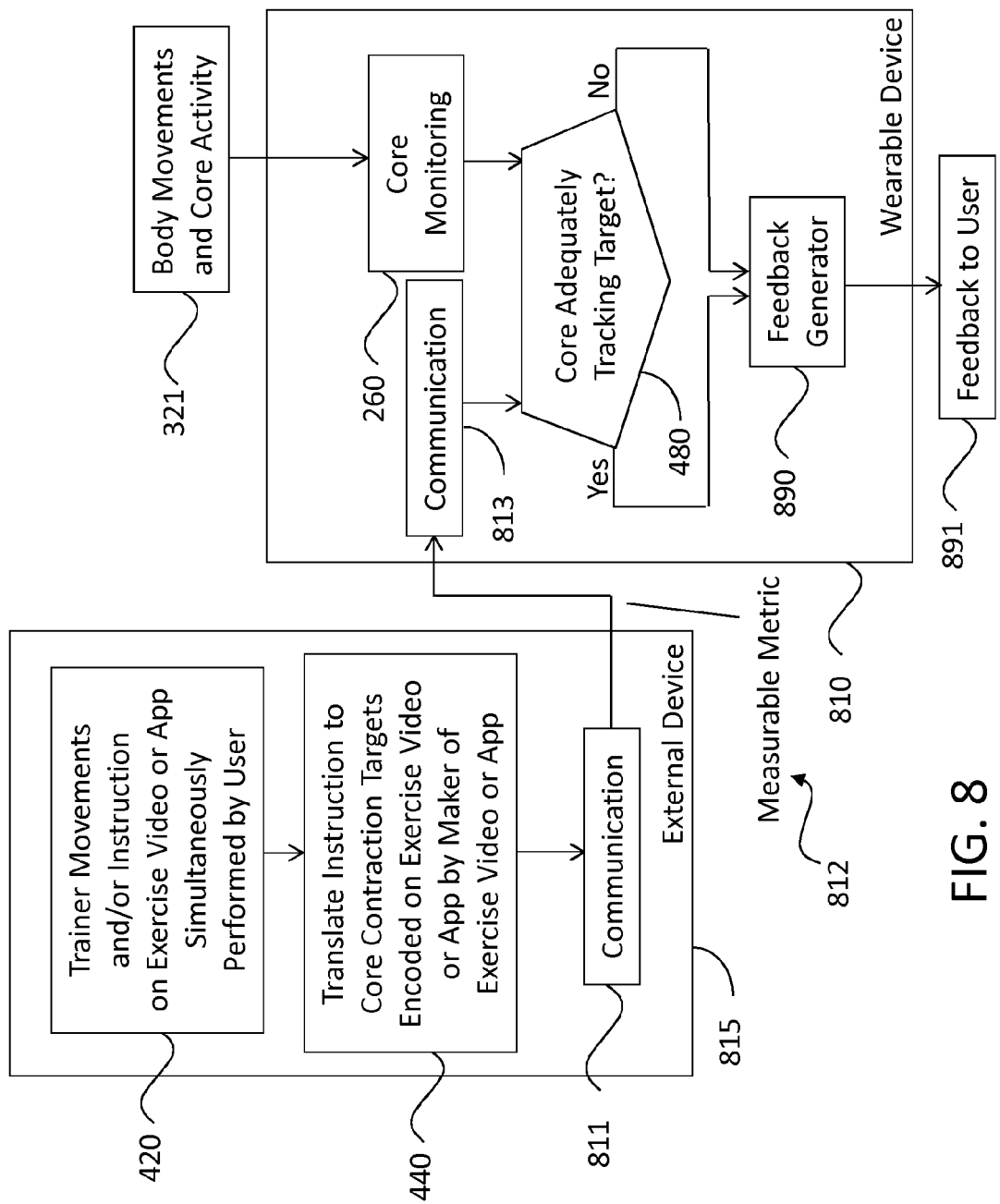
FIG. 8 illustrates a high level view of the signal processing blocks of an embodiment of a system for teaching and developing core usage and support with a video or app wherein the core activity is compared with a target core activity including elements such as contraction intensity, timing, and movement of the monitored core region inwards or outwards, or a core contraction without movement.
Figure 9:
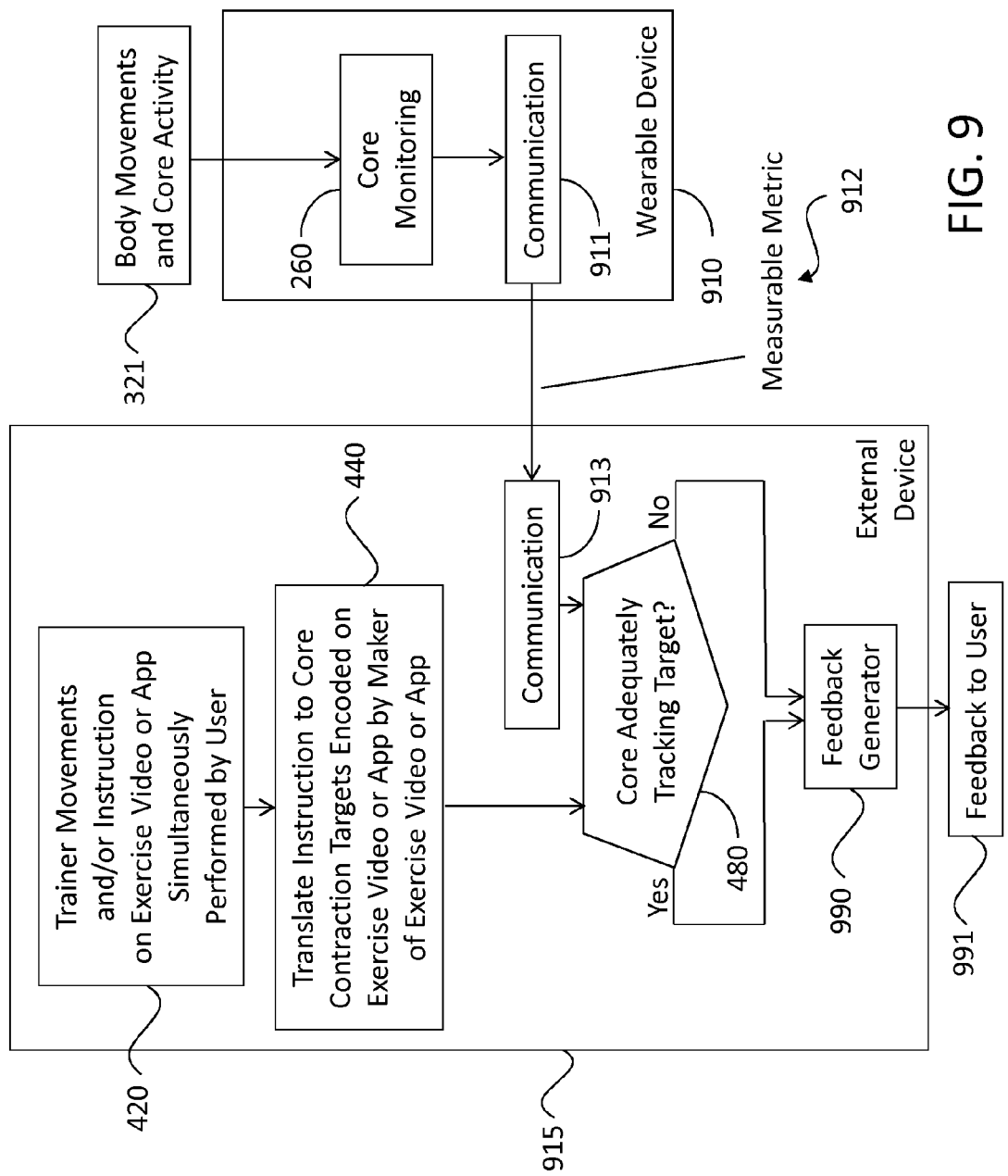
FIG. 9 illustrates the high level block diagram of FIG. 8 wherein the comparison between the user's core activity and the target core activity as well as feedback is performed on the external device.

Embodiments disclosed include a software component to be described later that includes diagrammed, animated, or video exercises running on a portable handheld device such as a smart phone, electronic pad, or dedicated device, or a PC. The combination of the exercises and use of the device throughout the day may work synergistically to promote the development of procedural memory for core support. FIG. 2 illustrates a high level block diagram of an embodiment of a device to develop procedural memory for effective use and proper timing of core support. FIG. 3*a* illustrates a high level block diagram of an embodiment of a system to develop procedural memory for effective use and proper timing of core support during exercises with exercise equipment. FIG. 3*b* illustrates the association between movements of parts of the exercise equipment and a Qualifying Movement for developing core support during exercises with exercise equipment. FIG. 4*a* illustrates a high level block diagram of an embodiment of a system for developing core usage and support with a video or app where the core activity is compared with a target core activity including elements such as contraction intensity, timing, and movement of the monitored core region inwards, outwards, or with little or no movement at all. FIG. 4*b* illustrates the high level block diagram of FIG. 4*a* wherein target core activity is translated into qualifying movements and processed similarly as qualifying movements. FIG. 5*a* illustrates a high level simplified block diagram of an embodiment for identifying core contractions and providing feedback to the user. FIG. 5*b* illustrates a high level simplified block diagram of an embodiment for identifying core contractions and providing feedback to the user utilizing an external device. FIG. 6*a* illustrates a high level view of the signal processing blocks of an embodiment of a device to develop procedural memory for effective use and proper timing of core support. FIG. 6*b* illustrates the device of FIG. 6*a* configured to provide feedback through an external device. FIG. 7*a* illustrates a high level view of the signal processing blocks of an embodiment of a system to develop procedural memory for effective use and proper timing of core support with exercise equipment. FIG. 7*b* illustrates the system of FIG. 7*a* configured to provide feedback through a device on the exercise equipment. FIG. 8 illustrates a high level view of the signal processing blocks of an embodiment of a system for teaching and developing core usage and support with a video or app wherein the core activity is compared with a target core activity including elements such as contraction intensity, timing, and movement of the monitored core region inwards or outwards, or a core contraction without movement. FIG. 9 illustrates the high level block diagram of FIG. 8 wherein the comparison between the user's core activity and the target core activity as well as feedback is performed on the external device.

Device Description

Many embodiments of the inventive system may utilize a device with inventive aspects that will now be described.

An important design objective is to allow the device to be made at a relatively low cost. To this end, the use of widely used components such as sensors and electronics commonly used in high volume devices such as cell phones and electronic pads is emphasized. However, the use of components with higher accuracy and cost may also be used for some applications. Designs using higher accuracy components may have different implementation configurations than described in this document but may also be contemplated by this invention disclosure.

An embodiment includes a sensor or sensors comprising means to identify qualifying movements. Upon identification of a qualifying movement, the disclosed embodiment further comprises means to determine whether or not the core had been contracted at or near the start and through at least part of the duration of the qualifying movement where stresses on the lumbo-sacral junction may be above a threshold. If the indication is that the core was not contracted, then the user is notified that an opportunity to use their core was missed. If the indication is that the core was appropriately contracted for the qualifying movement, then the user may not be notified. Alternatively, a notification of core contraction, or specific notifications informing the user of both core contractions and no core contractions may also be sent. Variations are possible, and likely, as would be apparent to a person having ordinary skill in the art. The notification signal may be generated by the device or sent to a user hand-held device or other computing device, wherein the user may be notified via a wired or wireless network, or via a wired or wireless communication means already invented or yet to be invented.

Another embodiment includes a sensor or sensors to identify qualifying movements. The embodiment further comprises means to define a look-back window. The look-back window is a finite window of time that may end before or around the time of the start of an identified qualifying movement. Some embodiments include encoded instructions comprised in a computer program wherein the instructions cause the embodiment to identify a qualifying movement defined partially by the velocity or acceleration of the user's body exceeding a threshold. The look-back window may end before or around the time the velocity or acceleration of the user's body exceeds the threshold. Alternatively, inertial navigation methods may be utilized to identify specific qualifying movements and the look-back window may end before or around the time of the start of the specific qualifying movement. The disclosed embodiment can then be caused to determine whether or not the core had started a contraction inside the look-back window and if the core contraction was maintained through the start or some inclusive part of the qualifying movement. If the indication is that the core contraction did not meet the appropriate criteria for that particular qualifying movement, then the device may communicate to the user to notify the user that an opportunity to use their core was missed. If the indication is that the core contraction did meet the appropriate criteria, then the device may not communicate. The test for a qualifying movement with a dedicated core contraction may include many or all of these steps. Communicating to the user may comprise the embodiment signaling to the user, or communicating via a wired or wireless network means to an external device that may signal to the user.

FIG. 10a illustrates a high level simplified block diagram for the signal processing of one embodiment of the basic device. The user's Body Movements and Core Activity 220 are applied to one or more sensors in a Sensor(s) block 1100 contained in the device. The output(s) of this block may go to a Signal Processing block 1120 implementing signal processing algorithms which convert the data from the Sensor(s) block 1100 to detect movements of the body and contraction of the core. The output of the Signal Processing block 1120 is input to a Signaling Unit block 1500 that has a means such as a buzzer or a chime or other audible sound played through a speaker to communicate or signal a Feedback Signal 1550 to the user. Based on timing relationships between body movements and contraction of the core, the device may signal to the user when it may be or may have been beneficial to contract their core.

Preferred embodiments include an electronic memory comprised in a Memory block 1001 which in turn is coupled to the Signal Processing Block 1120 as shown in FIG. 10b. Signal processing functions comprising the look back window function can thus be expeditiously implemented. This memory may be used to store input samples from the sensors 1100, intermediate outputs of the Signal Processing block 1120, or outputs of the Signal Processing block 1120. The Memory block 1001 may not be shown explicitly on remaining figures but should be assumed to be present in each where it may be beneficial. Consider the following scenario: Ten sensors record 10-bit samples at 200 Hz. This requires 20,000 bits for one second of samples. Adding 20 bits at 200 Hz for timestamp requires a total of 24,000 bits for one second of data. Multiple megabit memory is readily available at low cost, enabling low cost solutions to store more than one second of sensor data and interim and output calculations to be stored in a sliding window of time. Other variations are also possible as would be apparent to a person having ordinary skill in the art.

Figure 10D:
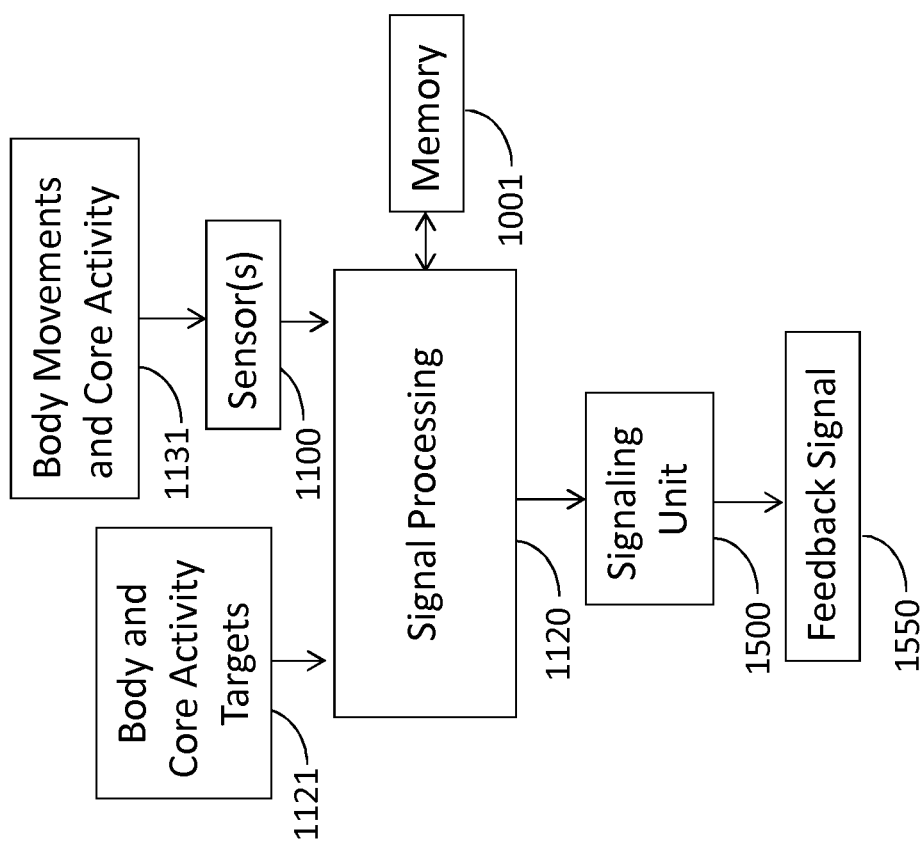
FIG. 10d illustrates a functional diagram including elements of an embodiment of a system for improving core usage where the targets for the core activity and body movements are provided, for example, through an exercise video or app.

FIG. 10d illustrates an embodiment in which data from the sensors 1100 is compared with Body and Core Activity Targets 1121. Body and core activity targets 1121 may be provided by an exercise video or app, and enable the performance of a user's body movements and core contraction to be compared against targets and feedback 1550 may be provided.

Preferred embodiments include a microprocessor or similar device, or alternatively, may connect to a computing device in order to run digital signal processing algorithms and/or control sequences. Preferably, the signal processing algorithms may operate on data from the sensors to identify movements of the body and contraction and release of the core. Additional embodiments may include signaling elements capable of providing a feedback signal to the user such as an electronic buzzer providing a buzz, a sound generator and speaker providing a chime or beep or other audible signal, or tens unit electrodes providing a tens unit zap. This may be used to signal to the user in order to highlight a missed opportunity to have contracted their core. Embodiments disclosed further may include power sources such one or more batteries for portable operation. At least one of the batteries may be rechargeable and at least one of the batteries may be used for battery backup. The batteries may be wirelessly charged, and alternatively, power may be wirelessly transmitted to the device in question.

An embodiment of the disclosed device may include one or more components for providing connectivity or communication to an external device such as a smart phone, electronic pad, or PC. An embodiment of the disclosed device may also include means for the charging of its batteries, wirelessly. Connectivity may also be used to provide connectivity or communication between devices when more than one device is present in the system. The devices may perform communication using a proprietary protocol or a commonly used protocol such as Bluetooth, Wi-Fi, USB, or Zig bee. If USB is used, the device may also use USB for charging a rechargeable battery.

In an alternate embodiment the microprocessor is comprised in a smart phone, electronic pad, or PC wherein the said smart phone, electronic pad, or PC run the digital signal processing algorithms or/and control sequences. Additional embodiments include electronic memory such as SRAM or Flash to store user data. This user data may include calibration results derived for a specific user. In addition, data may be stored, associated with a user's usage of their core as will be described. Further, embodiments disclosed may include a real time clock to keep track of time for time stamping user data.

The device may include one or more different types of sensors and/or sensor technologies for identifying qualifying movements and core contractions. For example, pressure sensors, accelerometers, and gyros or rotational sensors among others may be used. Sensing devices or materials configured to generate one or more output signals in response to applied pressure to a device or material, or movement of a device or material, or rotation of a device or material may be used. Sensing devices or materials configured to generate one or more output signals in response to the movement of two or more elements relative to one another as a result of applied pressure may be used. Such devices may be attached to the body in such a way that as for example, the core is contracted and the core section of the body moves, the elements also move allowing the core contraction to be sensed. Sensors capable of responding to physiological changes that occur in the body due to the contraction of muscles may be used.

Examples of sensor technologies that may be utilized include strain gage, capacitive, force resistive, magnetic, optical, and piezoelectric. Many of these may be utilized in more than one sensing configuration allowing them to be used in more than one sensor type. For example strain gage sensors may be utilized in both accelerometers and pressure sensors. Other sensors, sensor implementations, or sensor technologies may also be used. Sensor implementations may include any sensing technology that may respond to a direct stimulus or to the stimulus applied to a device or material attached to the sensing device that is attached to an interface that converts the stimulus to an electrical signal with a transfer relationship that is substantially monotonic over a useful range of stimulus.

A preferred embodiment of the device housing or package may comprise some or all of the following elements: a. All of the components which may include PCBs, sensors, sensing materials and peripherals, main battery, back-up battery, switches, power indicator, connectors such as USB, for example, may be packaged into a wearable device that may be comfortable when worn; b. Sensor or sensors capable of being coupled to user's muscles to enable effective monitoring of contraction and relaxation of one or a number of the core muscles; c. Means for enabling effective monitoring of body movements that may be identified as qualifying movements; d. Means for providing feedback to the user; e. Facility for putting onto the user and taking off the user; and f. Facility for cleaning, such as, for example, with soap and water. The housing may be manufactured using plastics, polycarbonate, acrylnitrile-butadiene-styrene (ABS), rubber, polymers, or another material, or combinations of materials.

Figure 13A:
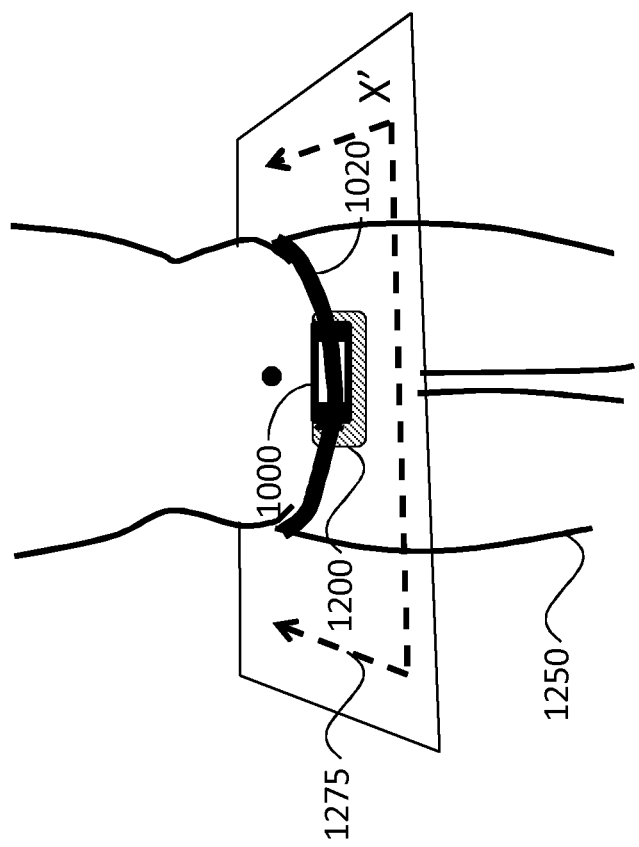
FIG. 13a illustrates the location for a cross section to illustrate forces and movement on the device when the user's core is contracted.

A preferred embodiment of device housing for the wearable device 1000 is shown in FIG. 11a. Referring to FIG. 11a, the width 1120 may be in the range between one and three inches, the length 1130 may be in the range between three and seven inches, and the thickness 1140 at the thickest location may be approximately one-half inch or less. Other shapes and sizes may be desirable depending on the application, as would be apparent to a person having ordinary skill in the art. A slight curve may be built into the housing to follow the natural curve of the body in the monitoring position as shown in FIG. 11b. The preferred embodiment may include hooks or clips 1020 having means to attach to a belt, underwear, undergarment, or other appropriate clothing as shown in FIG. 11b-FIG. 11d. Clips 1020 may use one or more magnets. In this example, the clip may slip on over a belt 1020 as shown in FIG. 11d. The preferred embodiment may be bendable such that when attached to the body, if the body shape changes contour due to muscles contracting or relaxing, the device may bend to follow the changing shape of the body. A preferred location 1200 for attaching the preferred embodiment against or near the body of a user 1250 is shown in FIG. 12a-FIG. 12c. Advantages of this location include: a. Device may contact the transverses abdominus through the skin and other muscles to assist in the identification of core contraction and relaxation; b. Device movement will follow torso movement for assisting in the identification of qualifying movements; c. Does not inhibit movement of the hands or legs; and d; May attach to belt worn on the waist which is natural for most users since wearing a belt or elastic around the waist is a generally common practice. FIG. 12b and FIG. 12c illustrate two locations near the waist where the device 1000 may be coupled to the preferred location 1200. In order to illustrate operation of core contraction sensing, refer to the cross section 1275 defined by the plane through the user's 1250 belt line in FIG. 13a and shown in FIG. 13b and FIG. 13c. FIG. 13b contains an outline of the user's core section 1255 in the region where the device is attached, the top view of the wearable device 1000, a belt shown with hatched lines 1020, clips 1010 onto the belt 1020, lines of force from the user's abdomen or core against the device shown as dotted vectors 1301a-1301c, and lines of force from the belt toward the user's abdomen or core shown against the device as dotted vectors 1302a-1302c. As the user contracts their core, the transverses abdominus will be contracted and may result in a change in the direction of force shown as an increase in the magnitude of vectors 1303a-1303c. Alternatively, if the user pulls in their core, i.e., moving area 1200 in toward the body, the magnitude of the vectors may decrease. Assuming the former, vectors 1304a-1304c will also increase. If the device package is designed to be flexible, a bend may occur in the package as shown in FIG. 13c due to the change of the shape of the surface of the abdominal section under the device. This bend may contribute to the identification of a core contraction in at least two ways utilizing sensors. First, sensors may be utilized to identify the bend in the device. And second, sensors may be placed at different positions in the device and the relative movement of the sensors with respect to each other may be used to assist in the identification of a core contraction. In addition, sensors may be used to detect the change in applied force on the device and may contribute to the identification of a core contraction. As described earlier, a number of sensor technologies and approaches may be utilized to identify a core contraction and relaxation. Different sensor technologies may be utilized both independently and in combination. Additionally, different sensing architectures may be utilized. Next, we will present how different sensors may be used to assist in the identification of a core contraction.

Figure 14B:
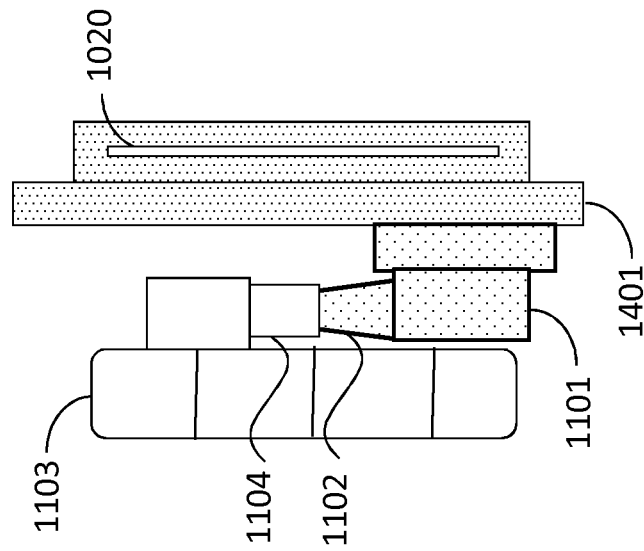
Figure 14A:
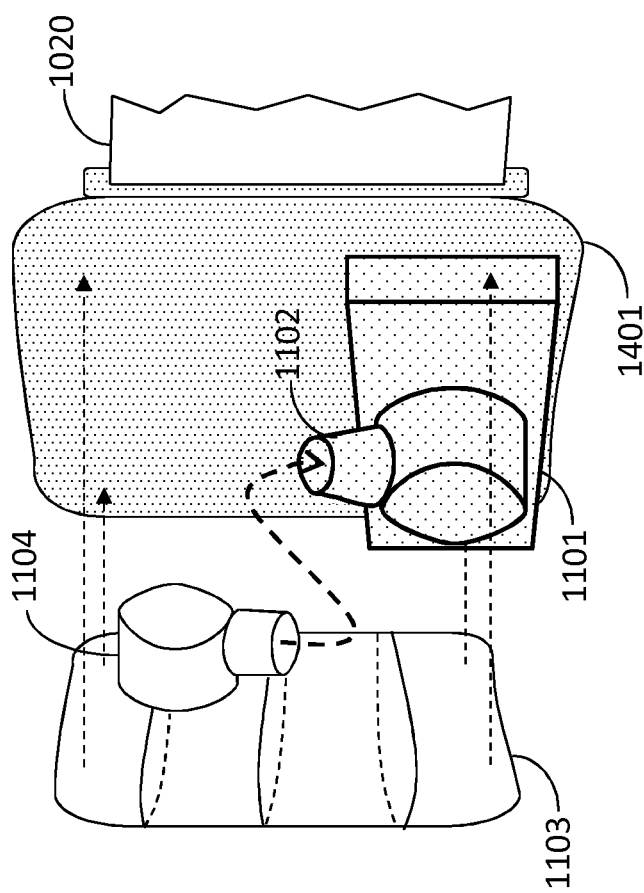
FIG. 14a illustrates the elements of a pressure sensor and a bladder onto which pressure from the may be applied.
Figure 15D:
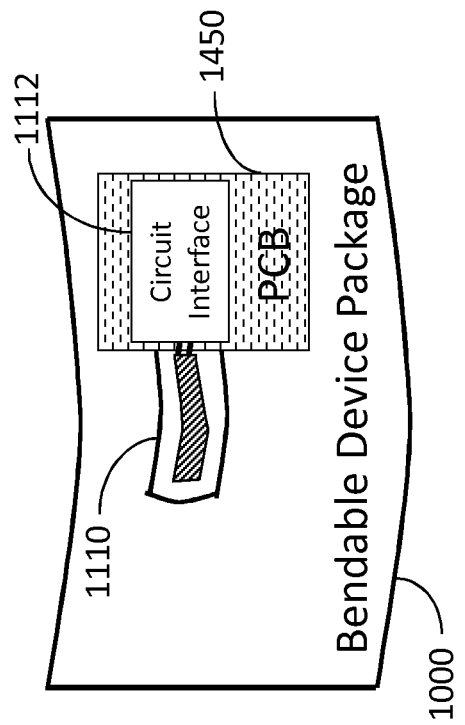
FIG. 15a-FIG. 15d illustrate the use of a strain gage sensor placed in a pliable or bendable package. As different forces are applied onto the device as a result of a core contraction, the package may bend from the relaxed state in FIG. 15a to different shapes shown in FIG. 15b and FIG. 15c.
Figure 15A:
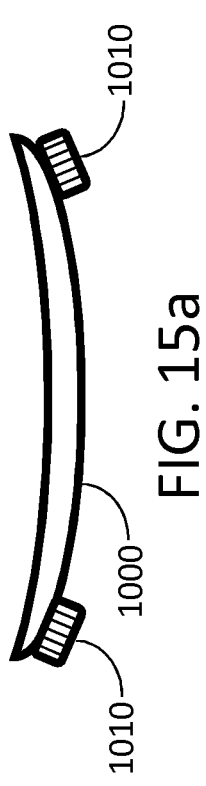
Figure 15B:
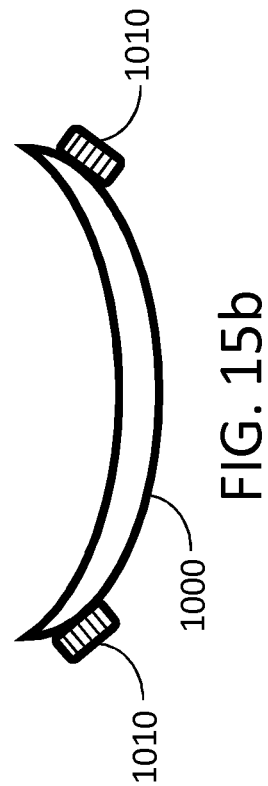
Figure 15C:
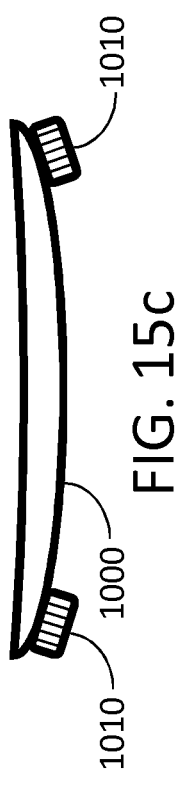

In one embodiment, one or more pressure sensors may be configured to detect changes in pressure on the wearable device, and this change in pressure may be utilized to assist in the identification of a core contraction. The increase in the pressure on the device due to the core contraction (as indicated by the increased vector magnitudes in FIG. 13c) may increase the applied force on the device that may be detected by pressure sensors or sensing material interfacing to pressure sensors. An example of the operation of a pressure sensor is shown in FIG. 14a. The pressure sensor 1101 has an intake port 1102. It is coupled to a bladder 1103 that has an outtake port 1104. The bladder may be manufactured out of rubber or vinyl or similar material. The coupling of the ports may form an airtight or liquid tight seal. The bladder 1103 may be filled with air, gas, liquid or other substance or combination of substances such that as external pressure is applied to the bladder 1103, the bladder communicates this change in pressure to the pressure sensor 1101. The combination of the pressure sensor and bladder may be connected to a portion of the wearable device and the wearable device may be attached to a belt as shown in FIG. 14a. A side view of the combination is shown in FIG. 14b. Additional packaging is required. The bladder 1103 couples to the user's core area. An output of the pressure sensor may be an electrical signal substantially monotonic with the applied pressure over a useful range of applied pressure. As the core is contracted and relaxed, this signal may be utilized to assist in the identification of said contraction.

Figure 18A:
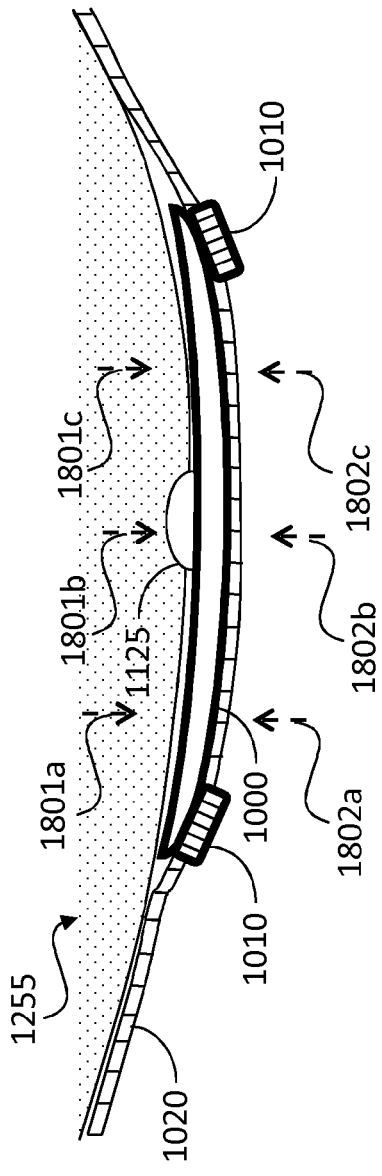
FIG. 18a illustrates a cross-section including the user's core section coupled to the device, wherein the device is being held to the user's core with an elastic belt and relative forces on either side of the device with the core in the relaxed state.
Figure 18B:
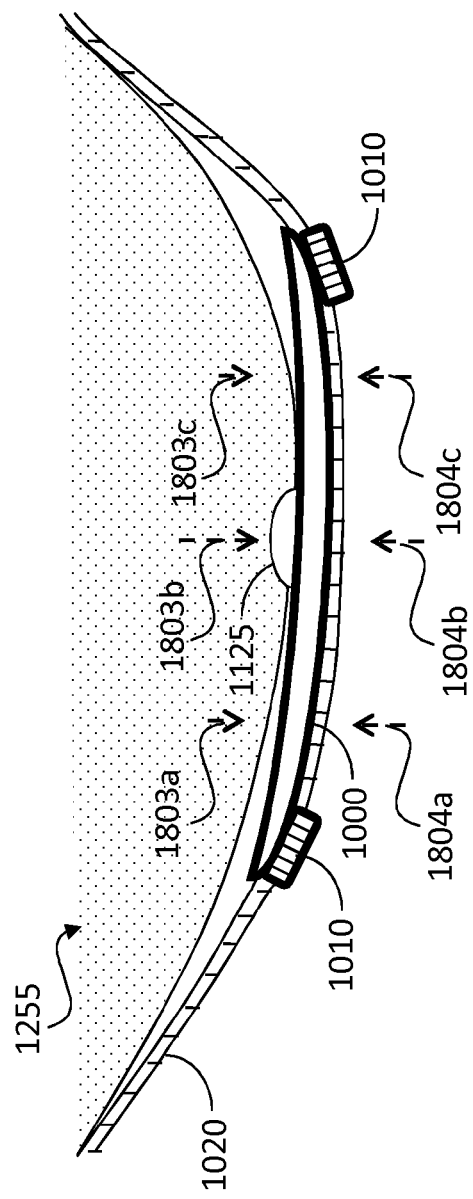
FIG. 18b illustrates the configuration of FIG. 18a and the change in forces on either side of the device with the core contracted. In particular, during a core contraction, the force on the sensor bumper from the user's core is emphasized.

In another embodiment, one or more sensors may be configured to detect movement of the wearable device 1000, and this movement may be utilized to assist in the detection of a core contraction. The resulting change of bend in the device in response to a core contraction shown in FIG. 13c may be sensed by appropriate movement sensors or sensor configured to sense movement or relative movement. For example, strain gage sensors may change their electrical conductivity when stretched or compressed. FIG. 15 shows a device utilizing strain gage technology. The housing may be pliable to enable bending in response to changes in the shape of the device in response to changes in the shape of the user's body to which it is connected as shown in FIG. 18a-FIG. 18c. FIG. 18a illustrates the package in a rest state with no external forces applied. FIG. 18b illustrates the package shape in response to the ends of the device being pulled toward the user. FIG. 18c illustrates the package shape in response to the ends of the device being pushed away from the user. A strain gage sensor 1110 may be attached to the pliable package as shown in FIG. 18d. As the device bends in response to a core contraction, the bend may be translated to stretching or contraction of the sensing material. The associated change in conductivity of the strain gage sensor 1110 may be sensed by an appropriate circuit in a Circuit Interface block 1112 that converts the movement into an electrical signal. This is one example of how movement may be detected utilizing sensors and how this may be utilized to assist in the identification of a core contraction.

Figure 16A:
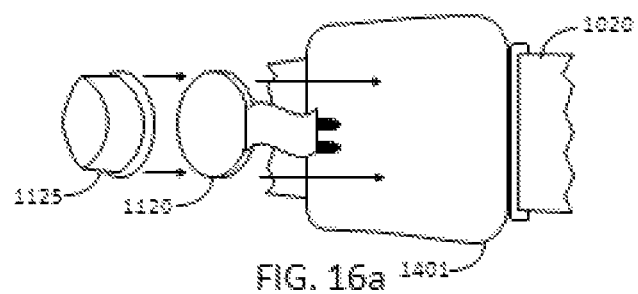
FIG. 16a illustrates an embodiment of the device utilizing a force sense resistor and a sensor bumper.
Figures 16B, 16C, 16D:
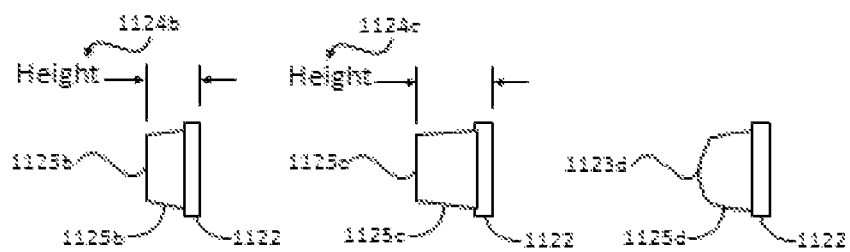
FIG. 16b-FIG. 16d illustrates some potential changeable features of the sensor bumper.

In another embodiment, one or more force sensing resistors (FSRs) 1120 may be configured to detect changes in force on the wearable device, and these changes in force may be utilized to assist in the detection of a core contraction. An FSR 1120 is a sensor that may be flat and come in different shapes such as round or rectangular, and that experiences substantially proportional changes in electrical resistance to applied force. The sensor bumper may be rubber or vinyl, plastic, polymer, or made of other suitable material or combination of materials. FIG. 16a illustrates the use of a FSR 1120 wherein the device is configured to have a protrusion referred to as a sensor bumper 1125. FIG. 16b-FIG. 16d illustrates different examples of the sensor bumper. Referring to the illustration of FIG. 16b, the sensor bumper has two ends: one end 1122 couples to the FSR 1120, while the other end 1123b couples to the user's core. To accommodate different body types, for example different amounts of body fat or body firmness, the sensor bumper may have different bumper heights. For example, height 1124c of the sensor bumper in FIG. 16c is greater than the height 1124b of the sensor bumper in FIG. 16b. The shape may also be modified to enhance comfort and sensitivity. For example, the ends of sensor bumpers 1125b and 1125c that couple to the user's core is substantially flat whereas the end 1123d of the sensor bumper in FIG. 16d is rounded, potentially providing a bit more comfort or perceived comfort.

A wearable device 1000 utilizing an FSR and a sensor bumper are illustrated in FIG. 17. The bumper may be located at or near the center of the device in a location to efficiently couple to the target sensing area of the user's core 1200. FIG. 17b illustrates a view from the user's core to the device 1000 and FIG. 17c illustrates a side view. FIG. 18 illustrates the forces on wearable device 1000 utilizing an FSR and sensor bumper. FIG. 18a and FIG. 18b illustrate the forces with the user's core relaxed and contracted, respectively. When the core is relaxed, the area of the body under the device is in a soft relaxed state and the pressure of the body onto the device may be somewhat evenly distributed across the device as shown in FIG. 18a. When the core is contracted, the area of the body under the device may firm. As the core firms, the force on the sensor bumper may increase and the force in the area away from the bumper may decrease due to the firmed core pressing preferentially on the protruding sensor bumper as shown in FIG. 18b. As noted in the figure, line 1803b representing force of the core onto the sensor bumper 1125 increases while lines 1803a and 1803c representing force away from the bumper may decrease as depicted for a moderate contraction of the core. One way to view this is as follows: since the sensor bumper protrudes in the direction of the body, it is the first element to make contact with the body and subsequently the part of the device that may receive the most force as the core is contracted.

The height and shape of a sensor bumper or protrusion utilized in a design may be a function of the sensors and sensing elements utilized, and the physical design of the device and desired sensitivity of the sensors. Comfort, ease of cleaning, as well as aesthetic issues contributes additional design considerations. The sensing element may be contained at least in part in the volume of the sensor bumper. The sensor bumper may itself substantially function as the sensing element. A sensor bumper may also be used with a bladder and a pressure sensor. A sensor bumper may be visible and protrude from a device package. Alternatively, a sensor bumper may be housed under a sheet of a pliable material. A device utilizing a sensor bumper may assist in the identification of a core contraction in which the core becomes firm with substantially little movement.

Figure 19C:
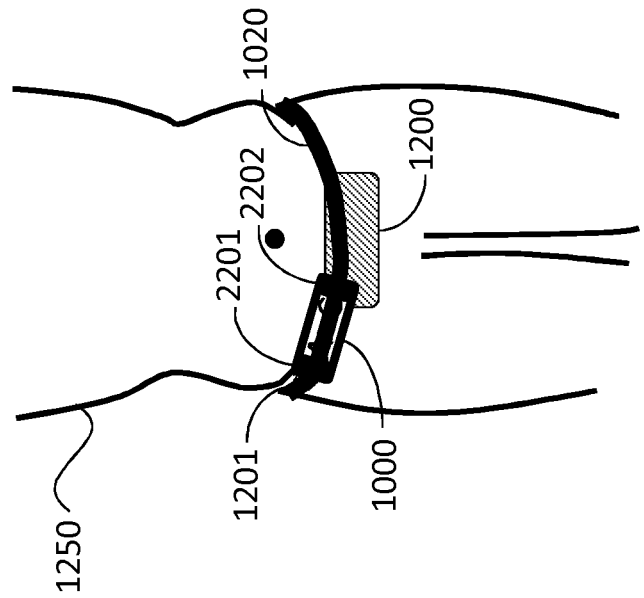
FIG. 19c illustrates an embodiment of the device configured for differential sensing placed on a user in an effective location using a belt.
Figure 19B:
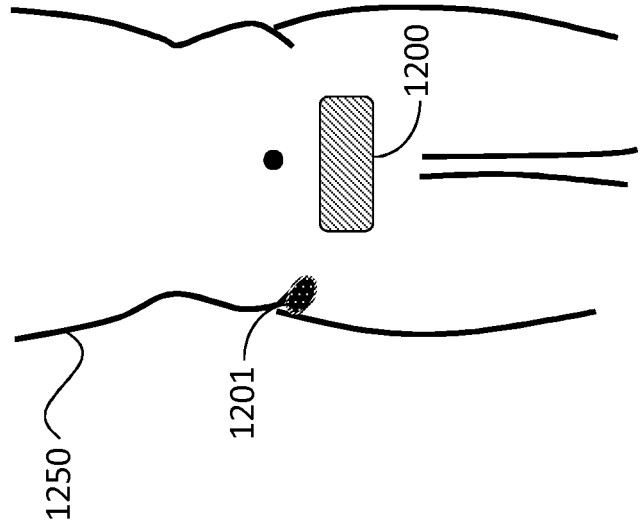
FIG. 19b illustrates a suitable embodiment of an effective location for differential sensing.
Figure 19A:
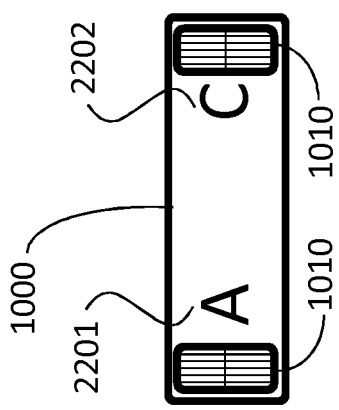
FIG. 19a illustrates an embodiment of the device configured for differential sensing.

In another embodiment, one or more accelerometers and/or gyros may be configured to detect changes in movement of the wearable device, and these changes in movement may be utilized to assist in the detection of a core contraction. One embodiment is illustrated in FIG. 19a wherein the device may be configured to have two independent sensing locations within a single device: an anchor sensing side demarcated by A 2201 and a core sensing side demarcated by C 2202. A device with this configuration may be packaged in a way that enables it to be worn near the waist with one end on or near the hip bone (protruding on either side of the front hip) and the other end on or near the preferred sensing location 1200 as shown in FIG. 19*b*. Let us refer to the sensor location on or near the hip bone as the anchor sensing position A 2201 and the sensor location on or near the preferred sensing location 1200 as the core sensing position C 2202. An example of the device being worn on a user with the anchor and core sensing positions appropriately situated are shown on the right of FIG. 19*c*. In some implementations, it may be desirable for the device to be housed in a pliable housing to facilitate bending of the device with the core in the preferred location.

In the configuration with two sensing locations, the difference in movement between anchor and core sensing positions may contain information to indicate contraction of the core. As such it is necessary to have two independent sensor groups and preferable to have two relatively independent sensing locations. FIG. 20*a* shows one configuration of two distinct sensor groups on one printed circuit board (PCB) 1451 and placed in the same package. Sensor Group 1 may be configured on the Anchor Sensing Side and Sensor Group 2 2521*a* on the Core Sensing Side. Assignment of one side as 2201 and the other as 2202 is arbitrary. FIG. 20*b* shows another configuration wherein each distinct sensor group is placed on a separate PCB 1452, 1453 connected by a cable. An alternative to this two PCB 1454, 1455 solution is shown in FIG. 20*c* where instead of a cable, the sensor groups communicate via a wireless connection. In both cases shown in FIG. 20*b* and FIG. 20*c*, both PCBs are contained in a single package. The figures suggest these housings are pliable or bendable. However, these inventive ideas may also be applied to housings that are neither pliable nor bendable. These concepts may easily be extended to include multi-package scenarios.

As described earlier, a number of sensor technologies and approaches may also be utilized to identify qualifying movements. Different sensor technologies may be utilized both independently and in combination. Additionally, different sensing architectures may be utilized. Accelerometers and gyros are widely used in consumer applications such as smart phones and gaming. This combination may be very effective for assisting in the identification of many qualifying movements. In one embodiment, the inventive wearable device 1000 may utilize at least one accelerometer and at least one gyro to assist in the identification of a qualifying movement.

In some implementations, the device may operate with one or more other devices in a multi-device system where the devices may have different features, sensors or sensor groups, sensor group configurations, shape, function, and manner of being attached on to or near the body. For example one device may be attached to the waist while another is attached to the wrist. The devices may have a capability to communicate with other devices in the system. At least one of the devices may have the capability to communicate with a handheld device or PC. Example applications utilizing multi-device capability are described later in this document.

Core Score

In addition to providing immediate feedback of core contraction support to the user, embodiments disclosed include a device that may also provide data to track progress for the user as well as their health care provider, fitness trainer, instructor, and/or coach. One example is the core score that is a measure of the percentage of correct contractions of the core to the opportunities where core contraction support would be beneficial. The core score is similar to a batting average in baseball where the batting average is 1000 times the number of hits divided by the number of at bats. Let us define the core score as:

Core Sore=(Number of Protected Movements/Number of Qualifying Movements)×1000

The core score can be averaged over a useful period such as a therapy session or day or week. Progress regarding proper use of the core can be accurately tracked and may be regularly reported to the user and/or their health care provider. The Score Keeper block that maintains the Core Score is shown in FIG. 10*c*. Multiplication of the aforementioned ratio by 1000 is arbitrary. Other factors including 1 (one) may be used.

Operation Example 1

Single Device—Single Sensor Group

In order to further illustrate operation of the inventive concepts, let us examine three operation examples. According to a first example embodiment, one sensor group (Single Sensor Group) is utilized in one device; according to a second example embodiment, two or more sensor groups (Multiple Sensor Group) are utilized in one device; and according to a third example embodiment, two or more devices (Multiple Device) are utilized and each device may contain one or multiple sensor groups. Other combinations may also be utilized as will be apparent to a person having ordinary skill in the art.

Preferred embodiments utilize signals received from all available sensors to maximize confidence in the identification of body movements and body movement sequences in order to identify specific types of movements such as qualifying movements and core contraction.

In Single Sensor Group implementations, a device may contain one group of sensors. The group of sensors may contain one or more sensors. More than one type of sensor may be utilized in a sensor group. A desirable combination of: a. Placement of the sensor group in the device; and b. Manner and location of attachment of the device onto or near the body may be selected to improve the information provided by the device to identify different body movements and body movement sequences that may include the identification of qualifying movements and core contraction. In the case where more than one sensor is utilized, the sensors are located in the device substantially in the same area. Due to the placement of the sensors inside the device and the manner and location the device is attached to or near the body, each of the sensors are subject to substantially the same or similar movement. Due to the difference in sensing technology, each of the sensors may provide a different response to a given body movement. Together, the different responses may be combined to increase the accuracy for identifying specific movements and movement sequences. In other words, the redundancy associated with multiple sensors experiencing substantially the same or similar movement may be used advantageously to increase detection confidence in identifying a given movement or movements. On the other hand, discrepancy may lower confidence in the identification process of a given movement. If the confidence in a detected movement reduces below some threshold, the detection of the particular movement may be thrown out or ignored.

The use of multiple sensors in a Single Sensor Group may increase the amount of available information and enable the device to make better movement identification decisions. In Single Sensor Group implementations, a single sensor group may be used to identify both qualifying movements and core contraction. Let us assume the device is attached near the waist on the preferred sensing area 1200.

Refer to FIG. 21*a*-FIG. 21*d* where a user 1250 is shown diagrammatically moving from a seated position to a standing position over a period of time of approximately 500 milliseconds. In these figures, the device is represented by a circle on or near the preferred position 1200. Three dimensions are defined as follows relative to the front of the user: X-dimension as going from right to left, the Y-dimension as going from down to up, and the Z-dimension as going from back to front as indicated in FIG. 21*a*.

FIG. 21*e* illustrates a plot of the location of the device in the y-dimension approximately every 20 milliseconds; i.e., a plot of the movement of the device upward. Near the start and end of the movement, the circles are close together indicating a relatively less movement. While toward the center of the movement, the circles are spaced further apart indicating a relatively faster movement.

FIG. 21*f* and FIG. 21*g* illustrate the velocity and acceleration of the device in the y-dimension over the period of time, respectively. The velocity starts and ends slowly with the peak velocity occurring near the center of the movement. The acceleration increases as the rate of change of velocity increases and the acceleration decreases as the rate of change of velocity decreases. The result is the positive peak acceleration as the user is in the first half of the movement, and a negative peak acceleration (or deceleration) in the second half of the movement as the user decelerates as the standing position is nearly reached. As the acceleration peaks in both positive and negative directions, the relative force on the lumbo-sacral junction is increased. Large peaks in the magnitude of acceleration or velocity indicate movements in which support of the core may be especially beneficial.

Let us consider an example to further illustrate operation of the device according to an embodiment. FIG. 22*a* illustrates the body position in the y-dimension. As the movement of the device location in the y-dimension changes by an amount greater than a programmed amount, for example 6 inches, and this movement is the predominant movement detected by the sensors with all other movements less than 10 percent of the 6 inches, this movement may be detected as a qualifying movement. The next step is accessing the memory storing the sensor data and processing this data to determine the timestamp of the start and end of the qualifying movement. Linear and non-linear signal processing may be utilized to determine these end points. The qualifying movement end points are shown in FIG. 22*b*. At some time period before the start of the qualifying movement, the end of a Look-Back Window 2610 may be established as shown in FIG. 22*c*. The look-back window duration may be fixed or context dependent. Context dependent refers to a variable element of an embodiment wherein depending on the nature of the qualifying movement, a longer or shorter look-back window may be desirable and utilized. If a core contraction is detected to begin inside the look-back window 2610 and remain contracted until the end of the qualifying movement, the movement may be considered a protected qualifying movement as indicated in FIG. 22*d*. If a core contraction is not detected to start inside the look-back window and continue until after the end of the qualifying movement, the movement may be considered an unprotected qualifying movement. An example of an unprotected qualifying movement is shown in FIG. 22*e*.

At least two additional requirements may be added. First, a protected movement may require that the core contraction sufficiently overlaps the qualifying movement in time to allow the core contraction to protect the lumbo-sacral junction from the stresses of the qualifying movement. Second, a protected movement may require that the core contraction begin inside the look-back window to encourage dedicated core contractions. For this reason, the look-back window may be several hundred milliseconds in duration. An accelerometer, pressure sensor, and/or gyro may be used as sensors to assist in the identification of qualifying movements. A preferred combination may include an accelerometer and gyro although other combinations of sensors may be utilized.

Through computer programming of the system, a protected qualifying movement for a novice or beginning user of the inventive system may include different requirements than a more expert user. For example, for a beginning user, the device may require the core contraction to start before and end after a qualifying movement to be considered a qualifying movement. Whereas for an expert user, the device may require the core contraction to start before and end after acceleration or velocity exceeding specified thresholds. This illustrates how the system may be calibrated and optimized to users of different proficiency levels. Further, the system can be optimized for therapeutic applications such as practiced in rehab clinics and occupational therapy clinics.

Figure 23B:
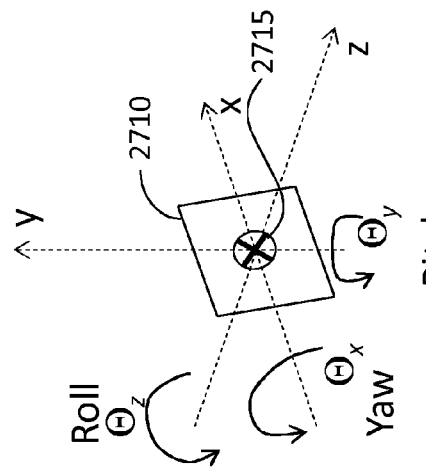
FIG. 23b-FIG. 23d show additional orientation primitives including yaw, pitch, and roll. These primitives may be useful when considering the output of gyros.
Figure 23A:
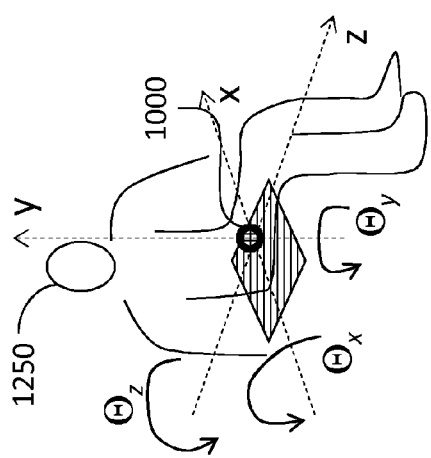
FIG. 23a shows the xyz coordinate system with the depiction of a user.
Figure 23D:
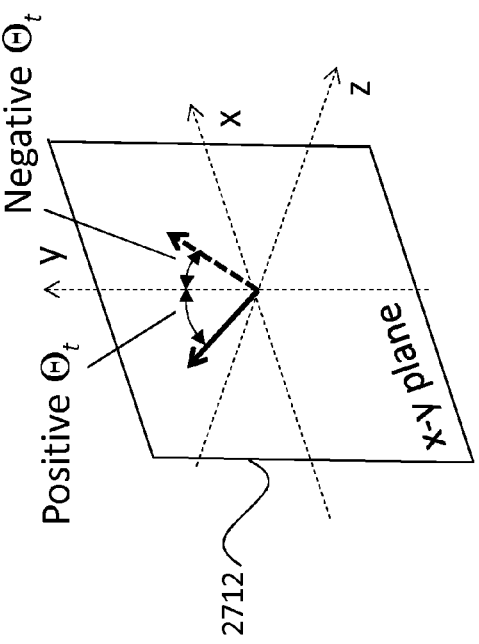
Figure 23C:
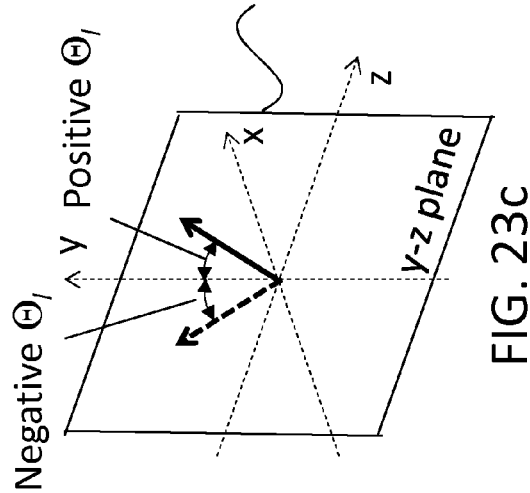

Let us further define some basic definitions for the user's orientation to the earth that may be used through the remainder of this document. FIG. 23*a* shows the xyz coordinate system with the depiction of a user. Let us assume the user is wearing a device on the waist in the preferred position 1200. Further, assume the wearable device is represented in FIG. 23*b* by a circle 1000. Let us place a circle with an x to mark the circle center near the center of the square in order to represent the location of the sensor group as shown in the figure. Let us refer to this as the center circle and allow it to be placed at some arbitrary point on the device as a point of reference. Movements of the device may equivalently refer to movements of this center circle. Since the center circle is on a plane defined by the square in the xyz coordinate system, we can now define some basic primitives to describe orientation of the user's body with respect to the earth. For most applications of qualifying movement identification, an approximate location of the sensor group in the device will suffice.

We may utilize terms commonly used in inertial navigation for rotation of the device or equivalently the center circle. These are shown in FIG. 23*b* and include the terms roll in the $\Theta_z$ rotational direction, yaw in the $\Theta_x$ rotational direction, and pitch in the $\Theta_y$ rotational direction. FIGS. 24*c*-24*d* show additional orientation primitives. In FIG. 24*c*, lean is defined in the y-z plane as $\Theta_l$, a radian angle referenced to the y-axis. When $\Theta_l$ is positive, the lean of the device is defined to be forward. When $\Theta_l$ is negative, the lean of the device is defined to be backward. In FIG. 24*d*, tilt is defined in the x-y plane as $\Theta_t$, a radian angle referenced to the y-axis. When $\Theta_t$ is positive, the tilt of the device is defined to be to the left. When $\Theta_t$ is negative, the tilt of the device is defined to be to the right. In the absence of movement, a 3-axis accelerometer may be used to determine lean and tilt.

The definition of the xyz coordinate system is arbitrary and may be time varying. For the purpose of qualifying movement identification, the following approach may be used:

a. When a static measurement (no substantial movement) such as lean or tilt is taken, the device may be assumed at the origin since only orientation to the y-axis is needed;

b. When a dynamic measurement is taken (during substantial movement), utilize the last identified static origin to track changes of position.

Instantaneous velocity or acceleration may be used for the identification of many qualifying movements. Pitch rotation due to rotation of the hips that may also be identified as qualifying movements, and may easily be identified using a gyro.

FIGS. 24*a*-24*d* show the sequence of the user changing from a seated position to a standing position where the instantaneous lean is shown as illustration in FIG. 24*e* through FIG. 24*h*. The vector indicating lean is shown as solid in FIG. 24*e* and FIG. 28*h* indicating these are assumed to be with the user at rest, i.e., no substantial movement. The vectors shown as lean in FIG. 24f and FIG. 24g are shown as dotted, indicating that they represent instantaneous lean during movement. Since lean and tilt are referenced to the y-axis, the location of the origin is arbitrary for the definition of these primitives.

Figure 25B:
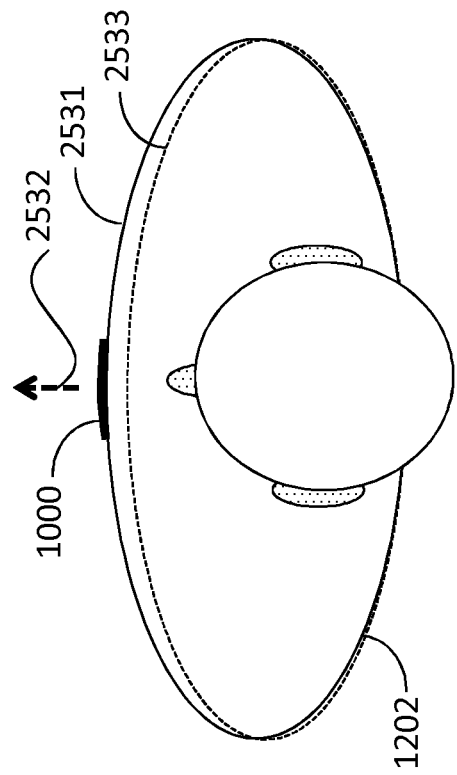
FIG. 25b shows the area under the navel and above the crotch protruding when the core is contracted.
Figure 25A:
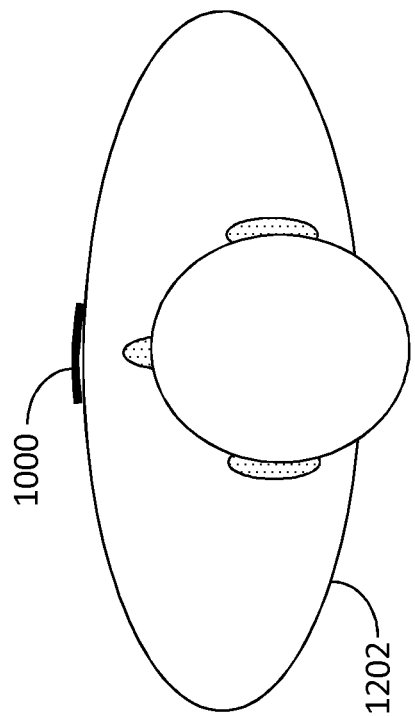
FIG. 25a shows a top view of a user with the device attached to the waist just under the navel.

FIG. 25a shows a top view of a user with the device attached to the waist just under the navel. FIG. 25b shows the area under the navel and above the crotch protruding when the core is contracted. Referring to the figure, the dotted line 2530 and solid line 2531 on the outlines of the user conceptually illustrates the position of the user's abdominal area before and during the core contraction. The change in position resulting from the core contraction is shown as vector 2532. These small movements are substantially in the z-dimension relative to the user. Different sensing methods utilizing different combinations of sensors may be utilized to detect core contraction and relaxation.

One approach may utilize an accelerometer and use the capability to calculate changes in position. However, it may be difficult to differentiate between a body movement in the z-dimension and a core contraction since movement in the z-dimension during a core contraction is relatively small compared to most body movements. False detection of a core contraction is more likely when using only an accelerometer. Alternatively, the device may be programmed so that detection of a core contraction may be limited to the user contracting their core prior to any other movement. This constraint may be acceptable for some applications and allow an accelerometer alone to be used to accurately sense a core contraction in an application utilizing a single accelerometer in a Single Sensor Group implementation.

Another approach may utilize a pressure sensor. As the core is contracted, the pressure on the pressure sensor may change. This change in pressure may be detected as a core contraction. If in addition to a pressure sensor an accelerometer is utilized, the accelerometer may detect a change in the z-dimension. The pressure change in conjunction with the position change may be used to assist in the identification of a core contraction. However, movements that result in rotating at the hips clockwise or counter clockwise or in a rotational movement forward either in the upward or downward direction may both increase pressure on the pressure sensor and result in a z-dimension change, potentially resulting in a false positive identification of a core contraction. In yet another approach, a pressure sensor and accelerometer may be utilized in addition to a gyro. In this configuration, when the pressure sensor detects a change in pressure and the accelerometer detects a change in the z-dimension, the gyro can be used to confirm the absence of a significant y-axis rotation. Furthermore, the gyro output may be used to make sure there were no sudden rotations of the body that may result in a false positive identification of a core contraction from the pressure sensor and/or accelerometer. The gyro maybe used to monitor rotations in the $\Theta_y$ direction. If the $\Theta_y$ rotation exceeds a threshold, the device may flag a qualifying movement of a hip rotation. Furthermore, the accelerometer can be used to ensure the user was upright and that a small z-dimension movement was also detected coincident with the increase in pressure detected by the pressure sensor.

Operational Example 2

Single Device—Multiple Sensor Group

In Single-Device Multiple Sensor Group implementations, a device may contain at least two groups of sensors. Each group of sensors may contain one or more sensors. More than one type of sensor may be utilized.

A desirable combination of: a. Placement of the sensor groups in the device; and b. Manner and location of attachment of the device onto or near the body may be selected to improve the information provided by the sensor groups to identify different body movements and body movement sequences. The body movements and body movement sequences that may be identified may include qualifying movements and core contraction.

Since the sensor groups are contained in one device, the different sensor groups substantially measure similar movements. However, with appropriate placement of the sensor groups in the device, the sensors may be able to detect differences in movement between sensors. In such an implementation, the difference between movements of the sensor groups may contain desired information. This approach may be referred to as differential sensing.

For example, when core contraction is sensed using accelerometers, differential sensing may be used to differentiate general body movements from core contractions. In differential core sensing, at least two sensor groups are utilized in the device. The identification of a core contraction may be assisted by the measured difference in movements between a sensor or sensors placed on or near the core sensing 2202 position and a sensor or sensors placed on or near the anchor sensing position 2201.

Figure 26A:
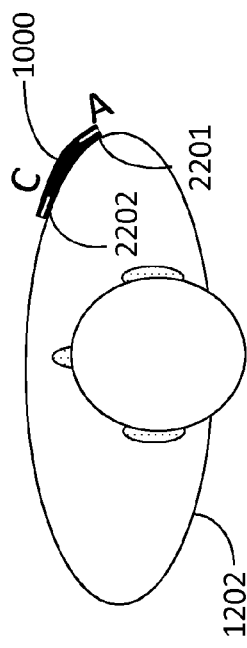
FIG. 26a, shows a top view of a user with a device set up for differential core sensing with the core and anchor sensing positions indicated with the C and A, respectively.
Figure 26B:
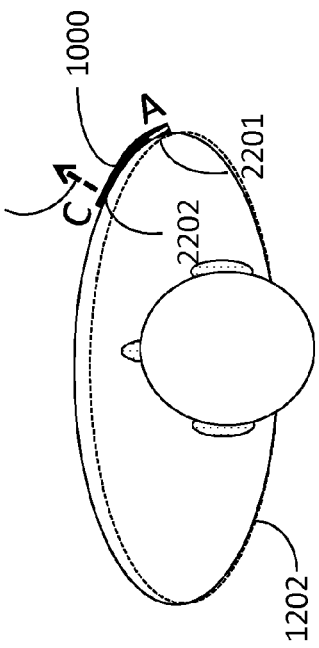
FIG. 26b, shows via vector 2210, when the user's core is contracted, the core section may move outwards causing the C sensors to move outwards.
Figure 26C:
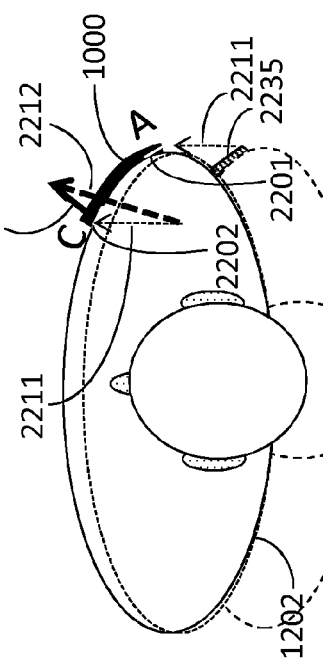
FIG. 26c, shows a movement forward of the user shown as movement of both positions C and A as a common vector 2211 and a core contraction shown as vector 2210.

FIG. 26a, shows a top view of a user with a device set up for differential core sensing with the core and anchor sensing positions indicated with C and A, respectively. When the user contracts their core, the core section may move outward causing the C sensors to move outward as shown by vector 2210 in FIG. 26b. Since the anchor position did not move in this example, the movement of position C is sufficient to determine a core contraction. In FIG. 26c, a movement forward of the user is shown as both positions C and A moving the same direction and magnitude as a common vector 2211. Suppose the user simultaneously contracts their core. This may cause position C to further move in the direction of vector 2210. Therefore, the total position C change will be vector 2212 which is the vector sum of vectors 2211 and 2210. By evaluating the vector describing the movement of position C minus the movement of position A which is the difference of vector 2212 minus vector 2211, the movement that is unique to position C relative to position A can be calculated and may be used to assist in the identification of a core contraction.

Figure 27A:
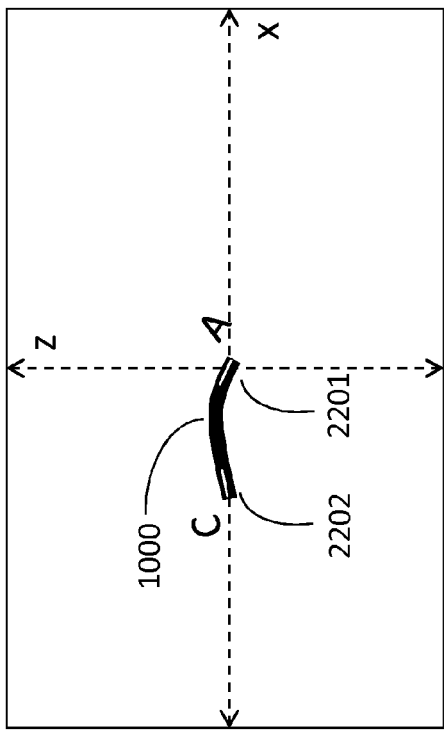
FIG. 27a shows xyz coordinates, defined to the right front of the user.
Figure 27C:
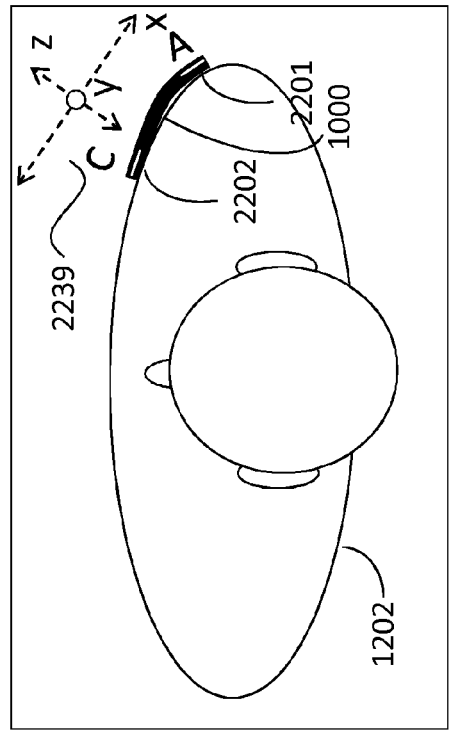
FIG. 27c shows in the implementation utilizing differential core sensing with separate PCBs, the z-axis for the accelerometer in position C shown as $z'_C$ may point in a direction normal to position C while the z-axis for the accelerometer in position A shown as $z'_A$ may point in a direction normal to position A.
Figure 27B:
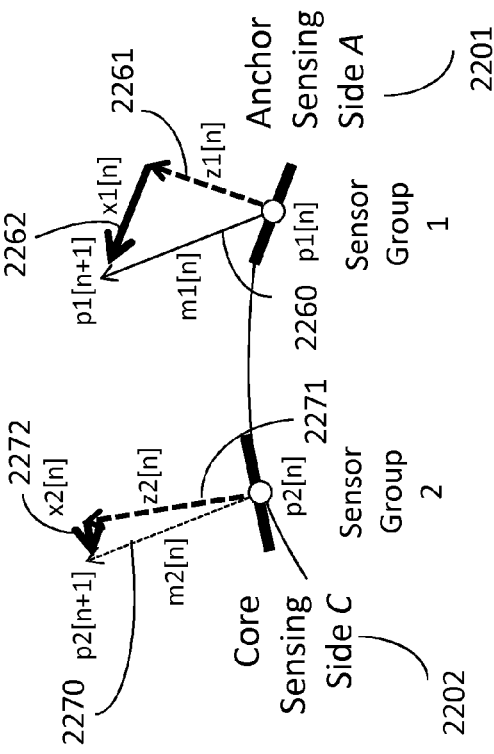
FIG. 27b shows the device on the x-z plane.
Figure 27D:
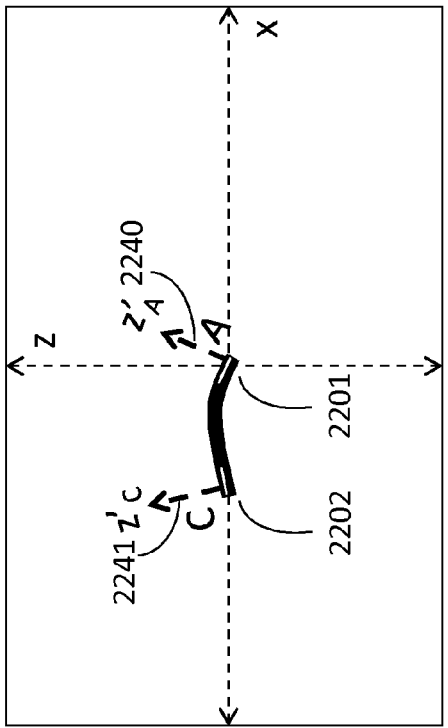
FIG. 27d shows p1[n] as the anchor sensing position and p2[n] as the core sensing position at time n and further defines vectors to illustrate how differential sensing may be used to detect contraction of the user's core.

Some additional aspects of the implementation may be illustrated by further examination of the computations associated with this approach. Let us assume that the output of the sensors is monitored multiple times per second so that changes in movement are relatively small from timestamp to timestamp. For example, the output of the sensors may be sampled at a 100 hertz rate. In FIG. 27a, xyz coordinates 2239 are defined to the right front of the user. In FIG. 27b, the device is shown on the x-z plane. Let us assume there are two two-dimensional accelerometers in both anchor and core positions. Let us define the z-axis for each of the accelerometers as an axis perpendicular to the face of the device at the location of each accelerometer. With this definition, position C may have axis $z'_C$ 2241 which may point in a direction normal to the accelerometer in position C and position A may have axis $z'_A$ 2240 which may point in a direction normal to the accelerometer in position A as shown in FIG. 27c. Referring to FIG. 27d, z1[n] 2261 and x1[n] 2262 are $z'_A$- and $x'_A$-dimension movement vectors calculated from the difference in position of the accelerometer in position A 2201 moving from timestamp n to timestamp n+1. Similarly, z2[n]

2271 and x2[n] 2272 are $z'_C$- and $x'_C$-dimension movement vectors calculated from the difference in position of the accelerometer in position A 2201 moving from timestamp n to timestamp n+1. Let us define p1[n] as the anchor sensing position 2240 and p2[n] as the core sensing position 2241 at time n, and define p1[n+1] and p2[n+1] as the anchor and core sensing positions at time n+1. By measuring the incremental change in the x- and z-dimensions using coordinate systems defined by $z'_C$ and $z'_A$, the vectors and positions just defined, and the Pythagorean Theorem, incremental movement vectors m1[n] 2260 and m2[n] 2270 may be calculated. In the absence of pitch rotation, m2[n] 2270-m1[n] 2260 may be a measure of movement of the core region and may be utilized to assist in the identification of a core contraction. This approach enables a core contraction which is a relatively small movement to be identified during a movement of the body which may be a relatively large movement in an embodiment utilizing accelerometers.

Figure 28:
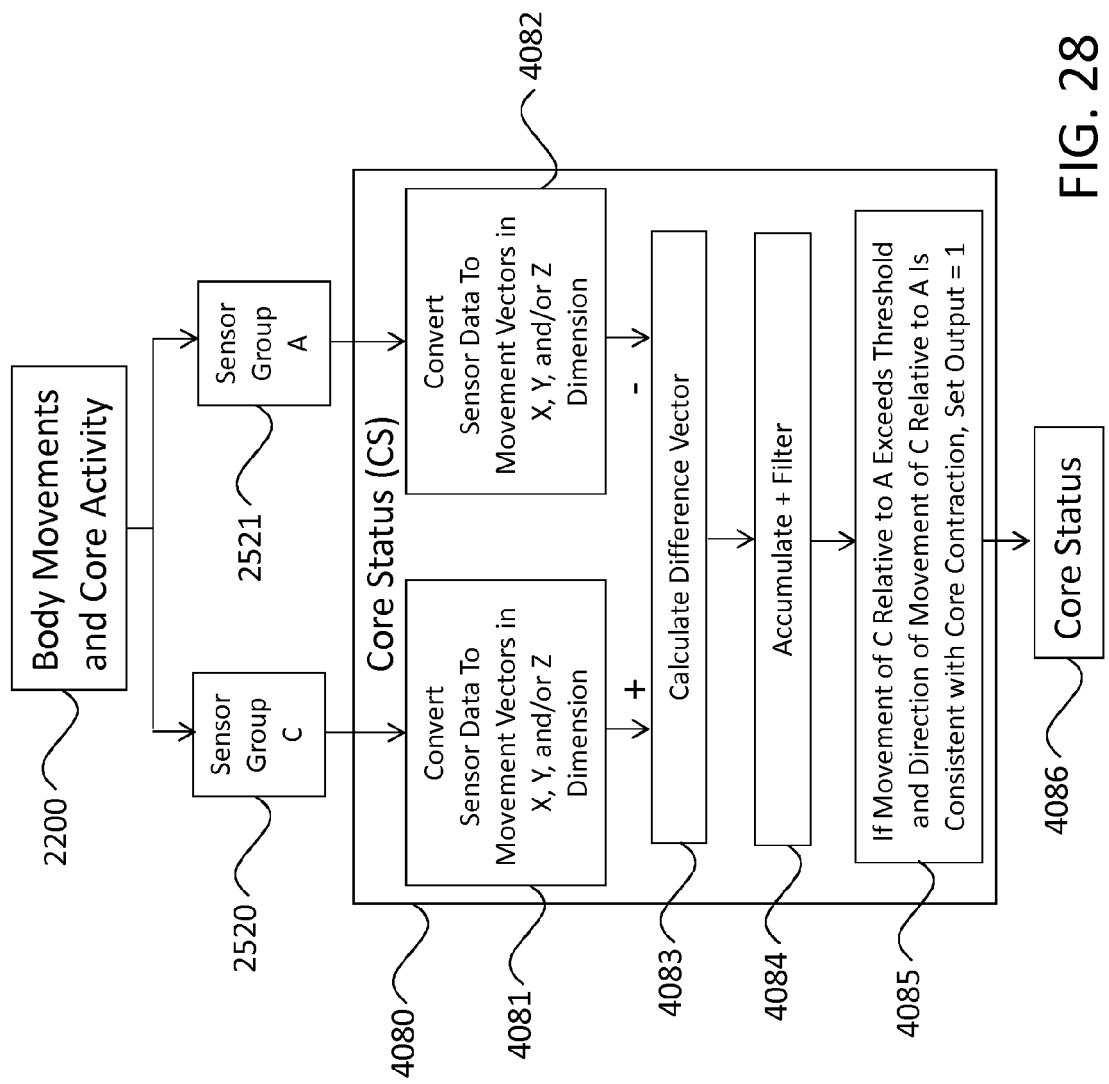
FIG. 28 is a flow diagram of the signal processing described in the embodiment utilizing differential core sensing.

In FIG. 28, a flow diagram of the signal processing described above is shown. Core status (cs) 4080 and core status 4086, Sensor Group C 2520 and Sensor Group A 2521 attach to the core and anchor locations, respectively. In the most general case, signals from sensors may be converted to movements in 3-dimensional space as indicated in the description of blocks 4081 and 4082. For many calculations such as assisting in the identification of core contraction utilizing accelerometers as just described, two dimensions may be adequate. Sensor data is converted to incremental movement vectors by blocks 4081 and 4082. Movement vector data is passed to a block that calculates the differential movement vector 4083 from the vector corresponding to the core movement minus the vector corresponding to the anchor movement. This differential movement vector may be accumulated and/or filtered 4083. When the difference of position of the core relative to the position of the anchor exceeds a threshold and the direction of the movement of the core relative to the position of the anchor is consistent with a contraction of the core, the algorithm may identify that a core contraction may have occurred and may signal this result to the system 4085. Other available data may be used to increase the reliability of the result. For example, the time taken for the core to change from the relaxed state to the contracted state may be used to further qualify the detected result.

Operational Example 3

Multiple Device Implementations

The presented principles may be applied to applications utilizing multiple devices wherein each device may utilize single sensor group or multiple sensor group configurations.

A desirable combination of: a. Placement of the sensor groups into each device; and b. Manner and location of attachment of the each of the two or more devices onto or near the body may be selected to improve the information provided by the sensor groups to identify different body movements and body movement sequences. The body movements and body movement sequences that may be identified may include the identification of qualifying movements and core contraction. With multiple devices, more complex movements may be identified.

Figure 29C:
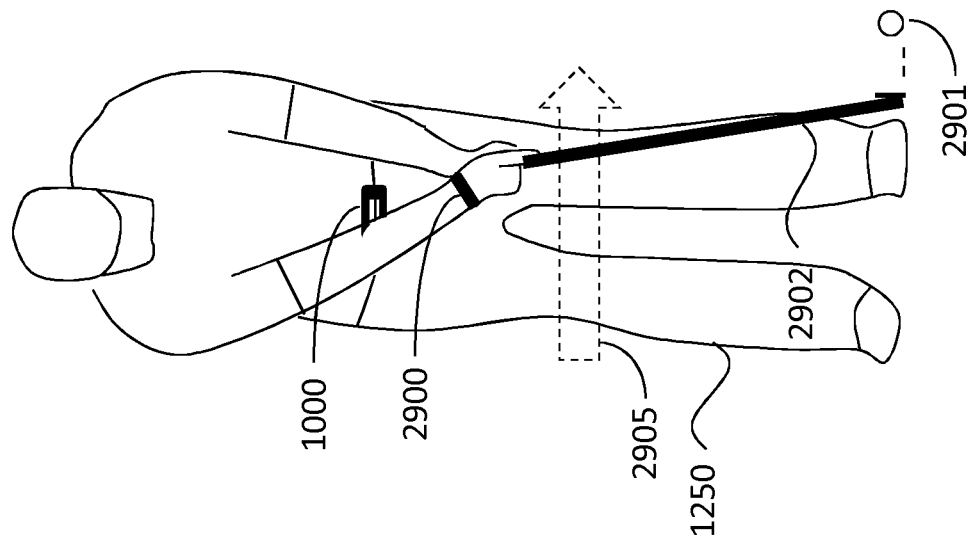
FIG. 29c illustrates a forward stroke where the ball is struck during the forward stroke.
Figure 29B:
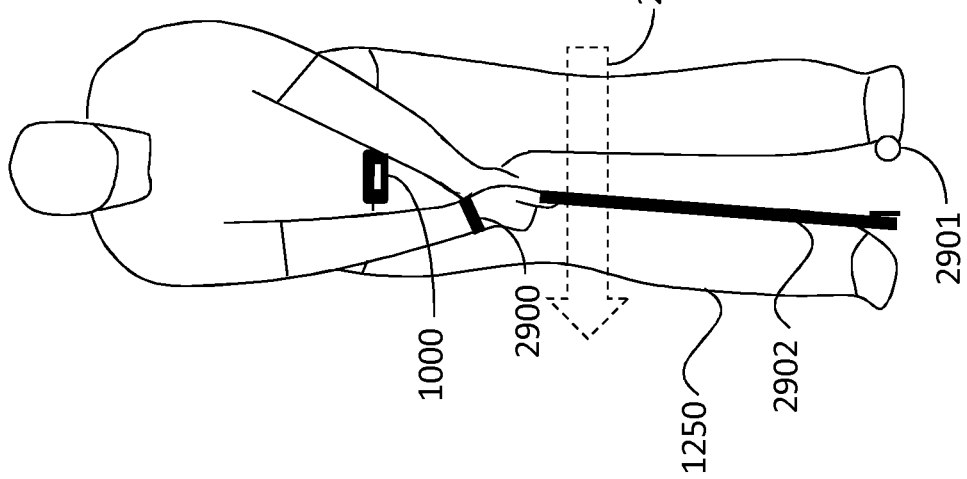
FIG. 29b illustrates the golfer beginning with a back stroke.
Figure 29A:
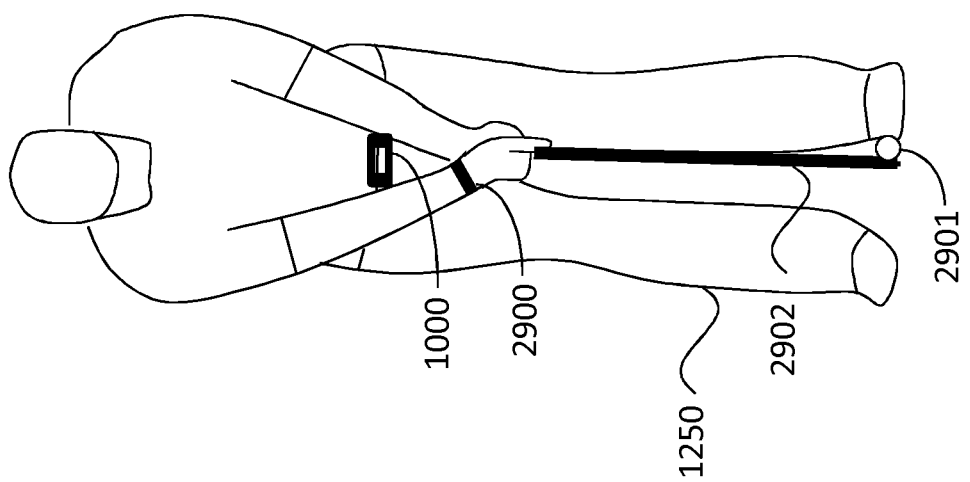
FIG. 29a illustrates the setup of a golfer preparing for a putting stroke.

Multiple device implementations may be used for applications that utilize core sensing as a portion of the application. For example, core contraction may have benefits for stabilizing the torso during the execution of certain golf strokes. This may be one example where the inventive system may utilize more than one device. A golf stroke for which core contraction may be beneficial may include the putting stroke. The putting stroke has substantially two motions as shown in FIG. 29. Starting with the stroke setup shown in FIG. 29a, the golfer may begin with a back stroke shown in FIG. 29b, and a forward stroke where the ball is struck during the forward stroke shown in FIG. 29c. It may be desirable to have the hands move in a substantially pendulum manner where the back stroke is substantially in the same plane as the forward stroke which continues after striking the ball.

For this application, at least two devices may be used. One device may be worn on one wrist, for example, the right wrist 3000 of a right handed golfer to monitor hand movements while another device may be worn on the waist as has already been described to monitor the core. These are identified in FIG. 29a. As the user begins the putting stroke using golf club 3002, the device on the wrist may monitor hand movements for a proper pendulum motion in the putting stroke while the device on the waist may monitor core contraction until the golf ball 3001 has been hit. In this case, the qualifying movement is the putting stroke. Data from the different sensor groups may be utilized to maximize the likelihood of a correct identification of the movements associated with a putting stroke. For example, a golf putting stroke may be identified as it is detected that the user is slightly crouched forward at the waist while the body is kept substantially still, while the hands have a movement associated with a putting stroke which is a movement back and then forward in substantially the same or similar plane of movement.

In this and similar applications, signaling from one or more devices may be used to identify or acknowledge additional behaviors. The device on the waist may operate as described earlier and signal to the user based the identification of protected or unprotected qualifying movements. In addition to signaling based on the identification of protected or unprotected qualifying movements, one or more devices may be configured to signal to the user based on other criteria. For example, in golf, the movement of the hands in substantially the same or similar movement plane with a pendulum motion is desirable in a putting stroke 3004. This desired movement of the hands may be translated into a position trajectory on the back stroke 3004 and forward stroke 3005 as shown in FIG. 29b-29c further, changes in speed and/or acceleration may be monitored. Based on targets which may have default values or be programmable, user trained, or adapted, the device or devices may evaluate if the measured performance is within limits of the targets and provide feedback to the user. Feedback may be provided by a Signaling Unit. The Signaling Unit may be in the device on the waist. Alternatively, there may be additional Signaling Units. For example, one may be in the device on the wrist. The additional Signaling Units may also be in an external device or handheld device such as a smart phone or electronic pad. The signaling for such a device may be a spoken voice providing specific feedback and instruction.

Figure 30:
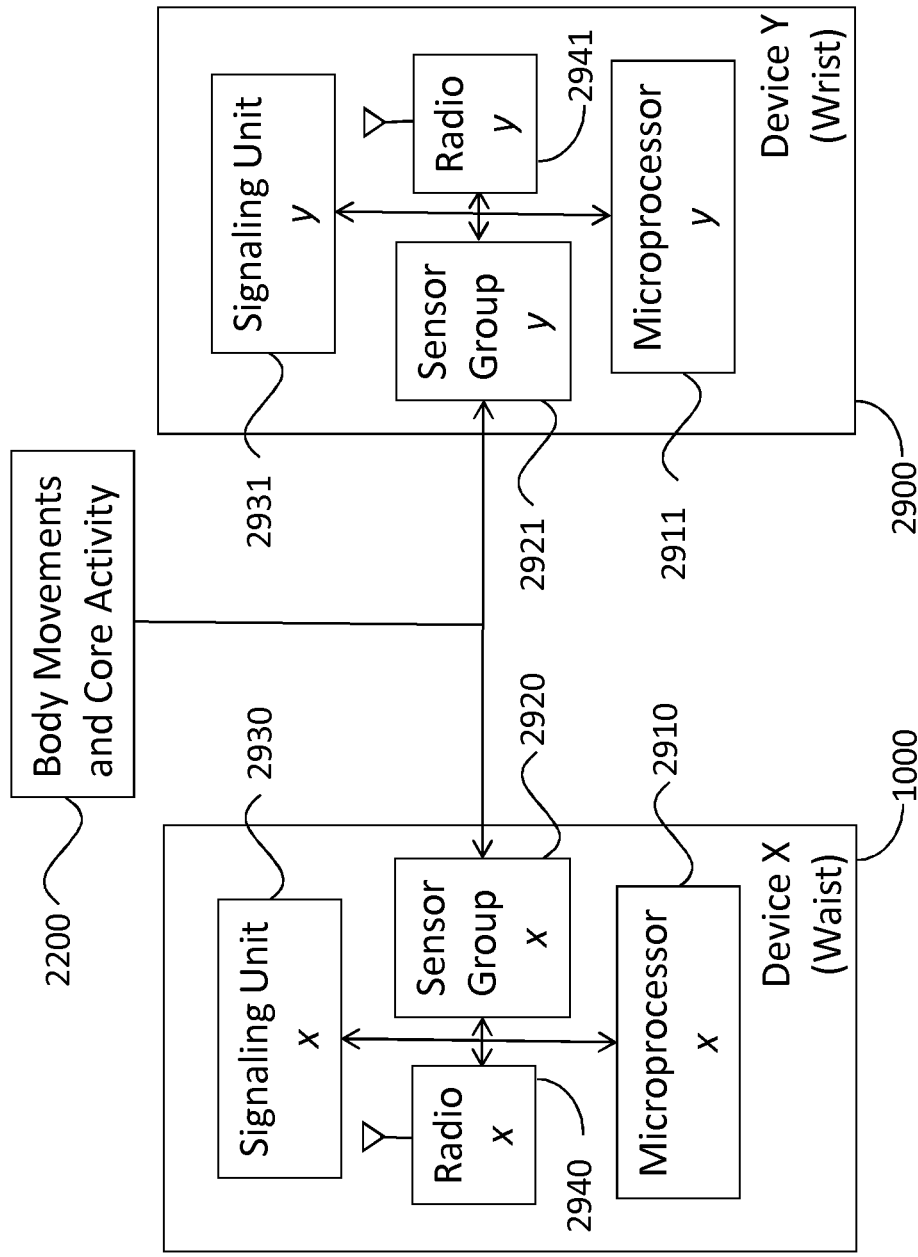
FIG. 30 illustrates a block diagram of the elements contained in the device worn on the waist and the device worn on the wrist having at least one sensor group, at least one microprocessor, and at least one radio, and at least one of the devices may have at least one signaling unit.

Let us refer to the device on the waist Device X and the device on the wrist Device Y. As shown in FIG. 30, each of the devices may have at least one sensor group 2920/2921, at least one radio 2940/2941, one or both devices may have at least one microprocessor 2910/2911, and one or both devices may have a signaling unit 2930/2931. At least one of the radios may be capable of communicating with a handheld device or PC. The devices may share the processing capability of one microprocessor. For example, Device Y may send data from its sensor group to Device X where sensor data from all sensors are processed together.

Use of a handheld device or PC may be used to program the device or devices for specific applications such as golf so that algorithms that are optimized for specific applications may be utilized.

Figure 31A:
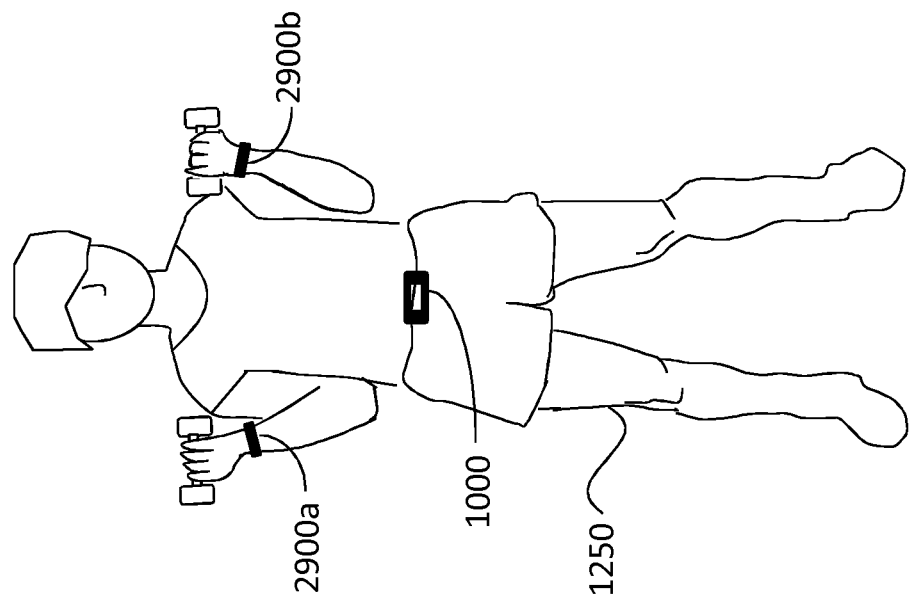
FIGS. 31a-31b show the two-device system utilized to encourage core contraction support during up-down weightlifting exercises.
Figure 31B:
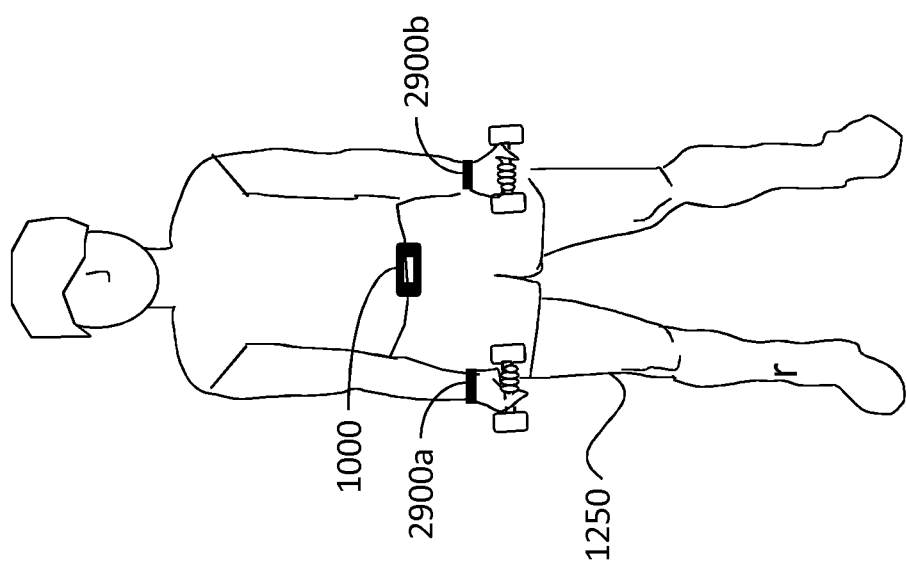

Another application example is, according to an embodiment, to use the inventive system to encourage core contraction support during weightlifting exercises. This is illustrated in FIG. 31. For example, it may be desirable to contract the core prior to performing an arm curl to stabilize the body and support the lumbo-sacral junction. For this application, at least three devices may be used. One device may be worn on each wrist to monitor hand movements while another device may be worn on the waist as has already been described, to monitor the core. These devices are identified in FIG. 31*a*. The user begins with the arms out, holding dumbbell weights in each hand 3001*a*-3001*b* as shown in FIG. 31*a*. Followed by the curling movement where the dumbbells are lifted with a contraction of the biceps as shown in FIG. 31*b*. The devices on the wrists may monitor hand movements that together with the device on the waist may be used to identify repetitions of exercise. In a preferred method of performing the exercise, the core may be contracted before the weights are brought to the down location, then the core may be relaxed. Then, before the weights are lifted to the position shown in FIG. 31*b*, the core may again be contracted and then the weights may be lifted. Repetitions of exercise may be identified as qualifying movements, allowing the device to check core contraction in conjunction with each repetition.

Basic Signal Flow Diagram

Let us now examine more closely the implementation of the signal processing algorithms contained in the high level block diagram introduced back in FIG. 10*a*. Let us start with a transition from a high level block description to functional blocks. Then, in the following section we will expand the functional blocks to signal processing blocks.

Figure 32A:
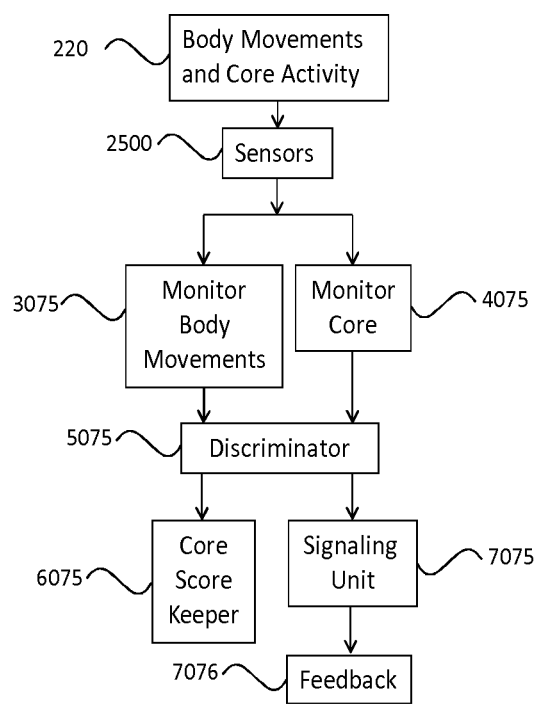
FIG. 32a illustrates one implementation of the high level Signal Processing block of FIG. 10a showing more detail as functional blocks.

One implementation of the high level Signal Processing block of FIG. 10 showing more detail as functional blocks is shown in FIG. 32*a*. It is assumed that analog and digital signal processing may be used interchangeably so conversion of inherently analog signals to digital is not indicated. For example filtering and/or gain may be performed in either or a combination of both the analog and digital domains. Therefore, these details are not included in the diagrams. Neither is the conversion of inherently analog signals to the digital domain where the signal processing algorithms may substantially be performed.

Figure 32B:
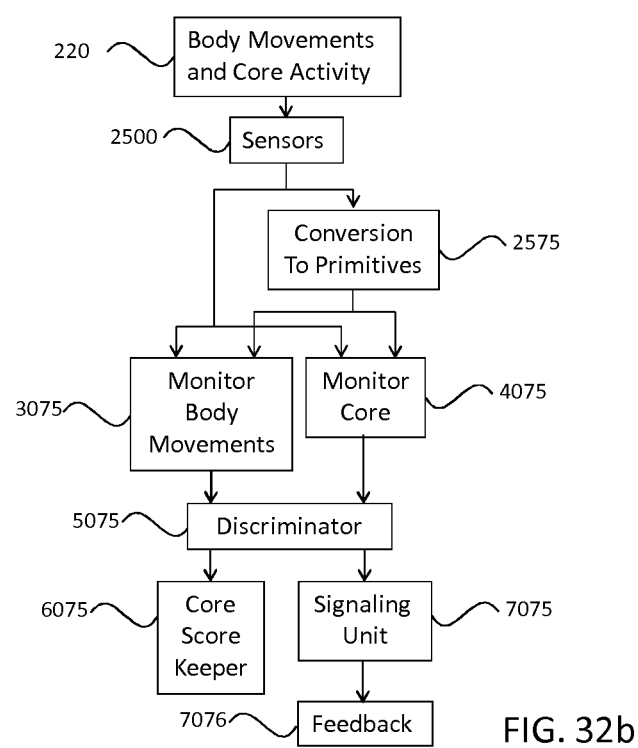
FIG. 32b illustrates the Convert to Primitives functional block, shown explicitly between the sensors and the Monitor Body Movements and Monitor Core functional blocks.

The Sensors function 2500 provides sensor data to the system. The sensor data may be directly available from some sensors, while other sensors may require output signals to be further processed in order to become sensor data that may be utilized by the rest of the system. Sensor data may be input to at least two functional blocks with one being a Monitor Body Movements function 3075 and the other a Monitor Core function 4075. The Monitor Body Movements function 3075 processes data from the Sensors 2500 to identify qualifying movements while the Monitor Core function 4075 identifies core contractions. The Discriminator function 5075 takes in the identification of and data associated with the qualifying movements and the identification and data associated with a core contraction and determines if the qualifying movement is protected or unprotected. The output of the Discriminator function 5075 is input to the Core Score Keeper function 6075 and the Signaling Unit function 7075. The Core Score Keeper stores data on qualifying movements and the number of protected and unprotected qualifying movements. The Signaling Unit function 7075 generates a feedback signal in the form of the Feedback function 7076. In FIG. 32*b*, the Convert to Primitives function 2575 is shown explicitly between the sensors and the Monitor Body Movements function 3075 and the Monitor Core function 4075. This illustrates that fundamental data such as primitives may be computed and shared by all processing blocks. A line also indicates a bypass of the Convert to Primitives block indicating that the sensor data may also be fed to and used directly by all the processing blocks.

Figure 32C:
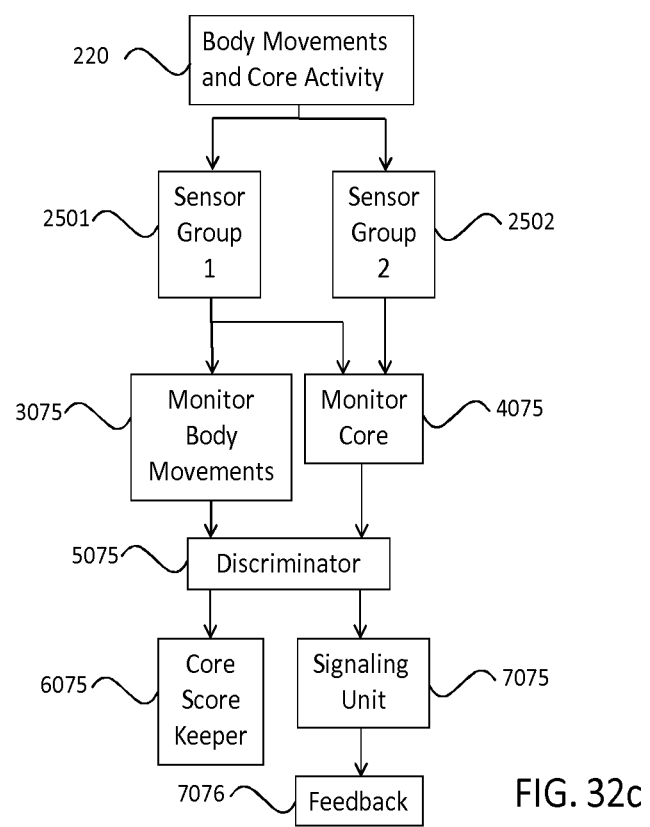
FIG. 32c illustrates an example of two sensor groups being used for differential detection. This configuration may also be used to enhance identification of a core contraction.

An example of two sensor groups being used for differential detection is shown in FIG. 32*c* where data from both Sensor Groups 1 and 2 may be used by the Monitor Core function 4075 while the data from Group 1 alone may be used by the Monitor Body Movements function 3075.

Figure 32D:
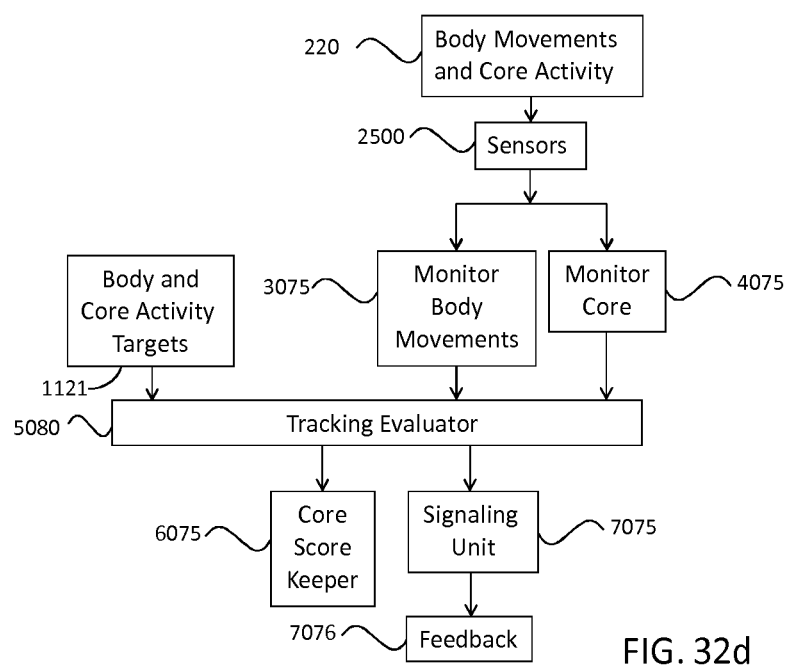
FIG. 32d illustrates an example of the device operating in conjunction with an exercise video or app which prescribes Body and Core Activity Targets which the user may attempt to follow. The Comparator evaluates numerical differences between Body and Core Activity Targets and the movements and activity of the body and core of the user and feedback is provided to the user.

An example of an Exercise Video or Instructional App 1300 providing Body and Core Activity Targets 1121 is shown in FIG. 32*d*. On the right side of the figure are the Monitor Body Movements 3075 and Monitor Core functions 4075. These are compared against the targets 1121 and compared by the Comparator 5080 and Feedback 7076 may be provided.

Figure 33A:
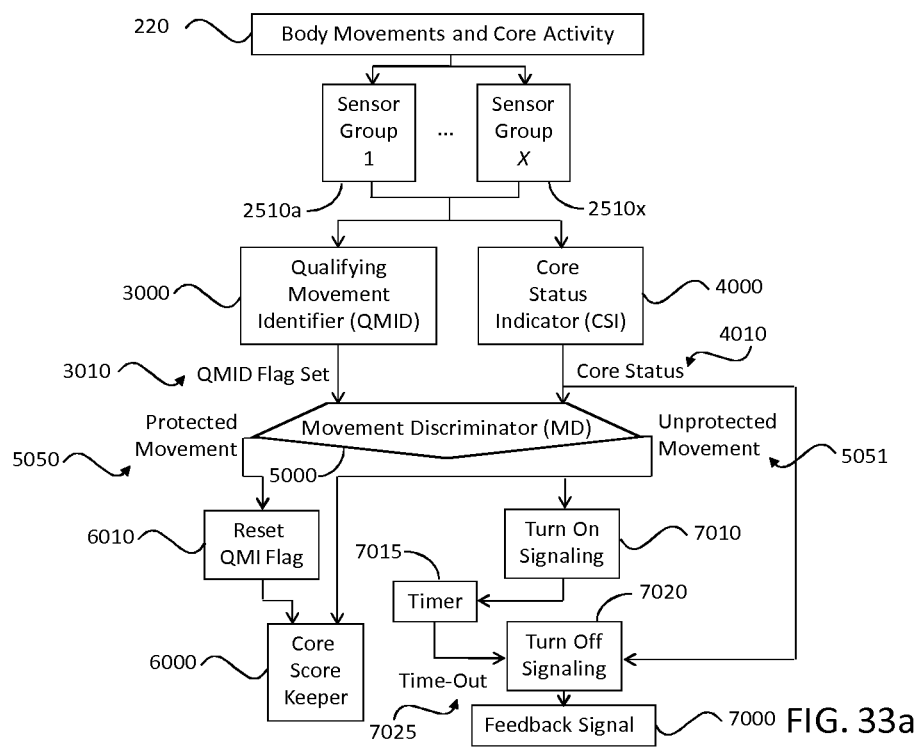

A high level view of the signal processing blocks of one embodiment of the inventive system for developing procedural memory for core support of qualifying movements is shown in FIG. 33*a*. Body movements and core activity 2200 are inputs to one or more sensor groups 2510*a*-2510*x*. The sensor groups 2510 may convert body movements and core activity 2200 into signals for signal processing blocks which follow. Sensor data may be directly available from some sensors, while other sensors may require output signals to be further processed in order to be utilized by the rest of the system. Any such processing may be included as part of the sensor group definitions. The output of the sensors may be input into Qualifying Movement Identifier block 3000 and a Core Status Indicator block 4000. The qualifying movement may set the QMID Flag 3010 when a qualifying movement is identified. The Core Status Indicator 4000 may regularly monitor the core for contraction and relaxation and output the status of the core with a Core Status signal 4010 which may be active during the identified time of core contraction. The QMID Flag 3010 may be active during the identified time of a qualifying movement. The Movement Discriminator 5000 may evaluate the relationship between the QMID Flag 3010 and the Core Status signal 4010 to determine if the qualifying movement is a Protected Movement 5050 or an Unprotected Movement 5051. The outputs of the Movement Discriminator 5000 may be input to the Core Score Keeper block 6000 and the generator of the Feedback Signal 7000. Reset QMI Flag is represented by block 6010, turn on signaling is represented by block 7010, turn off signaling is represented by block 7020, and time out is represented by block 7025. In some applications, the QMID block may output additional data such as position, velocity, acceleration, and information regarding the identified qualifying movement. Further, the CSI block may output additional data such as core contraction intensity and direction of core movement during the contraction. A more advanced Movement Discriminator may be required in these applications.

Since a qualifying movement may be identified after a movement is complete, the beginning and end of a qualifying movement may only be identified after the movement is complete. By storing samples in memory of many or all of the signals including the QMID Flag 3010 and the Core Status signal 4010, the time relationship of the qualifying movement and core contraction may be evaluated by the Movement Discriminator 5000 and the Feedback Signal 7000 may be provided with a short enough time delay to support the development of procedural memory for core support timing and usage.

Figure 33B:
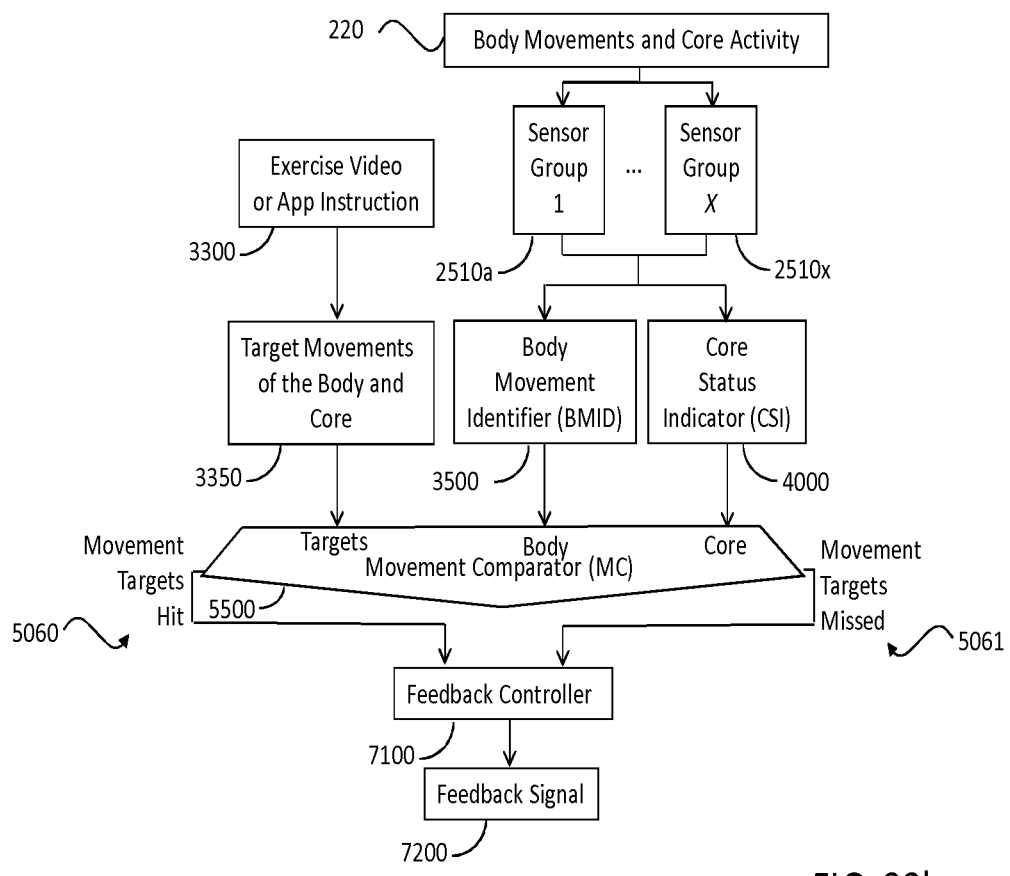
FIG. 33b illustrates an example of the signal processing blocks in an implementation in which the body movements and core contraction are evaluated against target movements as may be provided by an exercise video or app.

A high level view of the signal processing blocks of one embodiment of the inventive system for developing proper core usage with a video or app is shown in FIG. 33b. The instructional app or video performs instruction 3300 to the user on a smart phone or PC or other device with a video display or speaker. Synchronous with the instruction, the program running the video or app generates pre-recorded target movements of the body and core 3350 to a Movement Comparator (MC) block 5500. As the user follows the instruction with body movements and core contraction, these movements are input to Sensors 2510a-2510x. The output of the sensors is input to two blocks. The CSI block monitors contraction and movement of the core. The QMID block of FIG. 33a is replaced with the Body Movement Identifier (BMID) block 3500. The BMID block identifies and reports body movements and associated data. The output of the BMID and CSI blocks include information regarding body movements and core contraction. This data along with the target movements of the body and core 3300 are evaluated by the Movement Comparator block. The target movements of the body and core 3300 may be signal representations, for example time-domain representations, of specific movements as generated by the BMID and CSI blocks with an expert user wearing the device and executing the instructions under ideal conditions.

The Movement Comparator may compare elements such as the core contraction following the target core contraction within an acceptable delay, for example, within 250 msec. These delays may be variable and dependent upon the exercise or subject of the teaching and the level of the student. The Comparator may compare simultaneous movements such as a core contraction with a movement inwards of the core sensing area. In this example, the Movement Targets Hit 5060 may include a core contraction within an acceptable delay following the target. However, the Movement Targets Missed 5061 may include the absence or inadequate movement of the core inward. A measure of the degree of inadequacy of the movement may be reported. This data may be fed back to a Feedback Controller 7100 capable of generating and providing Feedback Signal 7200 to the user. The feedback may be audible with signals such as a buzz or a chime, or may be converted to language feedback with the use of appropriate software. For example, a voice may be played back stating "Your core did not move sufficiently inward".

Next, we will present more detail regarding the blocks presented in FIG. 33a. Based upon the description of these blocks, modification of the QMID to implement the BMID and modification of the MD to implement the MC of FIG. 33b should be apparent to one reasonably skilled in the art.

Qualifying Movement Identifier (QMID)

Figure 34:
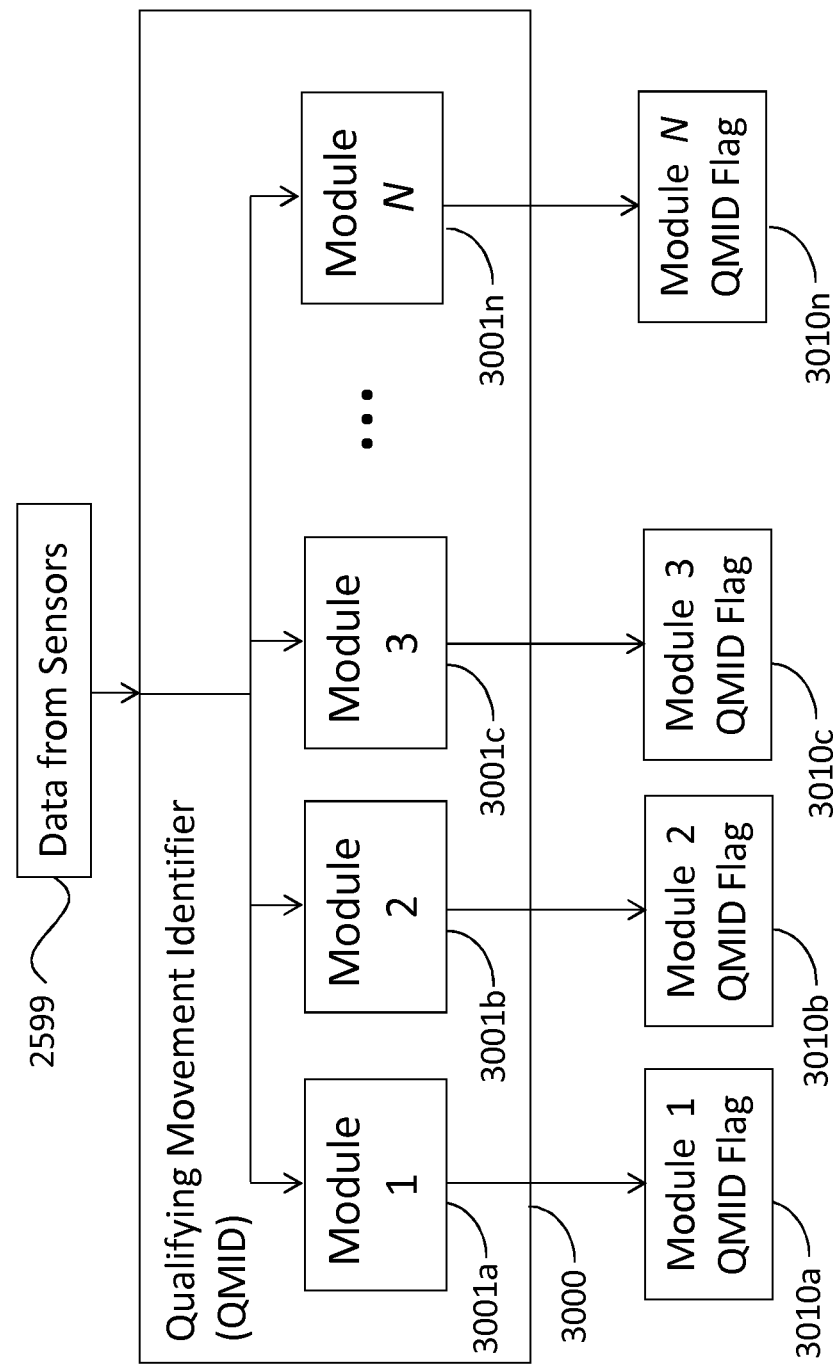
FIG. 34 illustrates the QMID block may be comprised of N separate modules running simultaneously to identify specific types or classes of movements.

The Monitor Body Movement function may be implemented with a Qualifying Movement Identifier (QMID) block shown in FIG. 34 that identifies qualifying movements to the device using one or more functional algorithms that operate on sensor data 2599. In this implementation, the output of the QMID block may be a QMID Flag, a status bit that communicates to the device that a Qualifying Movement has been identified. When a Qualifying Movement is identified, the QMID block may set the QMID Flag for a length of time. The length of time may be fixed, programmable, calibrated, or context dependent. After the time expires, the QMID Flag may be reset.

The QMID block may be comprised of N separate modules 3001a-3001n running simultaneously as shown in FIG. 34 designed to identify specific types or classes of movements. Each module may have a QMID flag output. The modules may each be designed to flag a qualifying movement based on different movement triggers. For example, one module may track the sitting to standing change in position and trigger when the y-dimension velocity increases beyond a threshold for a minimum period of time. Another module may track the rocking forward motion of moving from leaning back in a chair to leaning forward in the chair and trigger when the rotational velocity exceeds a threshold for a minimum period of time. While another module may track left to right or right to left rotations of the torso and trigger when the rotational velocity in either direction exceeds a threshold for a minimum period of time. These modules are essentially run in parallel and therefore shown diagrammatically in parallel. However, the implementation of the signal processing can be in series or a combination of series and parallel. Furthermore, the modules may share common results.

Core Status Indicator (CSI)

The Monitor Core function may be implemented with the Core Status Indicator (CSI) block that may indicate contraction of the core to the device through the Core Status Indicator or CSI bit. When the core is contracted, the output of this block may be CSI=1. When the core is relaxed or not contracted, the output may be CSI=0.

Figure 35:
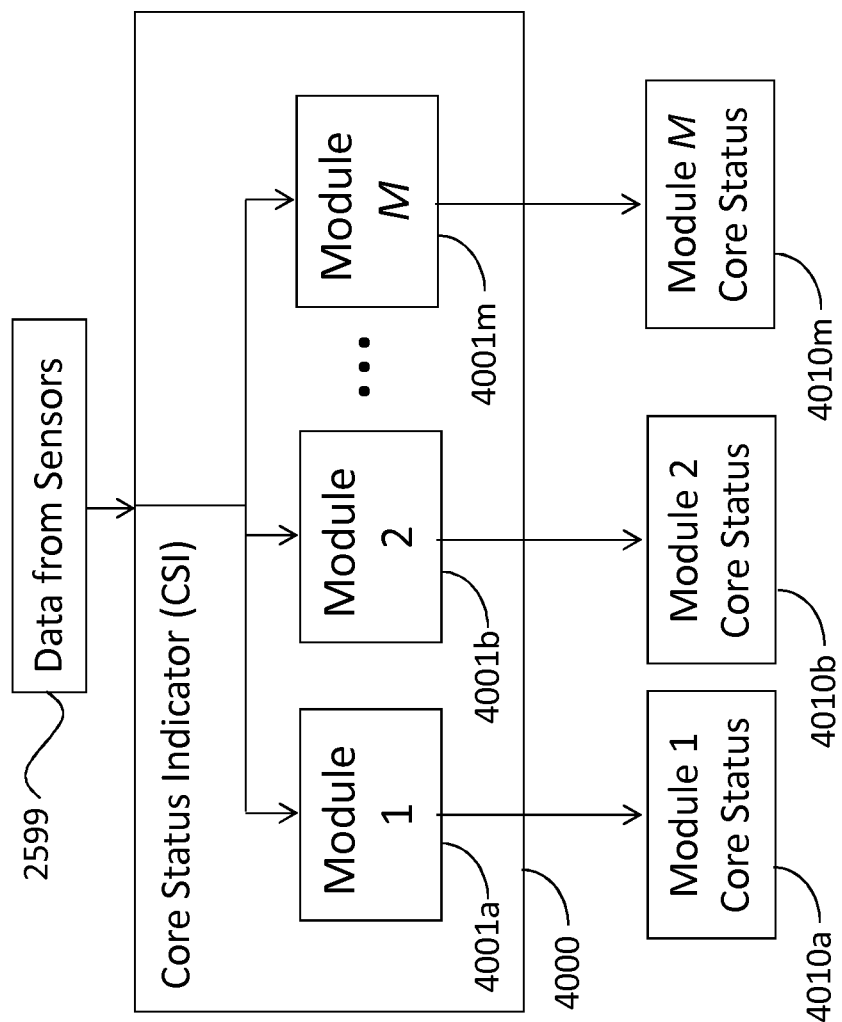
FIG. 35 illustrates the CSI block may be comprised of M separate modules running simultaneously to increase the accuracy of identifying a core contraction.

Different algorithms and approaches may be used to identify contraction and relaxation of the core as indicated in FIG. 35 where M parallel [[m]] modules 4001a-4001m are shown. These modules are essentially run in parallel and therefore shown diagrammatically in parallel. However, the implementation of the signal processing can be in series or a combination of series and parallel. Furthermore, the modules may share common results.

The N different modules in the Qualifying Movement Identifier block are designed to identify different movements or movement sequences of the body. They may be specifically associated with one or more of the M different modules in the CSI block as indicated in the figure as the outputs of the QMID and CSI blocks have module outputs going to Movement Discriminator modules to be discussed in the next section.

Let us take a simple example to illustrate how the QMID block may provide data to simplify detection of a core contraction by the CSI block. When a user is lying down on their back and moving to their left or right as you may move to get out of bed, the z-dimension component of the accelerometer may be substantially near 1G (where G is the gravitational force). The x-dimension component of the accelerometer may detect movements in the left or right direction. Let us assume the device has an accelerometer, pressure sensor, and gyro. Since the user is on their back, gravity may pull their core sensing area toward the body, lowering pressure on the sensor. The z-dimension of the accelerometer on a core contraction may be more heavily weighted in the calculation of a core contraction. This information may be reflected in the implementation of the algorithms in the CSI modules.

Movement Discriminator (MD)

The Discriminator function of FIG. 32 may be implemented with the Movement Discriminator block that takes the QMID Flag and the CSI output bit and performs decision algorithms that turn on and off the Signaling Unit. As described earlier, decisions may be based primarily on the timing and logical relationship of CSI output bits to QMID Flags. The output of the Movement Discriminator is either Protected Movement=1 or Unprotected Movement=1. Each QMID Flag may result in one of these decisions.

Figure 36:
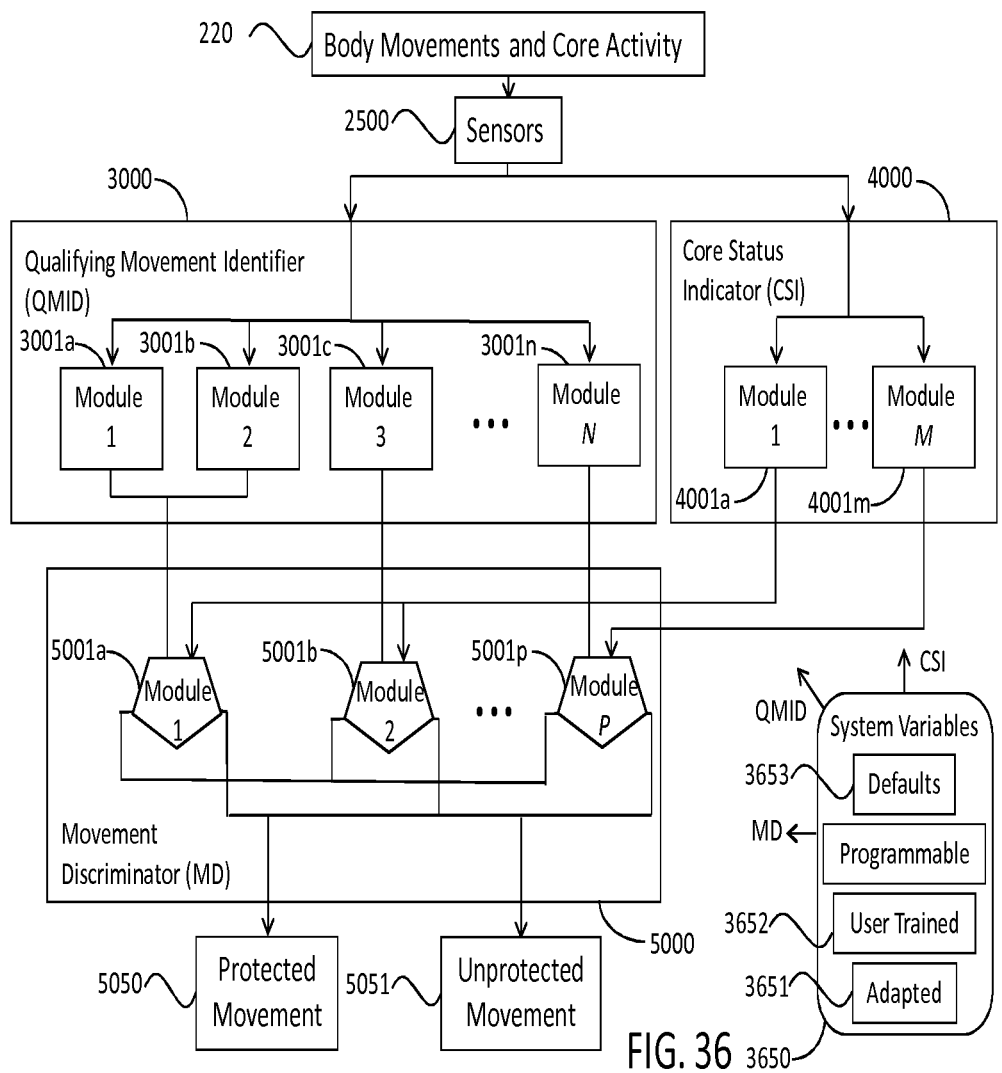
FIG. 36 illustrates an example of how the QMID modules and CSI modules may be interconnected to work together and interface to the MD.

The QMID modules and CSI modules may be associated and optimized to work together as described above. This is illustrated in FIG. 36 where N QMID 3001*n* modules and M CSI modules 4001*m* are shown. The output of the associated modules may connect to the same Movement Discriminator module 5001*a*-5001*p* as shown in the figure where the outputs of QMID modules 1 and 2 pair with CSI module 1 and go to MD module 1. And QMID module 3 may pair with CSI module 1 and go to MD module 2. This teaming of the QMID, CSI, and MD modules may occur to optimize use of the available information and organize data flow through the signal processing blocks. Additional teaming associations are shown in the figure. There may be a different number of modules in each of the blocks, teamed in an appropriate way. For example, in FIG. 36, there are N QMID, M CSI, and P MD modules.

Some of the operating parameters of these signal processing blocks include thresholds and window durations. At any one time, the system may utilize operating parameters that may be a combination of default values, programmable values, user trained, and adapted values. User Trained values may be determined through initialization sequences or training with the user. Use of changeable operating parameters is indicated in the figure with the System Variables box 3650 on the right lower corner of FIG. 36. Some operating parameters may be adapted or determined through usage. Other methods for determining operating parameters may be used.

In one embodiment, only one QMID Flag may be evaluated at a time. The Movement Discriminator 5000 may be programmed to arbitrate or prioritize certain modules over others and may enforce the evaluation of one QMID Flag at a time. When a QMID flag is set, the Movement Discriminator 5000 may hold off on setting any more QMID flags until a determination of a protected or unprotected qualifying movement is completed.

Signaling Unit

The Signaling Unit turns on when the Movement Discriminator output is Unprotected Movement=1. It can be programmed to signal for duration of time that may be fixed programmable, calibrated, or context dependent and is controlled by the Timer block 7015 in FIG. 33. The Signaling Unit may be turned off either by a Time-Out of the Timer with the duration of time exceeded or by a contraction of the core.

Core Score Keeper

Both the Protected Movement and Unprotected Movement outputs of the Movement Discriminator are input to the Core Score Keeper 6000. For each decision of the Movement Discriminator 5000, the Core Score Keeper 6000 may keep the decision bit (Protected or Unprotected), timestamp, and module type—which will track the type of qualifying movement flagged). This will allow the Core Score to be calculated for different periods of time as well as periods of different types of activity. Associated with accounting for each Protected Movement is a reset of the QMID Flag. Core Score Keeper 6000 inputs are shown in FIG. 33.

Computationally Efficient Implementation

In the description above, each of the QMID modules, CSI modules, and Movement Discriminator modules operate in parallel.

Figure 37:
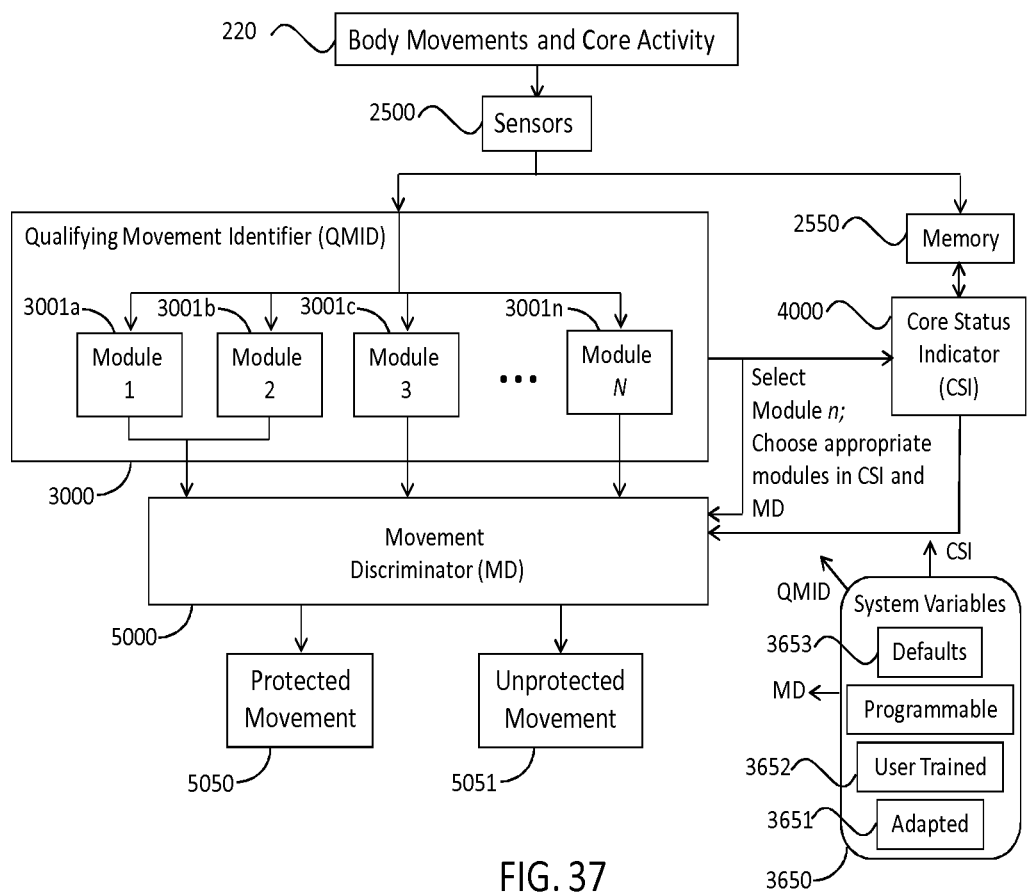
FIG. 37 illustrates a computationally efficient implementation made possible by the high clock speeds and computational power available in microprocessors.

In implementations where only one QMID flag can be raised at one time, until it is resolved as a Protected or Unprotected Movement, a more computationally efficient implementation may be possible. This approach is made possible by the high clock speeds and computational power available in microprocessors. While being a computationally efficient implementation, it is substantially similar and may be equivalent to the description of FIG. 36. FIG. 37 illustrates this by showing an arrow from the QMID block to the CSI block. The QMID block may identify which modules are close to identifying a Qualifying Movement or which may have identified a Qualifying Movement. This may then select the appropriate module in the Core Status Indicator block that may optimize the evaluation of the core contraction in relation to a specific movement that set the QMID flag.

As described earlier, samples from the sensors may be stored in memory 2550. Upon identifying a Qualifying Movement, the QMID block may provide the CSI block with a QMID Flag=1 and information as to which module set the flag and time stamped data indicating what set the flag and additional data such as when the body exceeded (for example) a velocity threshold. The CSI block may then go back into stored memory and evaluate the core over the relevant period of time. It may then provide data regarding the core to the Movement Discriminator.

Thus, the CSI block 4000 may operate in real time or may look back in time to evaluate core contraction support based on status flag and data from the QMID block. The associated data from the QMID module and the CSI module may then be passed along with the QMID flag and module information in order for the MD to evaluate and detect a protected or unprotected movement.

The computationally efficient implementation may result in power savings since many of the module computations that are not needed are not performed.

Implementation Example

In FIG. 38, a simple illustrative example is shown. Let us assume the device is utilizing a Single Device-Single Sensor Group configuration and contains an FSR, a 3-axis accelerometer, and a 2-plane gyro configured to operate in the x-z plane and the y-z plane. Further suppose the device is housed as shown in FIG. 17 and worn as shown in FIG. 12*b*.

The accelerometer and gyro data are input to the Qualifying Movement Identifier and Core Status blocks, and the outputs of these blocks feed the Movement Discriminator block of FIG. 36. The input to the Core Status block may come from the FSR. Since in typical configurations the FSR resistance reduces with applied force, a circuit may be required to translate this resistance change into a signal with the appropriate polarity for use in the system as one skilled in the art would understand. Referring to FIG. 36, let us assume that Module 3 in the Qualifying Movement Identifier has been programmed to respond to identify hip rotation, and in particular rotation of the hips exceeding a hip rotational velocity threshold.

Let us suppose the user is standing with feet stationary, and rotates a quarter turn in the $\Theta_y$ direction, generating the Body Rotational Velocity signal plot versus time 3800*a* shown in FIG. 38*a*. This rotation is measured by the x-z plane gyro and may be identified as pitch rotation. Suppose Module 1 in the QMID is configured to identify the sitting to standing transition which may identify a change in position in the y-dimension utilizing the accelerometer. Since there is no appreciable change in the y-dimension, Module 1 may remain in observation mode and continue to monitor the sensor data 2599. When Module 3 in the QMID block identifies that the body rotational velocity exceeds the Body Rotational Velocity Threshold, a check is performed to see if the velocity exceeds this threshold for a minimum period of time $T_{velocity\_y\_min}$ 3800*b* as shown in FIG. 38*b*. This is a minimum period of time that the velocity in the y-dimension must exceed the Body Rotational Velocity Threshold in order for Module 3 to set the QMID flag. The QMID block then indicates to the Movement Discriminator that a qualifying movement has been identified through the setting of the QMID flag. Data may then be pulled from memory to identify the timestamps of when the body rotational velocity exceeded the body rotational velocity threshold. This data may be used to identify the timestamps of the start and end of the qualifying movement 3800*c* shown in FIG. 38*c*. A look-back window may then be established with width $T_{lookback}$ ending just before the start of the identified qualifying movement 3800*d* as shown in FIG. 38*d*.

Let us suppose the user's core was contracted just before the movement was started 3800*e* as shown in FIG. 38*e*. When the user's core was contracted, the FSR resistance decreases and may be sensed by an FSR Output Circuit comprised of the FSR, a resistor, and a supply voltage. For example, a series resistance network may be configured with a resistor and FSR placed in series. This combination may be placed across a supply voltage, for example, 3V. The resistor, for example may be a 10 kΩ resistor and may connect on one end to the FSR and the other end to the GROUND. The FSR may connect on one end to the 3V supply and on the other end to the resistor. The output port of the circuit may be the node where the FSR and resistor connect. When the force applied to the FSR is small, for example when the core is not contracted, the resistance of the FSR may be relatively high. For example, the FSR resistance may be 50 kΩ when the user's core is not contracted. The voltage measured at the output port may then be 0.5V as one skilled in the art may understand. When the core is contracted, the increase in force on the FSR may cause the resistance to decrease to 2.5 kΩ. The voltage measured at the output port may increase to 2.4V as one skilled in the art may understand. The output of the FSR Output Circuit may have a shape similar to the core contraction 3800*f* as shown in FIG. 38*f*. The Core Status block may compare the output of the FSR Output Circuit with an FSR Circuit Threshold. The FSR Circuit Threshold may be dynamically generated by averaging the minimum and maximum voltage output from the FSR Output Circuit. The Core Status block 3800*g* may have output CS=1 when the FSR Output Circuit is greater than the FSR Circuit Threshold as shown in FIG. 38*g*. Additional qualifiers may be utilized to increase the reliability of the system. For example, $T_{core\_pressure\_min}$ may be defined which may be the minimum period of time that the FSR Output Circuit must exceed the FSR Circuit Threshold to identify a valid core contraction. In addition, filtering and other linear and non-linear signal processing techniques may be used to improve the reliability of the system.

The Movement Discriminator block may determine that: a. Valid core contraction occurred; b. Core contraction CS=1 transition occurred inside the Look-Back window; and c. Core contraction remained CS=1 for the duration of the qualifying movement. Therefore, the Movement Discriminator may identify the movement as a Protected Qualifying Movement. Further, since the core contraction change from CS=0 to CS=1 occurs inside the look-back window, this may further be identified as a Protected Movement with a dedicated core contraction.

Figure 39A:
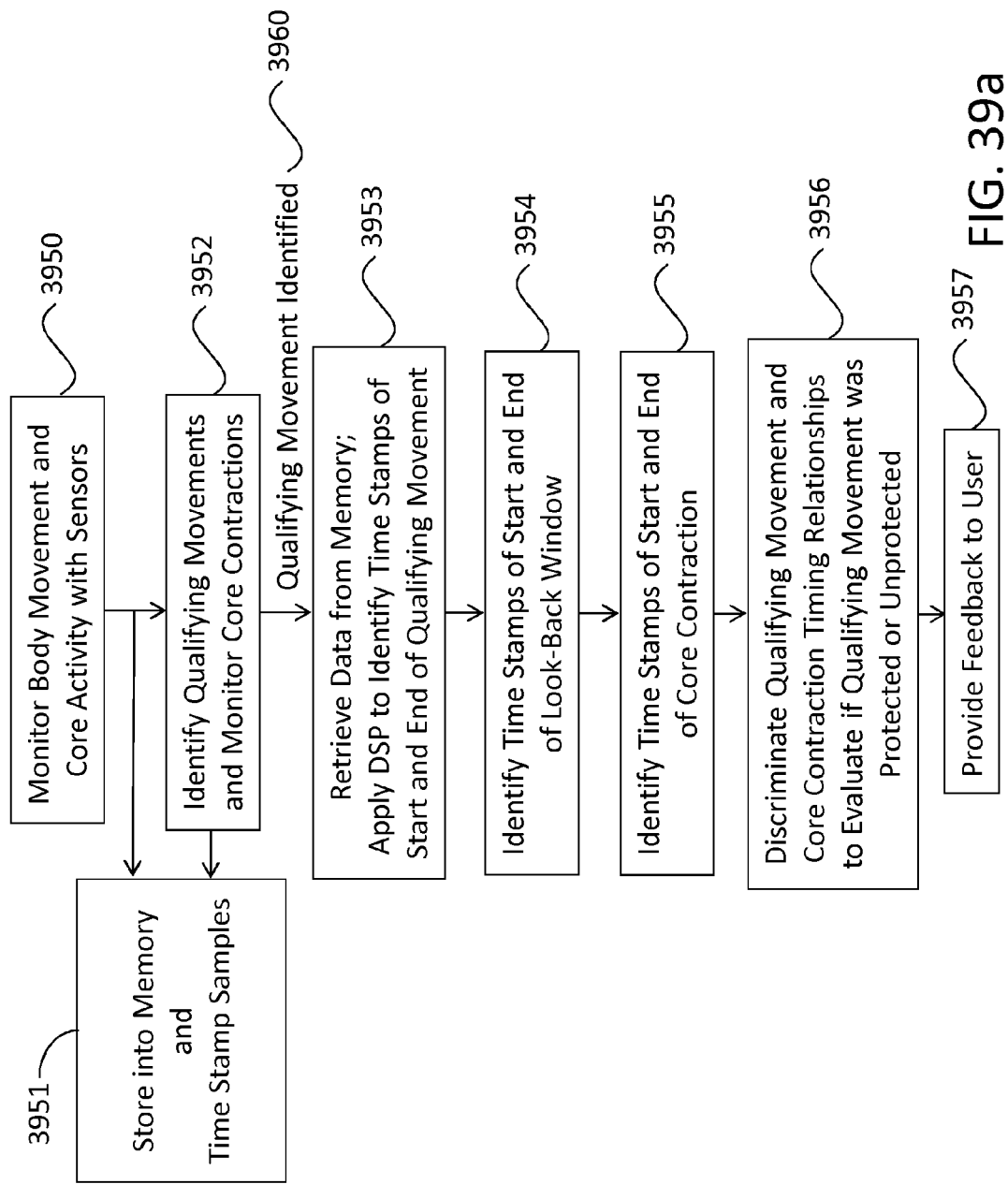
FIG. 39a illustrates a flow diagram of operation for an embodiment of the device as described in FIG. 38.

A signal flow diagram for the wearable device that encourages the development of procedural memory for core support is shown in FIG. 39*a*. Begin by monitoring user's body movements and core activity with sensors 3950. Next, identify qualifying movements and core contractions 3952. Store sensor data, interim and final calculations in the identification of qualifying movements and core contractions in memory 3951. When a qualifying movement is identified 3960, retrieve data from memory and perform digital signal processing (DSP) to determine a start and end timestamp for the qualifying movement 3953. Next, with data retrieved from memory, determine start and end timestamp for the look back window 3954. Next, with data retrieved from memory, determine start and end timestamp for the core contraction 3955. Next, discriminate the timing relationship between the qualifying movement, look-back window, and the core contraction to evaluate if the qualifying movement was protected or unprotected 3956. Finally, provide feedback to the user 3957.

Figure 39B:
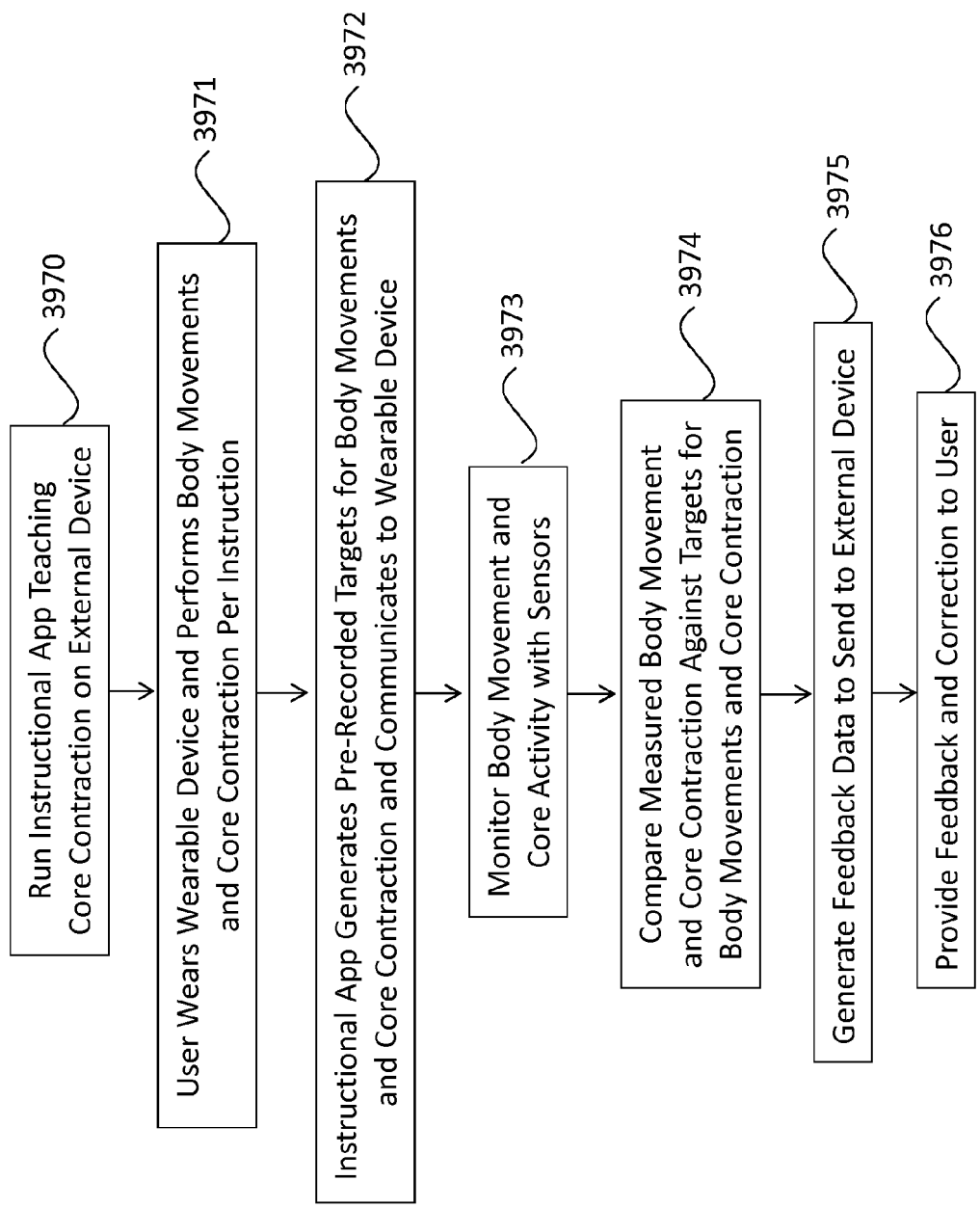
FIG. 39b illustrates a flow diagram of operation for an embodiment of the system to enable a user to properly use their core using an app.

A signal flow for the wearable device to operate in conjunction with an external app or exercise video providing instruction to user is shown in FIG. 39*b*. Begin by running the app on an external device providing instruction to a user 3970. The user may perform body movements and core contraction as instructed by the app while wearing the wearable device 3971. The app generates pre-recorded targets for body movements and core contraction and communicates said targets to the wearable device 3972. The monitor body movement and core activity with sensor 3973. The body movements and core contraction of the user are compared to said targets 3974. Based on results of the comparison, feedback data is sent to the external device 3975. Feedback is provided to the user 3976. This feedback may be provided through the app. In addition, feedback may be provided by the wearable device.

Multi-Device Implementation

As described earlier, the inventive ideas may be used to implement more complex systems that may utilize more than one device. These systems may be application specific; i.e., related to specific classes of movements such as a golf swing or weight training, and may require the system to utilize one or more devices that may be placed into different configurations. Furthermore, it may require the devices to be put into specific modes to be utilized for these specific applications. One approach to program the system of one or more devices into a specific mode is to use a handheld device or PC to program the devices through a software application. Modes may include Qualifying Movements being identified by the QMID block in order for the device, as described earlier, to respond. Let us now define Critical Movements as a broader class of movements that the system may respond to. Qualifying Movements are a subset of Critical Movements.

Figure 40:
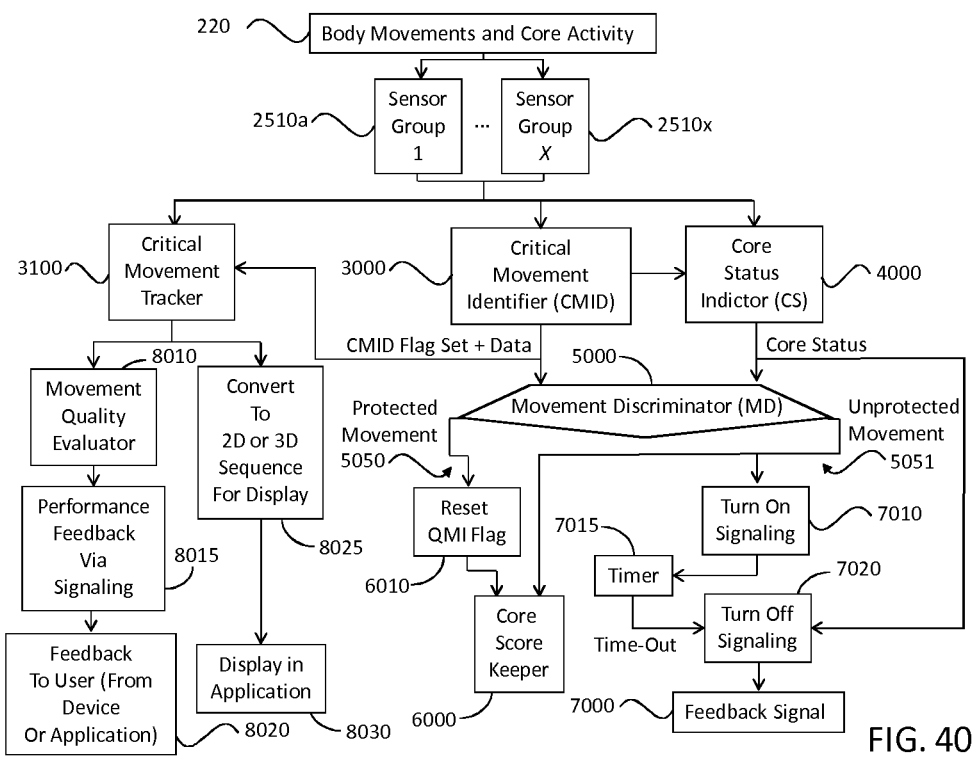
FIG. 40 illustrates a block diagram of a system utilizing a Critical Movement Identifier block in place of the Qualifying Movement Identifier.

Through the software application, specific software modules may be loaded into the different blocks in the block diagram of FIG. 40 in order to best support a specific application. This may require devices with different sensor group configurations and packaging and attachment methods to be used and attached to or close to the body using specific instructions. The Critical Movement Identifier block may operate on data received from all sensor groups, enabling modules in the CMID block to utilize the maximum amount of information.

When the system identifies a Critical Movement, it may: if appropriate, evaluate contraction of the core before and during the Critical Movement and provide feedback as described earlier; if appropriate, evaluate for more specific uses of the core, suited to the identified Critical Movement and provide feedback as described earlier; utilize available sensors to track and provide feedback to the user; or/and implement the above in combination.

The data that is fed back to the user may be in many different forms including: audible instruction through a handheld device or PC running an associated application; audible signals such as beeps or tones from a signaling device to indicate performance; or rendering of data from a sensor attached to a known part of a body moving through 2D or 3D space.

In FIG. 40, a Critical Movement Identifier (CMID) block is put in place of the QMID block. The CMID block may communicate with CSI and MD blocks as did the QMID block. The CMID block may also communicate with a new block called the Critical Movement Tracker block. This block tracks movement of sensor groups and may connect to at least two blocks. The first is called Convert to 2D or 3D Sequence for Display converts the movements to 2D or 3D space and prepares the data for display in an associated application. The second goes to the Movement Quality Evaluator block that evaluates the movement of the sensor and equivalently the body part on which the sensor is connected. The output of the Movement Quality Evaluator is the Performance Feedback via Signaling block that provides specific feedback to the user regarding specific movements.

Examples of a multi-device system were introduced earlier. They include: Device for Improving Golf Putting: Place a single-sensor group device for a Qualifying Movement and core contraction tracking on the waist and a second single-sensor group device that may include an accelerometer and gyro on the right wrist (for a right handed golfer). The Critical Movement Identifier block may identify the putting stance through the following movement features: a. Sensor group in the device on the waist registers substantially little body movement in the left to right direction, body may be mainly upright with a slight bend at the waist forward while simultaneously; b. Sensors in the device on the wrist register wrist gently moving back and then forward. This combination of movements may cause the "Putting Stroke Module" in the CMID block to set a CMID flag. The device on the waist may evaluate the user for a core contraction and may provide feedback to the user similar to the manner already described. However, in this application it is desirable for the core to be contracted before and through the putting stroke—from the back stroke to the forward stroke, including striking the ball. Therefore, the Movement Discriminator may evaluate the relationship of the CMID block which identified the putting stroke along with data identifying when the putting stroke started and ended to determine if the core was contracted appropriately. The Movement Quality Evaluator may evaluate the hand movement back and then forward to check how much the hands traveled in substantially the same line in 3D space. Depending upon user defined inputs such as Golfer Level, the hand movements may be evaluated for varying degrees of smoothness of movement and movement accuracy. In addition, measurement results such as acceleration and deceleration may also be monitored with feedback provided to the user. The application running on the handheld device or PC may also have a teaching element to explain the key performance measures for the specific movement.

Weight Training: Place a single-sensor group device for a Qualifying Movement and core contraction tracking on the waist and a second single-sensor group device with an accelerometer and gyro on either wrist. A third device on the alternate wrist may be desirable for some users. Utilize hand movements in addition to body movements in order to better identify more complex Qualifying Movements such as dumbbell curls. The focus of this system may be to utilize core contraction during exercises utilizing hand movements. Most gym exercises utilizing hand movements may benefit from core contraction support during exercises in which the hands are moving.

The inventive wearable device may also be used with gym and pilates equipment, and similar equipment where a user performs an exercise where the body engages with a selectable variable load. The load is typically a weight that the user must move in a physical exertion in one direction, followed by a movement in the reverse direction. For example on an arm curl machine, the seated user may grip handles with arms nearly extended, and perform the exercise by pulling the handles toward the shoulders. The movement in the reverse direction would be extending the arms back out toward the extended position. Both the action of pulling the weight toward the body, and extending it out may be considered Qualifying Movements. Most exercise machines utilize pulleys to translate the load, which may be provided by weights as in the example just presented, to exercise certain parts of the body. Pulleys include a wheel on an axel that supports movement of a cable or a belt along its circumference. Typically, there is a weight on one side of a cable and a handle or bar on the opposite side of the cable with a pulley in between. Most exercise machines have more than one pulley to effectively convert the load to exercise specific parts of the body. The inventive device may be used to develop core support through portions of the exercise where the body movement causes a pulley to rotate. Therefore, rotation of the pulley may be identified as a Qualifying Movement. By having a sensor or sensors monitor rotation of the wheel in the pulley, and communicating this rotation to the device, the inventive wearable device may simultaneously monitor the core and provide feedback to the user to encourage or develop core support through the exercise movement. The exercise equipment may include a sensor or sensors to identify rotation, and a vehicle to communicate this rotation of the inventive device, allowing the inventive device to evaluate proper core support through the exercise and provide feedback to the user. Alternatively, the exercise equipment may be configured to receive data from the inventive device when the user's core is contracted and provide feedback to develop or encourage core support through the exercise movement. An external device configured to communicate to both the inventive wearable device and the electronics on the exercise equipment may be used to evaluate core usage during the exercise and provide feedback accordingly.

The inventive wearable device may be used with exercise videos or apps. In this application of the inventive device, it is assumed that the user follows the direction of the instructor or instruction provided from the video. Intervals when the user's core should be contracted may be encoded with the video data. During playback of the video, the external device performing the playback may communicate with the inventive wearable device. Core contraction may be compared with the timing of the desired core contraction and feedback may be provided. In addition to firming of the core, movement of the core in the monitored position inward, outward, or neutral may be monitored by the device with feedback provided. This will enable experts such as physical therapists to teach a very specific contraction of the core with corresponding movement of the abdominal region. This may allow the inventive device to be a part of a self-teaching system for proper core usage.

Target Tracking Movement Discriminator

In this section, we describe a Target Tracking Movement Discriminator that may be used in the implementations described earlier in place of the Movement Discriminator block. The Movement Discriminator block described earlier receives its input as binary outputs from the Critical Movement Identifier (or equivalently Qualifying Movement Identifier) and the Core Status Indicator blocks. A single threshold is used throughout the movement and the core is considered either contracted or not contracted. With the Target Tracking Movement Discriminator, more complex movements may be tracked where the core contraction intensity may be required to vary over time corresponding to different parts of a movement. Furthermore, it may have a window with a minimum and maximum core contraction intensity making varying the core contraction intensity part of a skill development system.

Figure 41:
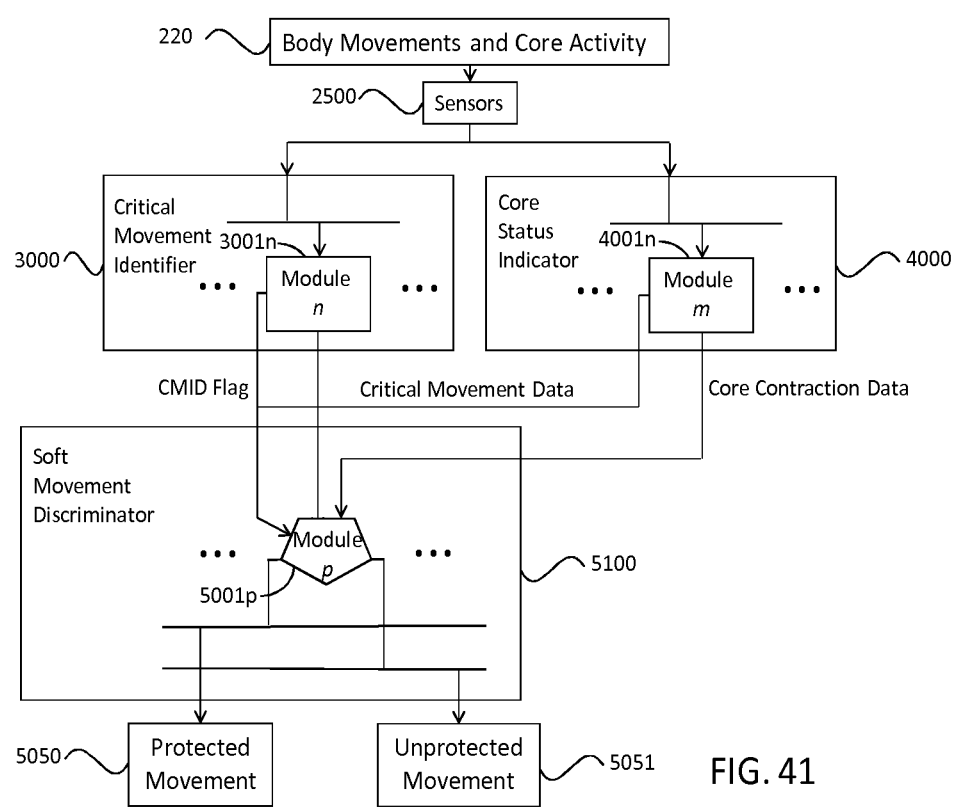
FIG. 41 illustrates a block diagram of a Soft Movement Discriminator.

A block diagram of a system utilizing a Target Tracking Movement Discriminator 5100 is shown in FIG. 41. The output of the Critical Movement Identifier block may include the Critical Movement Identifier flag that is used to trigger the Core Status Indictor and Target Tracking Movement Discriminator blocks. In addition, direct and primitive data used by the Critical Movement Identifier, along with outputs of the module identifying the Critical Movement may be passed to the Target Tracking Movement Discriminator. The Core Status Indicator may also pass the direct and primitive data used by it, along with outputs of the associated module corresponding to the critical movement flagged to the Target Tracking Movement Discriminator. The Target Tracking Movement Discriminator block may then utilize this data to determine more complex protected movement decisions.

Figure 42A:
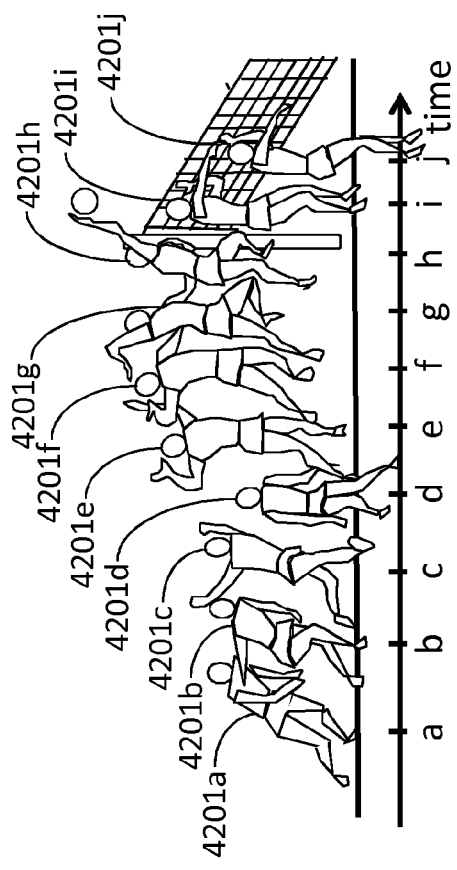
FIG. 42a shows the sequence of moves executing a volleyball spike in steps a-j.
Figure 42B:
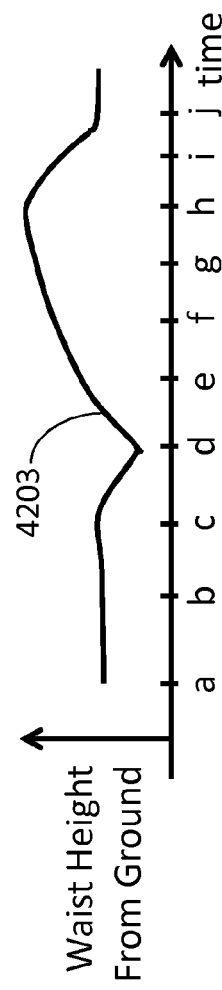
FIG. 42b shows the distance of the volleyball player's waist to the ground, plotted versus time.
Figure 42C:
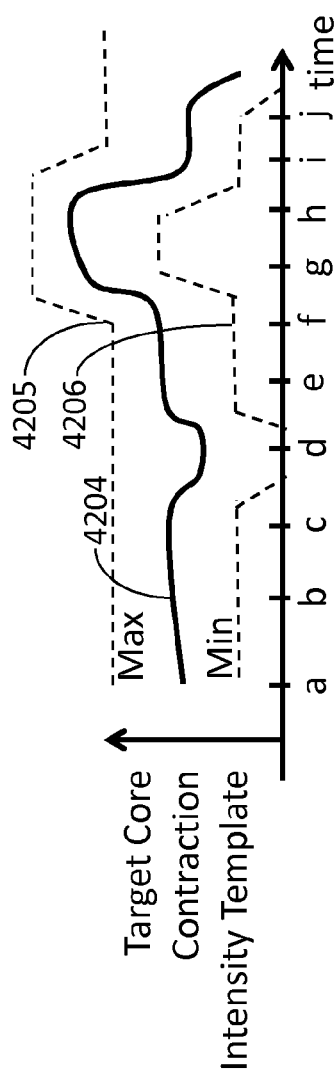
FIG. 42c shows an example of the target core contraction intensity, plotted versus time together with a minimum and maximum contraction intensity window defined for the Target Tracking Movement Discriminator block which may be utilized in advanced applications.
Figure 43A:
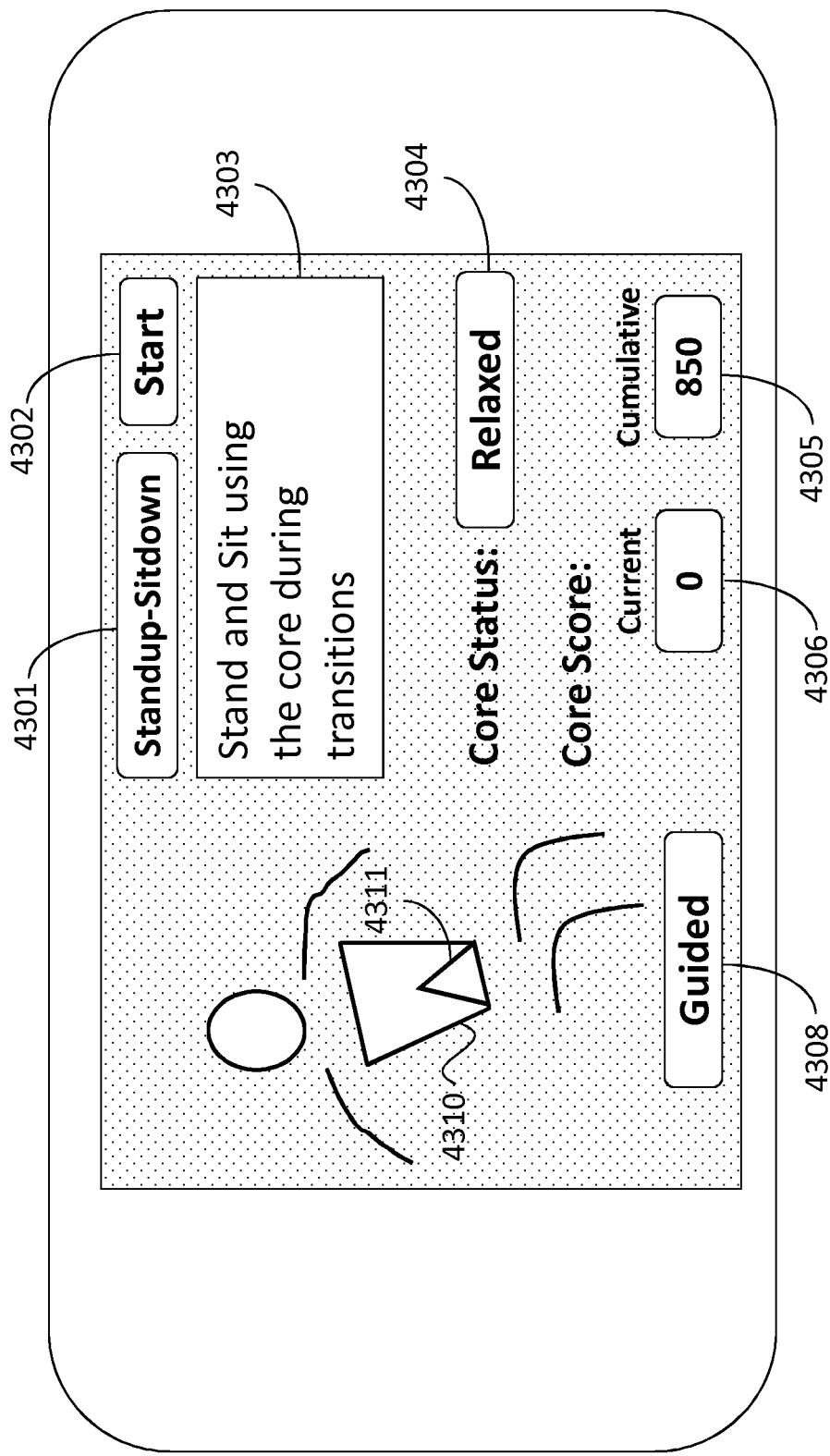
Figure 43B:
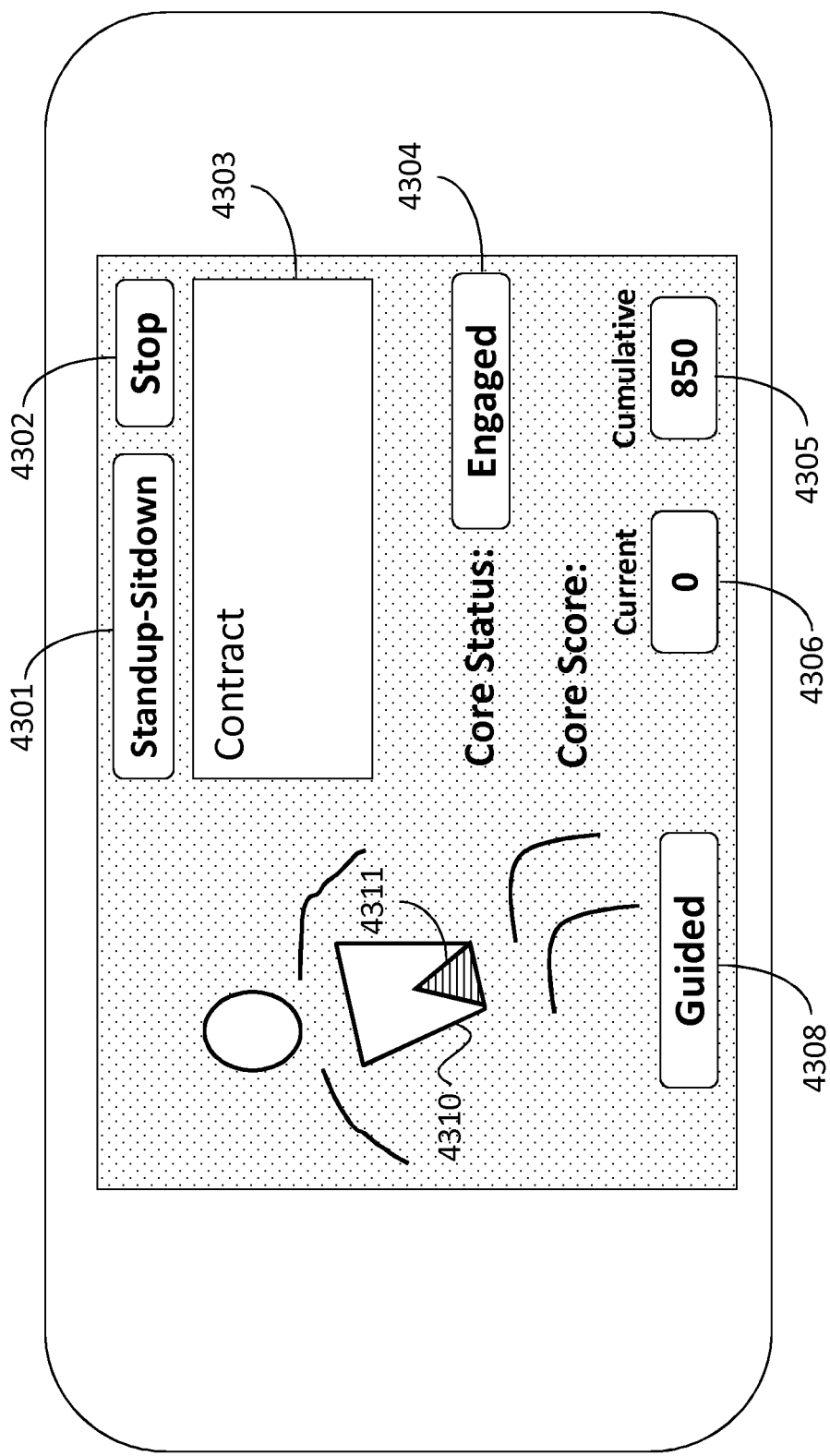
Figure 43C:
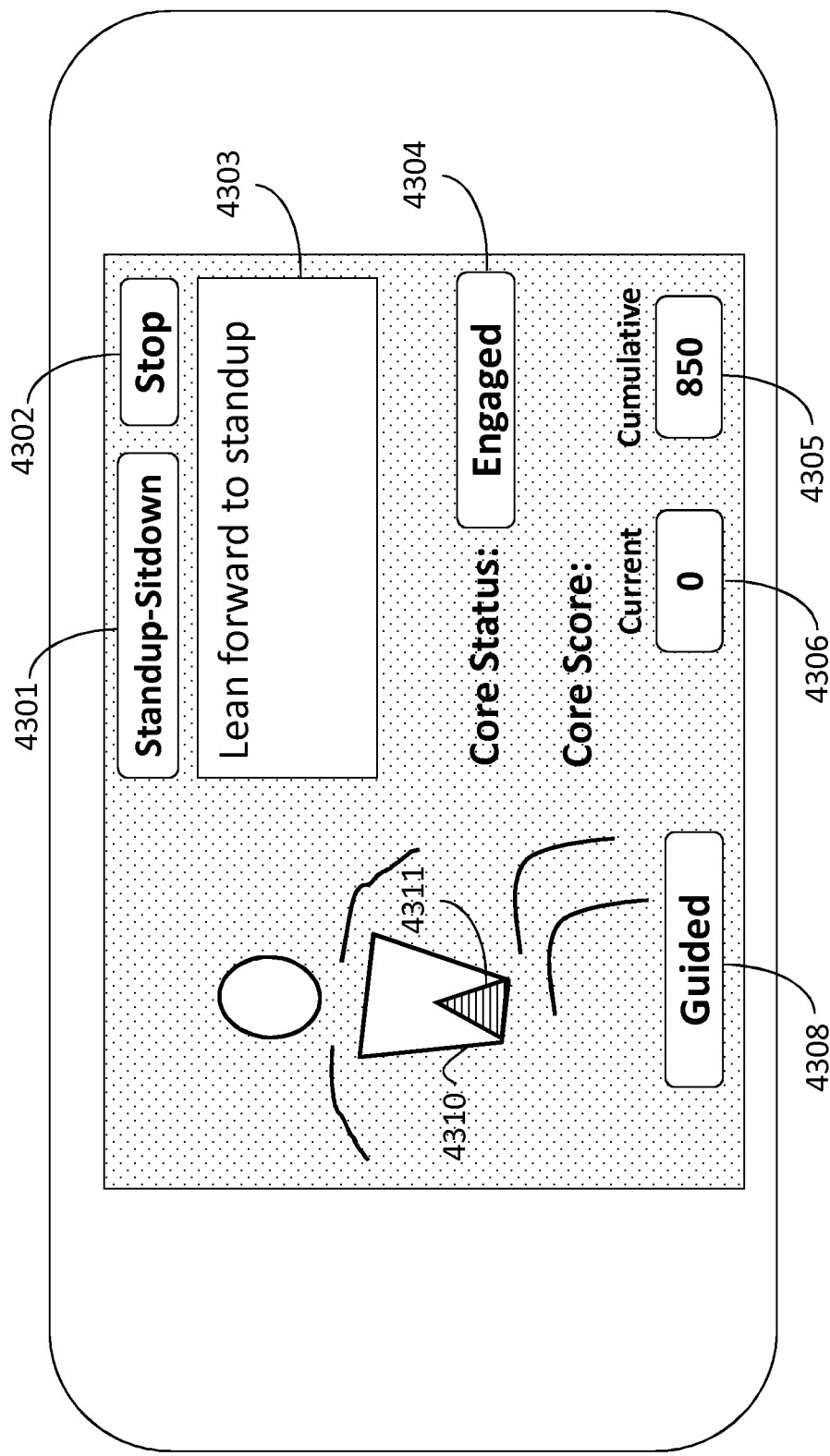
Figure 43D:
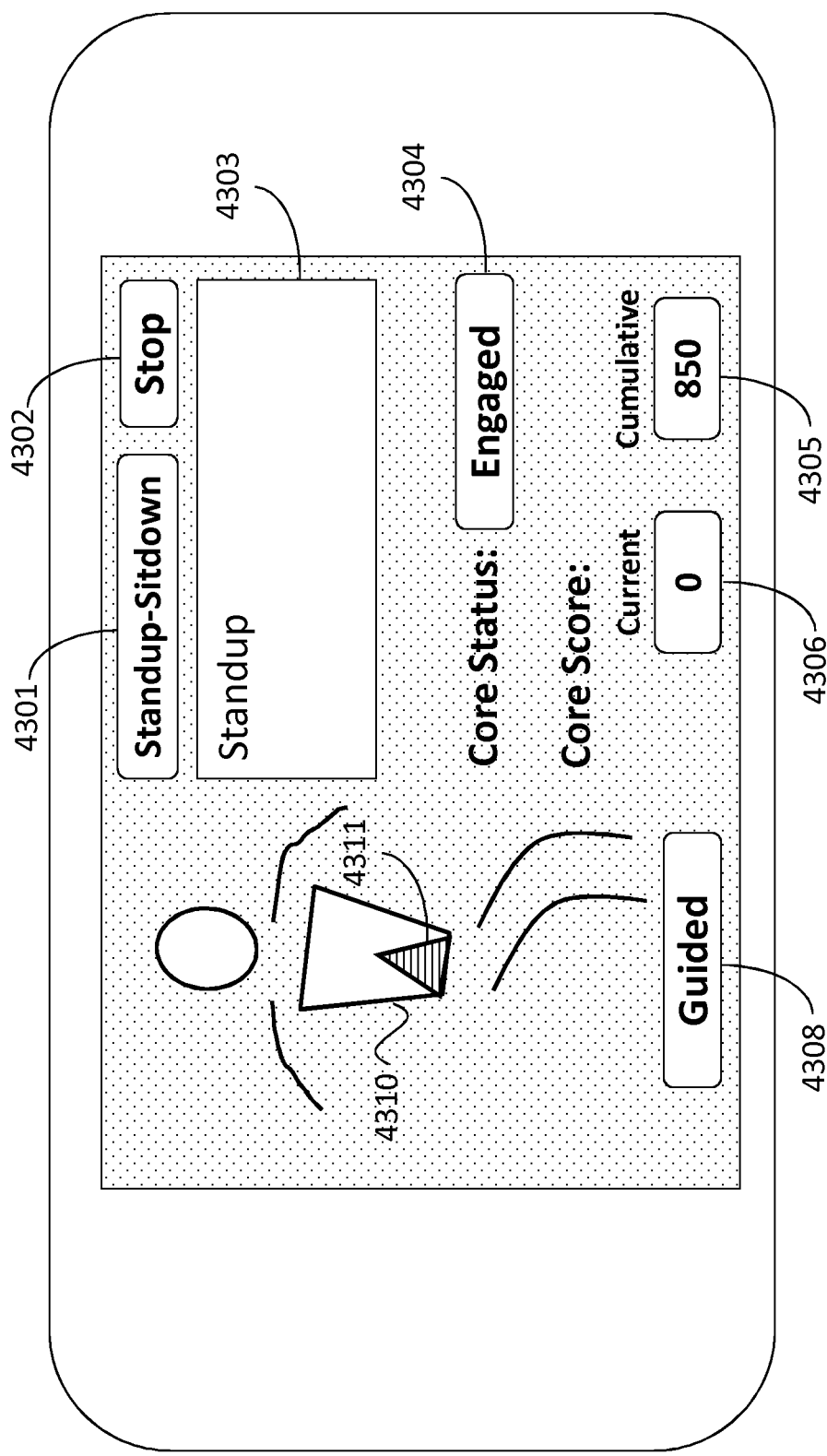
Figure 43F:
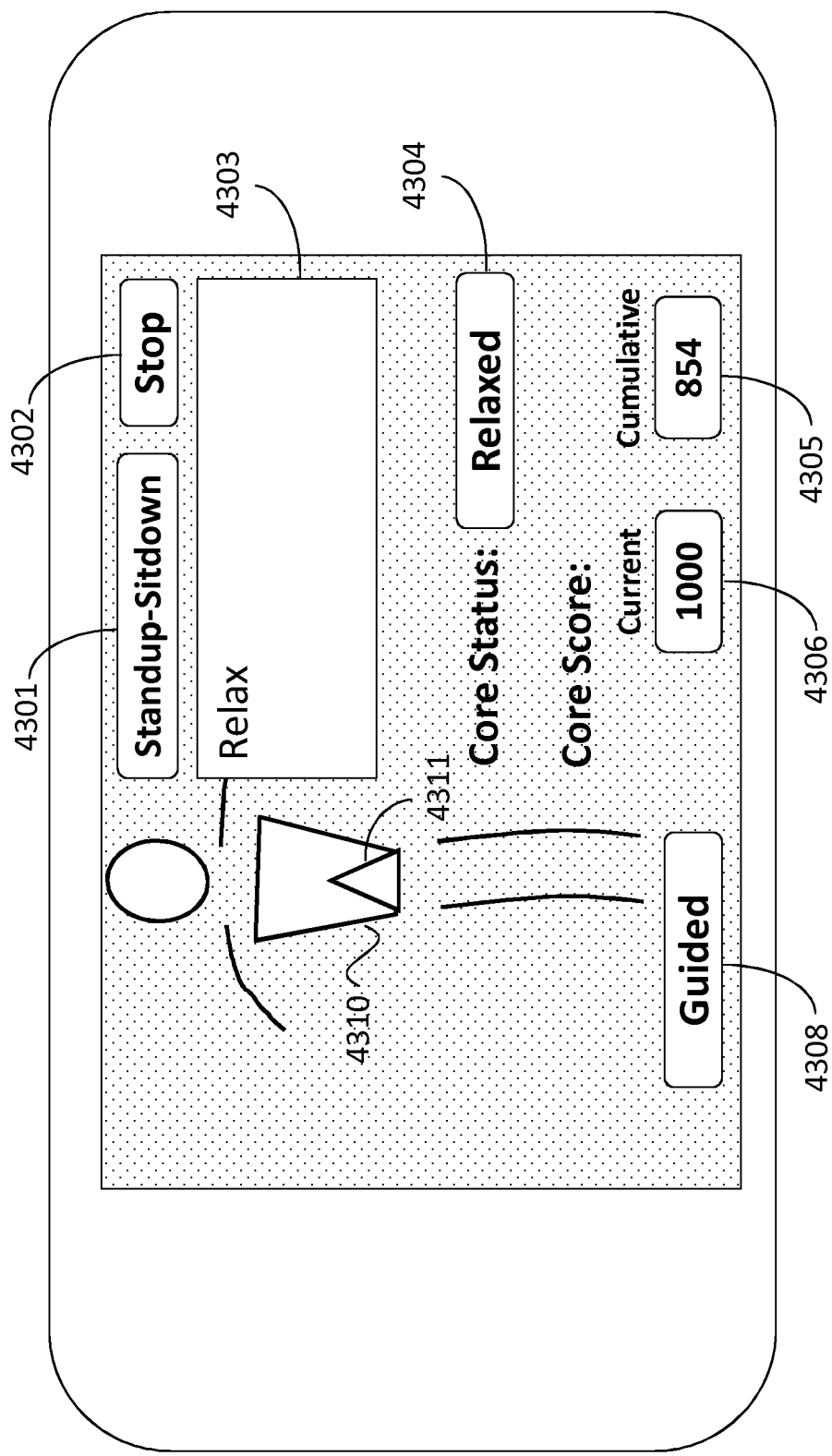

The Target Tracking Movement Discriminator block enables the movement and core contraction to be tracked during complex movements such as spiking in volleyball 4201*a*-4201*j*. An example is shown in FIG. 42*a* where the sequence of moves on a volleyball spike is shown in steps a-j. In FIG. 42*b*, the distance of the user's waist height 4203 to the ground is plotted versus time. In FIG. 42*c*, an example of the target core contraction intensity is plotted. A minimum and maximum contraction intensity window may be defined for the Target Tracking Movement Discriminator block 4204-4206 as shown in FIG. 42*d* and used for advanced users. In this case, at any one point in time throughout the qualifying or critical movement, there may be a minimum and maximum allowed core contraction to pass as a protected movement.

A system utilizing Target Tracking Movement Discriminator may require calibrations to evaluate thresholds on a user. These calibrations may be performed utilizing an application running on a handheld device or PC. Through calibrations, core contraction levels of different intensities may be recorded and stored and used in Target Tracking Movement Discriminator algorithms. For example, a user may be requested to contract their core at intensity levels of 100%, 50%, 25%, 12.5% a number of times in succession with pauses in-between. These may be recorded and averaged and placed into look-up-tables. Extrapolation may be utilized to fill entries in the look-up-tables.

Software Interface

An important aspect of the inventive system is the linking the simultaneous operation of the device with a software program running on a handheld device such as a smart phone or electronic pad or to a PC. This enables interactive teaching and training programs to be run in software while the user performs movements and core contraction, providing real time feedback regarding contraction of the core.

Some aspects of the software program may include the following: Animation or video clips teaching proper and improper movement; Real time monitoring of the core; Real time feedback regarding proper contraction of the core; Reporting of the Core Score.

A conceptual example of the elements of a training software program is shown in FIG. 48*a* through FIG. 48*f*. Some example information that may be shown on the display is shown in FIG. 48*a* and includes: a. Start and Stop toggle button 4302 to start and stop the application; b. Core Indication on Animated FIG. 4311: Animated figure may indicate whether or not the core should be contracted or relaxed; for example, the triangle near the abdominal section of the animated figure may represent the core; as an example, when the core is not contracted it appears as an empty triangle; when it is contracted, it appears as a cross-hatched triangle; c. Core Status 4304: Device communicates to software program whether the core is contracted or relaxed; Status is shown in the program; d. Core Score for that particular session including Cumulative 4305 and Current Exercise 4306; e. Exercise Name 4301 and Description 4303; d. Ability for Users to program or choose their own training session including order of programs and any programmable parameters of each program; e. Animated description of the desired body movement illustrating the use of the core with a separate animation in the area of the core 4310; f. Ability for the User to choose a Guided or Autonomous exercise 4308—When Guided, it may specify when to contract or release the core, and when Autonomous, it may not specify when to contract or release the core but only keep a Core Score.

An example is shown in FIG. 43*a* through FIG. 43*f*. In this example, the user moves from a seated position to a standing position. The user is encouraged to contract his or her core before and through the movements and to relax them in the moments in between. This is an example of the combination of the device and the training software providing real-time feedback on the use of the user's core.

Embodiments disclosed allow monitoring user core muscles, thereby making learning and developing core contraction techniques and procedural memory relatively easy. Embodiments further allow provision of real-time feedback to the user, thereby informing the user of the correctness of each core contraction. Easy monitoring of core movement/contraction at a very low cost is now possible. Embodiments further reduce and possibly eliminate the need for physical therapists or personal trainers to use their hands on their clients to feel/monitor their core.

Embodiments disclosed make possible self teaching of timing aspects in core training since the user core and body movements and their timing relationship can by simultaneously monitored in real time.

Embodiments disclosed enable and allow users to self-teach and develop procedural memory wherein target/desired timing relationships between core contractions and specific body movements that require repetition can be achieved. Such repetition may be most effectively taught if the timing sequence may be encouraged and practiced throughout the day including morning, noon, and night.

Finally, embodiments make for easy self-teaching without the need for an instructor. There is a movement of increased personal responsibility for health care in the US as a result of increasing health costs and individuals enjoying active lifestyles to higher ages. Embodiments disclosed make it easy for an individual to learn proper usage of their core muscles.

The figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

We claim:

1. A method for development of procedural memory for core muscles based support, comprising:
   providing a movement sensor and a contraction sensor that are in communication with a signal processor, wherein the movement sensor, the contraction sensor and the signal processor are components of a wearable device;
   detecting a movement of a body with the movement sensor;
   detecting a core contraction of the core muscles located in an abdominal area of the body with the contraction sensor;
   determining by the signal processor that the movement of the body is a qualifying movement that benefits from the core contraction;
   detecting by the signal processor, a timing relationship between the qualifying movement of the body and the core contraction of the core muscles;
   determining by the signal processor, that the qualifying movement is either a protected qualifying movement where the core contraction is detected by the contraction sensor during the qualifying movement detected by the movement sensor or an unprotected qualifying movement where the core contraction is not detected by the contraction sensor during the qualifying movement detected by the movement sensor; and
   providing an output device which provides immediate local feedback immediately upon at least one of the following: the core contraction, the protected qualifying movement detection or the unprotected qualifying movement, wherein the output device is part of the wearable device.

2. The method of claim 1 further comprising:
   providing a buzzer or a speaker with a sound generator which is the output device;
   generating a feedback signal with the sound generator; and
   emitting the feedback signal from the buzzer or the speaker;
   wherein the output device is part of the wearable device.

3. The method of claim 1 further comprising:
   providing a force sensing resistor (FSR) in a wearable device; and
   utilizing the force sensing resistor (FSR) to identify the core contraction.

4. The method of claim 1 further comprising:
   providing in the wearable device an accelerometer or a gyro as the movement sensor to identify the qualifying movement.

5. The method of claim 1 further comprising:
   providing in the wearable device including one or more means to communicate to a personal computer (PC), a smart phone, or a portable device.

6. The method of claim 5 further comprising:
   receiving feedback by the personal computer (PC) or handheld device.

7. The method of claim 1 further comprising:
   providing in a wrist wearable device comprising a wrist movement sensor and means to communicate with the signal processor wherein the coordination of a body turn and movement of the wrist may be optimized for a type of athletic movement.

8. The method of claim 7 wherein the athletic movement comprises athletic movements in at least one of a movement in a game of golf, tennis, baseball, and volleyball.

9. A method for development of procedural memory for core muscles based support, comprising:
   providing a movement sensor and a core contraction sensor adapted to be worn by a user, the movement sensor and the core contraction sensor on a wearable device in communication with a signal processor in an external device;

detecting a movement of a body with the movement sensor;

detecting a core contraction of core muscles located in an abdominal area of the body with the core contraction sensor;

detecting by the signal processor, a timing relationship between the movement of the body and the core contraction of the core muscles;

determining by the signal processor, if the movement is a protected qualifying movement where the core contraction is detected by the core contraction sensor during the qualifying movement detected by the movement sensor or an unprotected qualifying movement where the core contraction is not detected by the core contraction sensor during the qualifying movement detected by the movement sensor; and providing an output device which provides immediate local feedback immediately upon at least one of the following: the core contraction, the protected qualifying movement detection or the unprotected qualifying movement.

10. The method of claim 9 further comprising:
providing a sound generator which is the output device;
emitting the feedback signal from the audio output device.

11. The method of claim 9 further comprising:
providing a force sensing resistor that is the core contraction sensor in the wearable device; and
identifying the core contraction using the force sensing resistor.

12. The method of claim 9 further comprising:
providing an accelerometer or a gyro in a wearable device, wherein the accelerometer or the gyro is the movement sensor;
receiving by the signal processor, signals from the accelerometer or the gyro; and
determining by the signal processor, that a movement is a qualifying movement.

13. The method of claim 9 wherein the external device is at least one of:
a personal computer (PC), a smart phone, an electronic pad or a portable device.

14. The method of claim 9 further comprising:
providing a memory on the external device and storing the feedback of the core contraction, the protected qualifying movement detection or the unprotected qualifying movement.

15. The method of claim 9 further comprising:
providing in a wrist wearable device comprising means to communicate with the single or plurality of sensors and the single or plurality of signal processors, monitoring the core and further monitoring movement of the user's hips;
combining the monitoring of wrist movement and turn of the user's hips, wherein the coordination of a body turn and movement of the wrists may be optimized for a type of athletic movement.

16. The method of claim 15 wherein the athletic movement comprises athletic movements in at least one of a movement in a game of golf, tennis, baseball, and volleyball.

17. A method for development of procedural memory for core muscles based support, comprising:
providing a core contraction sensor, a movement sensor and an output device within a wearable device wherein the core contraction sensor and a movement sensor are in communication with a signal processor;
detecting a movement of a body with the movement sensor;
detecting a core contraction of core muscles located in an abdominal area of the body with the core contraction sensor;
detecting by the signal processor, a timing relationship between the movement of the body and the core contraction of the core muscles;
determining by the signal processor, if the movement is a protected qualifying movement where the core contraction is detected by the core contraction sensor during the qualifying movement detected by the movement sensor or an unprotected qualifying movement where the core contraction is not detected by the core contraction sensor during the qualifying movement detected by the movement sensor; and
providing immediate local feedback by the output device immediately upon receiving in response to an output signal from the signal processor.

18. The method of claim 17 wherein the output signal from the signal processor is triggered by the core contraction.

19. The method of claim 17 wherein the output signal from the signal processor is triggered by the protected qualifying movement.

20. The method of claim 17 wherein the output signal from the signal processor is triggered by the unprotected qualifying movement.

* * * * *